US012808874B2

(12) United States Patent
Ong et al.

(10) Patent No.: US 12,808,874 B2
(45) Date of Patent: Nov. 24, 2026

(54) BIOMARKER WITH THERAPEUTIC IMPLICATIONS FOR PERITONEAL CARCINOMATOSIS

(71) Applicant: SINGAPORE HEALTH SERVICES PTE LTD, Singapore (SG)

(72) Inventors: Chin-Ann Johnny Ong, Singapore (SG); Ching Ching Melissa Teo, Singapore (SG); Claramae Shulyn Chia, Singapore (SG); Grace Hwei Ching Tan, Singapore (SG); Suzanne Qiu Xuan Tan, Singapore (SG); Josephine Hendrikson, Singapore (SG); Wai Har Ng, Singapore (SG); Wee Shan Joey Tan, Singapore (SG); Ying Liu, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 1220 days.

(21) Appl. No.: 17/442,782

(22) PCT Filed: Mar. 27, 2020

(86) PCT No.: PCT/SG2020/050177
§ 371 (c)(1),
(2) Date: Sep. 24, 2021

(87) PCT Pub. No.: WO2020/197505
PCT Pub. Date: Oct. 1, 2020

(65) Prior Publication Data

US 2022/0170940 A1 Jun. 2, 2022

(30) Foreign Application Priority Data

Mar. 27, 2019 (SG) ........................... 10201902763U

(51) Int. Cl.
*G01N 31/00* (2006.01)
*G01N 33/53* (2006.01)
*G01N 33/575* (2026.01)

(52) U.S. Cl.
CPC .................... *G01N 33/5758* (2026.01); *G01N 2333/4706* (2013.01)

(58) Field of Classification Search
None
See application file for complete search history.

(56) References Cited

U.S. PATENT DOCUMENTS

| | | | | |
|---|---|---|---|---|
| 9,933,429 | B2 * | 4/2018 | Baek ................ | G01N 33/57423 |
| 2013/0137592 | A1 | 5/2013 | Honda et al. | |
| 2013/0244256 | A1 | 9/2013 | Clarke et al. | |
| 2014/0370527 | A1 | 12/2014 | Eugen-Olsen et al. | |
| 2015/0212088 | A1 | 7/2015 | Zou et al. | |

FOREIGN PATENT DOCUMENTS

| | | | |
|---|---|---|---|
| EP | 2 525 222 | A1 | 11/2012 |
| KR | 20100013349 | A | 2/2010 |
| WO | 2014142752 | A1 | 9/2014 |
| WO | 2018129329 | A1 | 7/2018 |

OTHER PUBLICATIONS

Kubala et al. Cell Reports, Nov. 20, 2018, vol. 25, No. 8, pp. 2177-2191. (Year: 2018).*
Tascilar et al. (Annals of Oncology 10,Suppl. 4:S107-S110, 1999) (Year: 1999).*
Tascilar et al. (Annals of Oncology 10,Suppl. 4:5107-S110, 1999) (Year: 1999).*
Tockman et al. (Cancer Research 52:2711s-2718s, 1992) (Year: 1992).*
Dadgar et al. (Journal of Translational Medicine, 2024 22:402 pp. 1-18). (Year: 2024).*
Kubala et al. Cell Reports, vol. 25, pp. 2177-2191, Nov. 20, 2018 (Year: 2018).*
Placencio et al. PLOS One, Jul. 24, 2015, pp. 1-18. (Year: 2015).*
Ströhlein, Michael Alfred et al., “Relative lymphocyte count is a prognostic parameter in cancer patients with catumaxomab immunotherapy,” Medical Hypothesis, 82(3): 295-299.
First Office Action and Search Report issued in Taiwanese Application No. 109110597 dated Nov. 24, 2023 (Taiwanese First Office Action with Machine Generated Translation).
Nishioka, N., et al. “Plasminogen activator inhibitor 1 RNAi suppresses gastric cancer metastasis in vivo.” Cancer Sci, Nov. 20, 2011, vol. 103, No. 2, pp. 228-232.
Peng, Y., et al. “PAI-1 secreted from metastatic ovarian cancer cells triggers the tumor-promoting role of the mesothelium in a feedback loop to accelerate peritoneal dissemination.” Cancer Lett, Oct. 26, 2018, vol. 442, pp. 181-192.

(Continued)

*Primary Examiner* — Lisa V Cook
(74) *Attorney, Agent, or Firm* — BALLARD SPAHR LLP

(57) ABSTRACT

Disclosed herein are methods treating a subject suffering from peritoneal carcinomatosis with a PAI-1 inhibitor, wherein the method comprises determining the concentration of “plasminogen activator inhibitor 1” (PAI-1) and determining the level of phosphorylation of “signal transducer and activator of transcript 3” (STAT3) in a sample obtained from the subject. Also disclosed herein are methods of detecting or determining susceptibility of a subject suffering from peritoneal carcinomatosis to treatment with a PAI-1 inhibitor.

19 Claims, 33 Drawing Sheets

(56) References Cited

OTHER PUBLICATIONS

Saini, U., et al. "Elevated STAT3 expression in ovarian cancer ascites promotes invasion and metastasis: a potential therapeutic target." Oncogene, Jun. 13, 2016, vol. 36, No. 2, pp. 168-181.
Alyami et al., Pressurised Intraperitoneal Aerosol Chemotherapy: Rationale, Evidence, and Potential Indications, The Lancet, Jul. 2019, pp. 368-377, vol. 20.
Chu et al., Peritoneal Carconomatosis in Nongynecologic Malignancy, A Prospective Study of Prognostic Factors, Cancer, 1989, pp. 364-367, vol. 63.
Dumont et al., Phase I/II Study of Oxaliplatin Dose Escalation via a Laproscopic Approach Using Pressurized Aerosol Intraperitoneal Chemotherapy (PIPOX trial) for Nonresectable Peritoneal Metastases of Digestive Cancers (stomach, small bowel and corectal) Rational and Design, De Gruyter, Plura and Peritoneum, 2018.
Elias et al., Peritoneal Colorectal Carcinomatosis Treated with Surgery and Perioperative Intraperitonea Chemotherapy: Retrospective Analysis of 523 Patients from a Multicentric French Study, American Society of Clinical Oncology, 2009, pp. 63-68.
Flanagan et al., Peritoneal Metastases from Extra-Abdominal Cancer—A Population-Based Study, European Journal of Surgical ONcology, 2018, pp. 1811-1817, vol. 44.
Franko et al., Prognosis of Patients with Peritoneal Metastatis Colorectal Cancer Given Systemic Therapy: An Analysis of Individual Patient Data from Prospective Randomised Trials from the Analysis and Research in Cancers of the Digestive System (ARCAD) Database, The Lancet, Dec. 2016, pp. 1709-1719, vol. 17.
Glehen et al., Intraperitoneal Chemohyperthermia Using a Closed Abdominal Procedure and Cytoreductive Surgery for the Treatment of Peritoneal Cardinomatosis: Morbility and Morality Analysis of 216 Consecutive Procedures, Anals of Surgical ONcology, 2003, pp. 863-869.
Izuhara et al., Inhibition of Plasminogen Activator INhibitor-1 Its Mechanism and Effectiveness on Coagulation and Fibrosis; Arterioscler Thromb Vasc Biol., 2008, pp. 672-677, vol. 28.
Jafari et al., Surgical Outcomes of Hyperthermic Intraperitoneal Chemotherapy, Analysis of the American College of Surgeions National Surgical Quality Improvement Program, JMA Surg., 2014, pp. 170-175, vol. 149.
Jayne et al., Peritoneal Carcinomatosis from Colorectal Cancer, British Journal of Surgery, 2002, pp. 1545-1550, vol. 89.
Klaver et al., Intraoperative Hyperthermic Intraperitoneal Chemotherapy After Cytoreductive Surgery for Peritoneal Carinomatosis in an Experimental Model, British Journal of Surgery, 2010, pp. 1874-1880, vol. 97.
Mogal et al., Repeat Cytoreductive Surgery With Hyperthermic Intraperitoneal Chemotherapy: Review of Indications and Outcomes, Gastrointest Oncol., 2016, pp. 129-142, vol. 7(1).
Nadiradze et al., Overcoming Durg Resistance by Taking Advantage of Physical Principles: Pressurized Intraperitoneal Aerosol Chemotherapy (PIPAC), Cancers, 2020, pp. 1-18, vol. 12.
Nishioka et al., Plasminogen Activator Inhibitor 1 RNAi Suppresses GAstric Cancer Metastasis in Vivo, Cancer Sci, 2012, pp. 228-232, vol. 103.
Ong et al., Integrative Analysis of Transcriptomic and Proteomic Profies of Ascites Identified a Targetable Non-Sanonical STAT3-Epithelial-Mesenchymal-transition Pathway in Colorectal Carcinomatosis, ScolarOne Abstracts—Abstract Proof Popup, 2019, 1 page.
Peng et al., PAI-1 Secreted From Metastatic Ovarian Cancer Cells Triggers The Tumor-Promoting Role of the Mesothelium in a Feedback Loop to Accelerate Peritoneal Dissemination, Cancer Letters, 2019, pp. 181-192, vol. 442.
Sadeghi et al., Peritoneal Carcinomatosis from Non-Gynecologic Malignancies, Results of the EVOCAPE 1 Multicentric Prospective Study, Aerican Cancer Society, 2000, pp. 358-363.
Saini et al., Elevated STAT3 Expression in Ovarian Cancer Ascites Promotes Invasion and Metastasis: A Potential Therapeutic Target, Oncogene, 2017, pp. 168-181, vol. 12.
Sereno et al., Lung Cancer and Peritoneal Carcinomatosis, Oncology Letters, 2013, pp. 705-708, vol. 6.
Sugarbaker, M.D., Paul H., Peritonectomy Procedures, Annals of Surgery, 1995, pp. 29-42, vol. 221.
Sugarbaker, M.D., Paul H., Intraperitoneal Chemotherapy and Cytoreductive Surgery for the Prevention and Treatement of Peritoneal Carcinomatosis and Sarcomatosis, Seminars in Surgical ONcology, 1998, pp. 254-261, vol. 14.
Verwall et al., Randomized Trial of Cytoreduction and Hperthermic Intraperitoneal Chemotherapy Versus Systemic Chemotherapy and Palliative Surgery in Patients with Peritoneal Carcinomatosis of Colorectal Cancer, Jounal of Clinical Oncology, 2003, pp. 3737-3743, vol. 21.
Verwall et al., Toxicity of Cytoreductive Surgery and Hyperthermic Intra-Peritoneal Chemotherapy, Journal of Surgical Oncology, 2004, pp. 61-67, vol. 85.
Wei et al., Plaminogen Activator Inhibitor-1 in Cancer Research, Biomedicine & Pharmacotherapy, 2018, pp. 83-94, vol. 105.
Wang et al., Dual-Selective Magnetic Analysis of Extracellular Vesicle Glycans, Elsevier, Inc., 2020, pp. 150-166.
Office Action issued by Taiwan Patent Office for Application No. 109110597.

* cited by examiner (A)

(B)

(C)

| No. at risk | | | | | | |
|---|---|---|---|---|---|---|
| Ascites present | 17 | 12 | 8 | 5 | 4 | 4 |
| No ascites | 50 | 37 | 27 | 16 | 8 | 5 |

FIG. 2
(A)
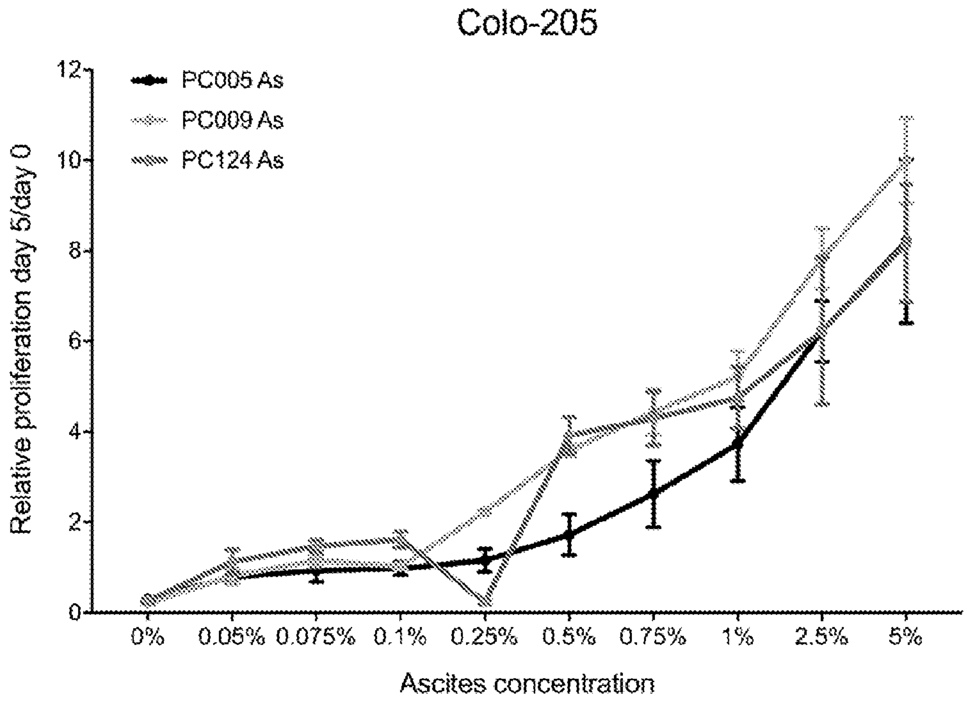
(B)
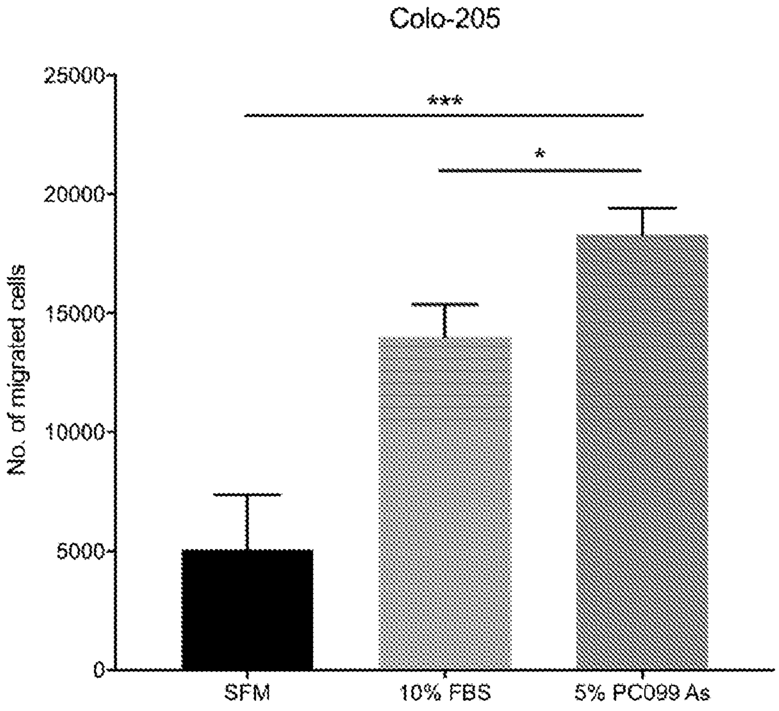

(C)

FIG. 4
(A)
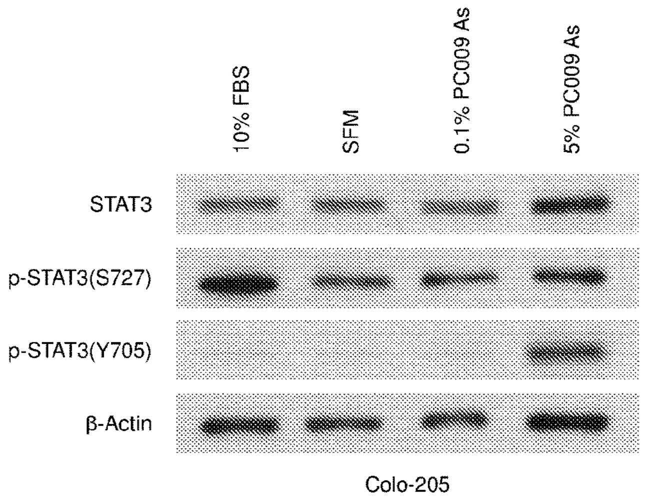
(B)
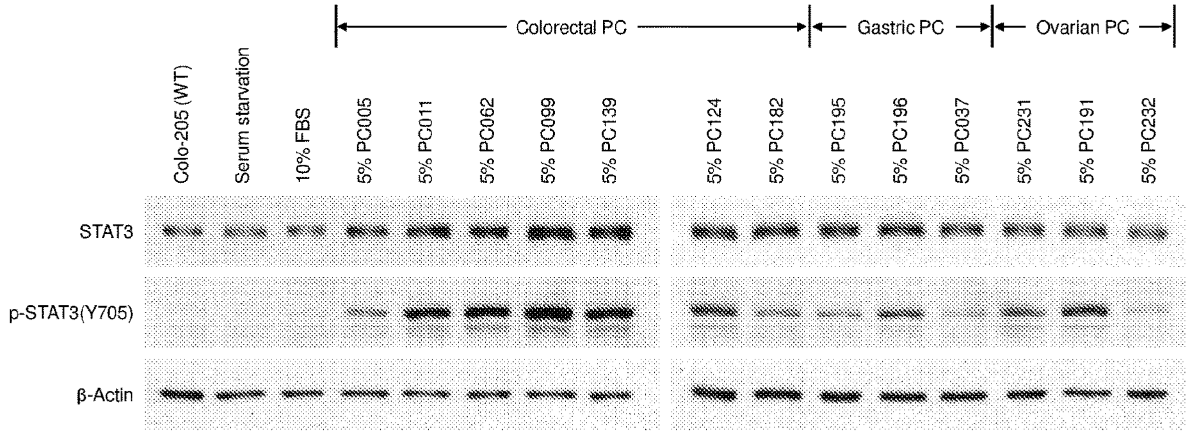

(A)

(B)

FIG. 6
(A)
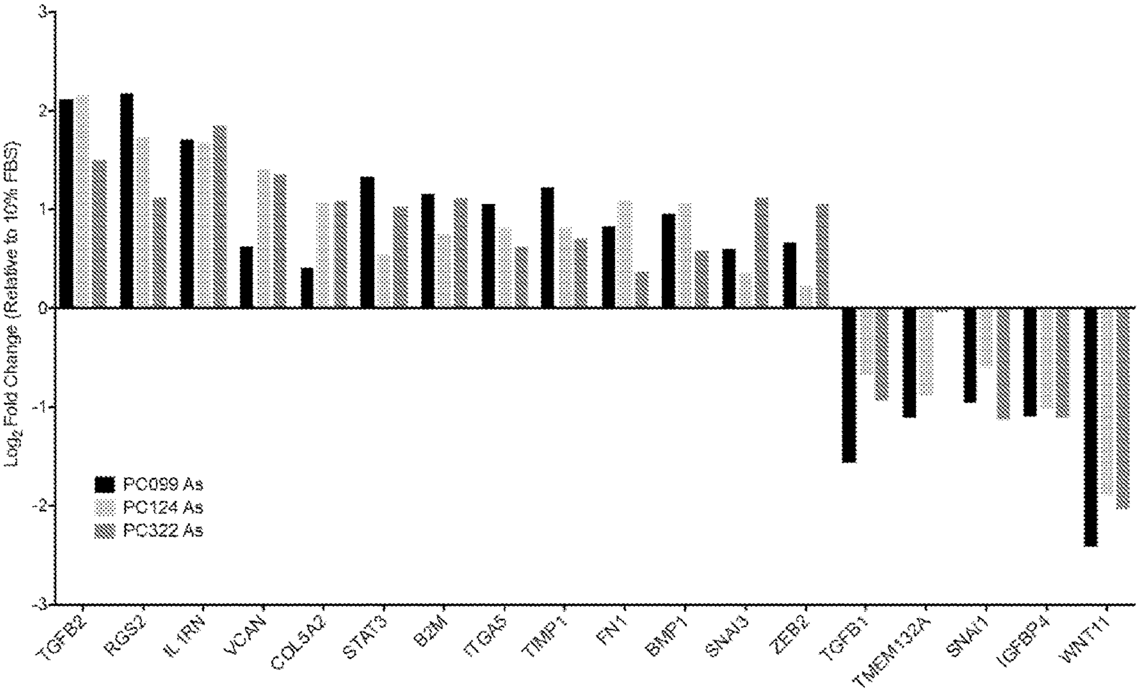
(B)
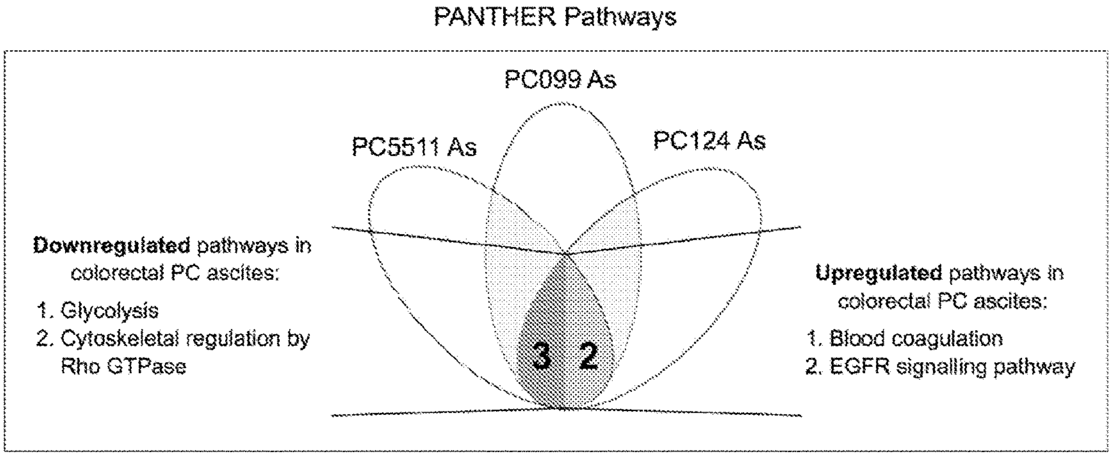

(C)

FIG. 7
(A)
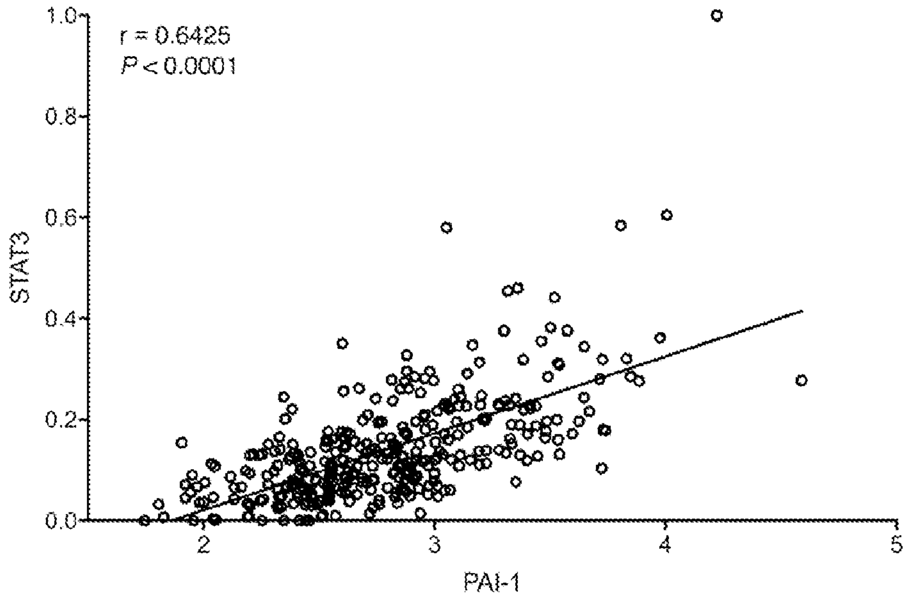
(B)
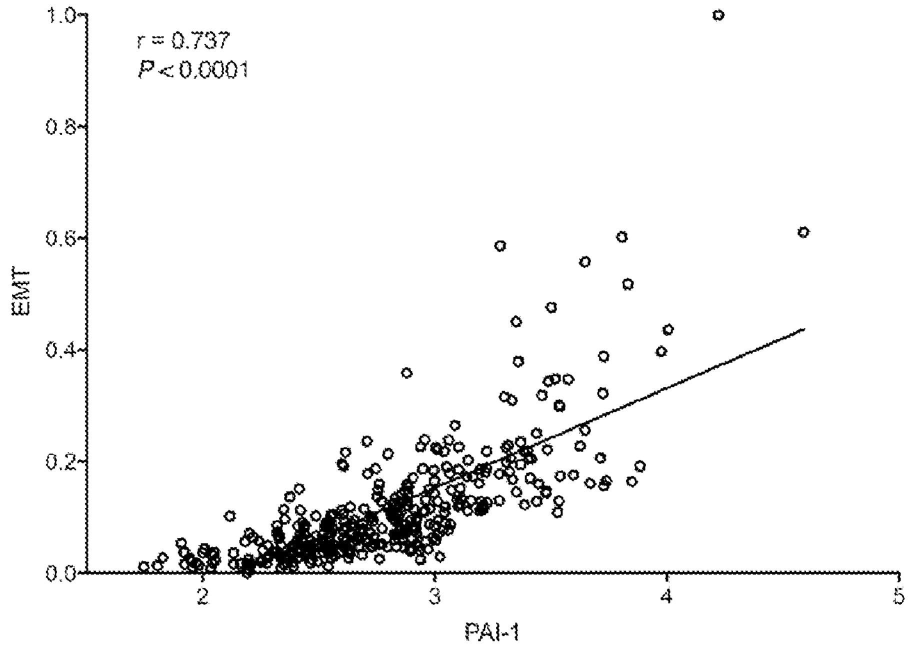

(C)

| No. at risk | | | | | | |
|---|---|---|---|---|---|---|
| P-S-E- | 95 | 82 | 57 | 36 | 25 | 17 |
| P-S+E- | 101 | 86 | 50 | 28 | 17 | 13 |
| P-S+E+ | 68 | 52 | 25 | 16 | 8 | 6 |
| P+S+E+ | 81 | 59 | 31 | 18 | 10 | 8 |

FIG. 8
(A)
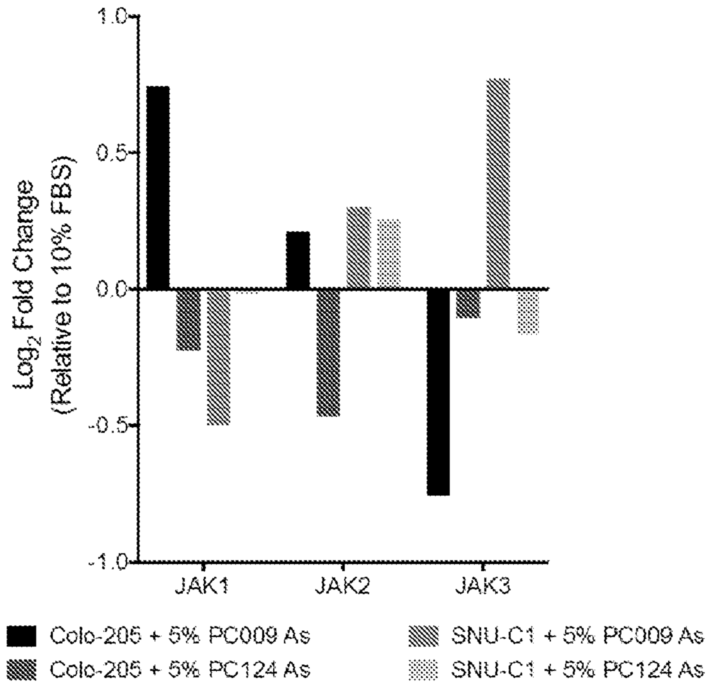
(B)
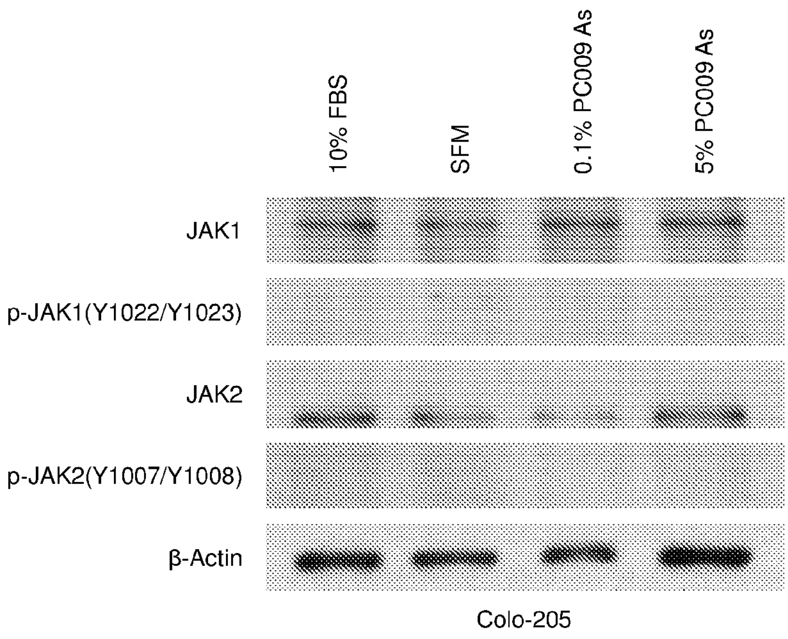

FIG. 9
(A)
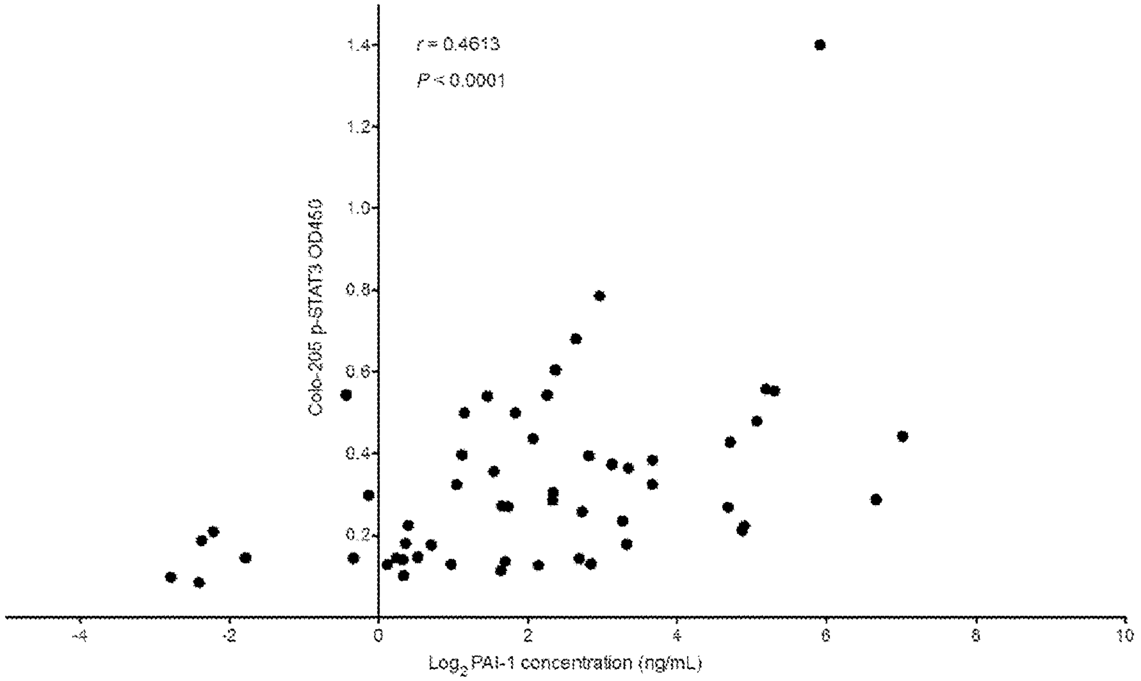
(B)
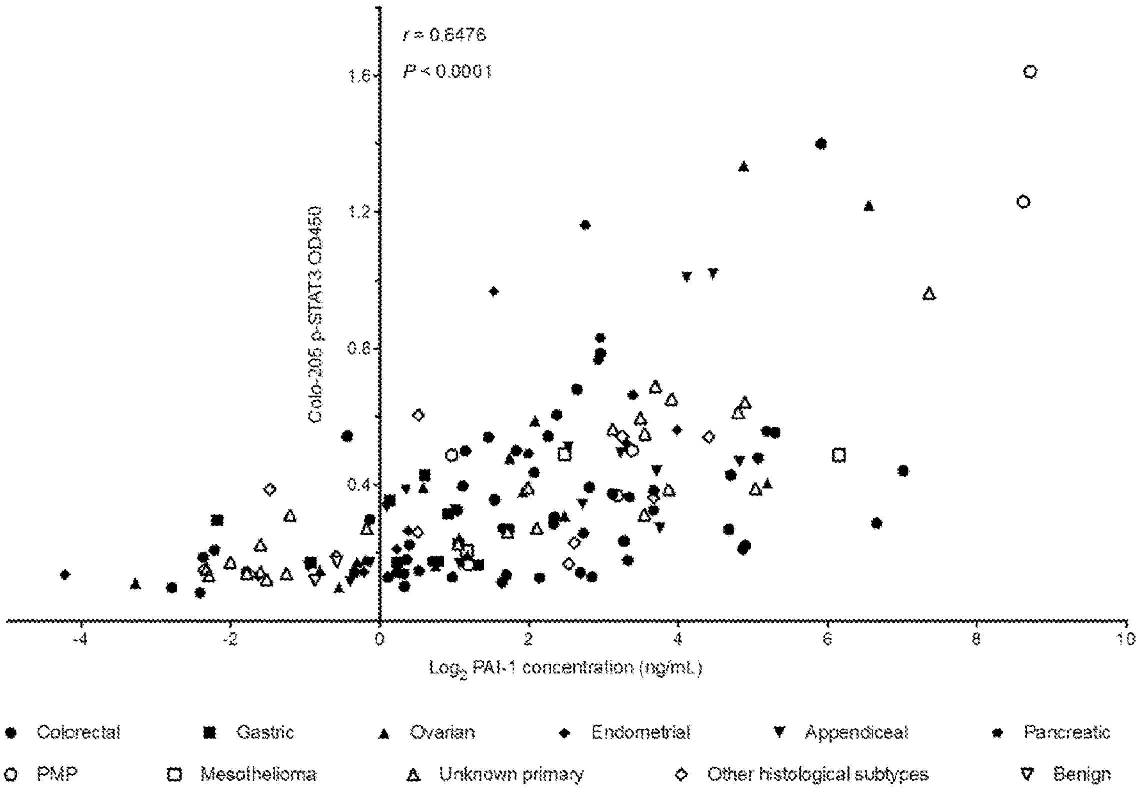

FIG. 10
(A)
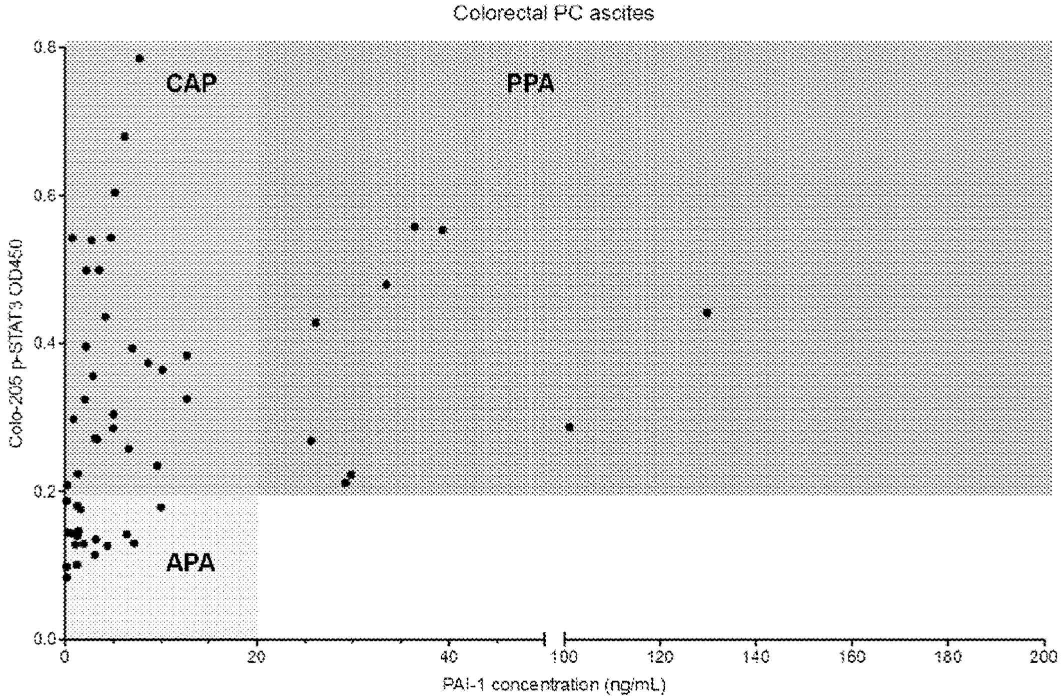
(B)
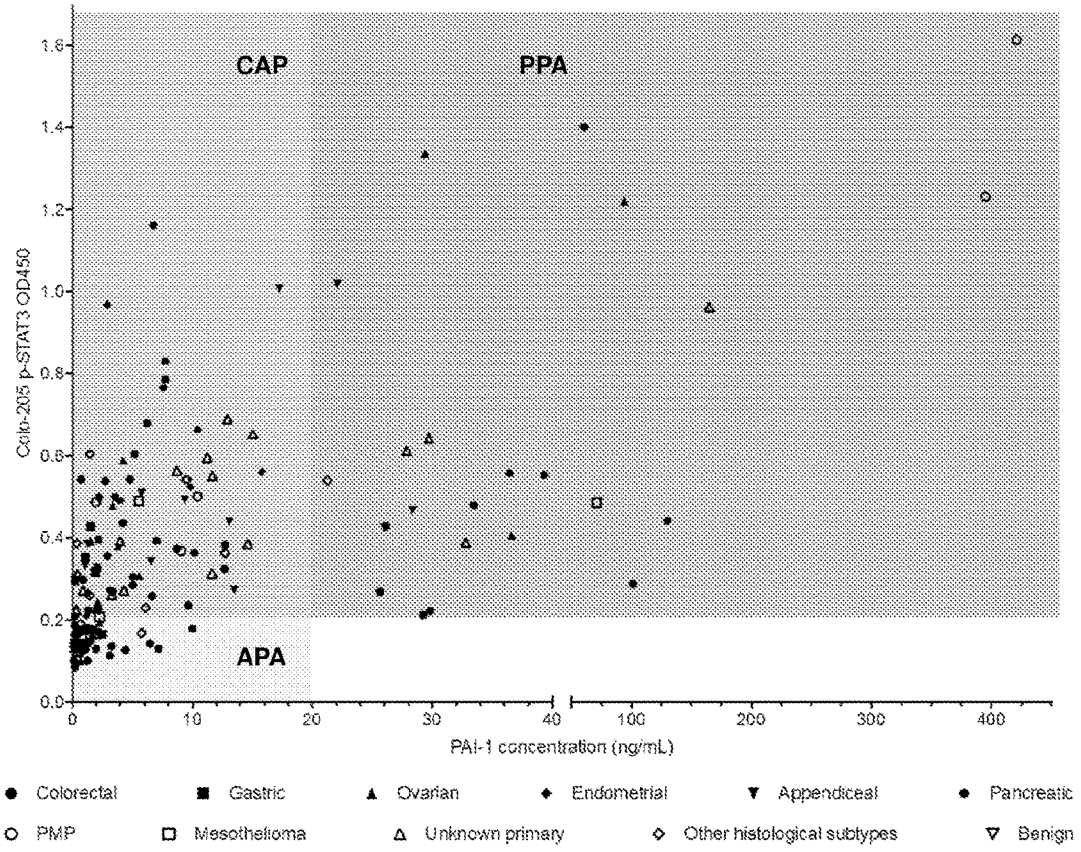

FIG. 10 continued (C)

| | PAI-1 concentration (ng/mL) | p-STAT3 (Y705) OD450 |
|---|---|---|
| Alternative pathways activation (APA) | < 20 | < 0.2 |
| Co-activators predominant (CAP) | < 20 | ≥ 0.2 |
| PAI-1 paracrine addiction (PPA) | ≥ 20 | ≥ 0.2 |

(D)

| Histology of PC subtypes | No. of samples |
|---|---|
| Colorectal | 55 |
| Gastric | 9 |
| Ovarian | 17 |
| Endometrial | 7 |
| Appendiceal | 17 |
| Pancreatic | 5 |
| Pseudomyxoma peritonei (PMP) | 6 |
| Mesothelioma | 3 |
| Unknown primary | 25 |
| Other PC histologies | |
| Lung | 2 |
| Breast | 2 |
| Primary peritoneal cancer | 2 |
| Gastric and ovarian (synchronous) | 1 |
| Small bowel | 1 |
| Urothelial | 1 |
| Palate | 1 |
| Benign | |
| Benign serous cystadenofibroma | 1 |
| Mucinous cyst adenoma | 1 |
| Total | 156 |

FIG. 11 continued

(C)

| Histology of PC subtypes | No. of samples |
|---|---|
| Colorectal | 32 |
| Gastric | 5 |
| Ovarian | 11 |
| Endometrial | 5 |
| Appendiceal | 12 |
| Pancreatic | 3 |
| Pseudomyxoma peritonei (PMP) | 4 |
| Mesothelioma | 3 |
| Unknown primary | 11 |
| Other PC histologies | |
| Lung | 1 |
| Breast | 2 |
| Primary peritoneal cancer | 1 |
| Gastric and ovarian (synchronous) | 1 |
| Small bowel | 1 |
| Urothelial | 1 |
| Palate | 1 |
| Total | 94 |

FIG. 12
(A)
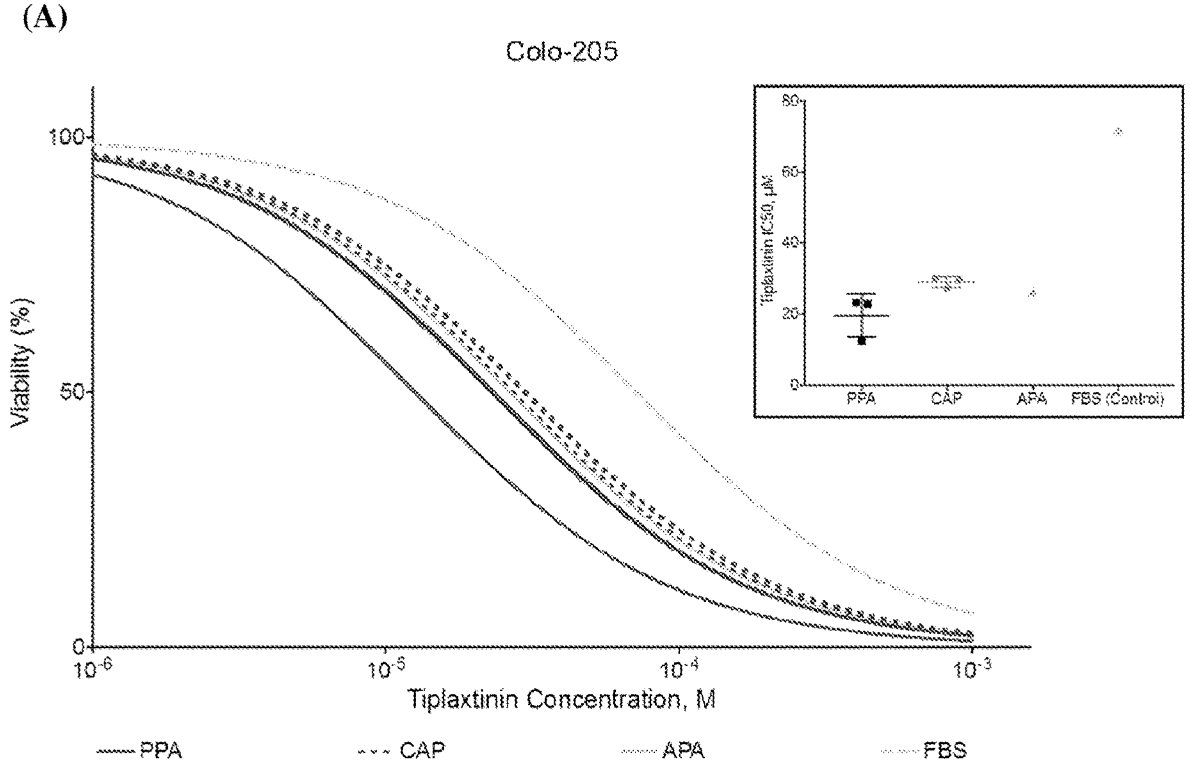
(B)
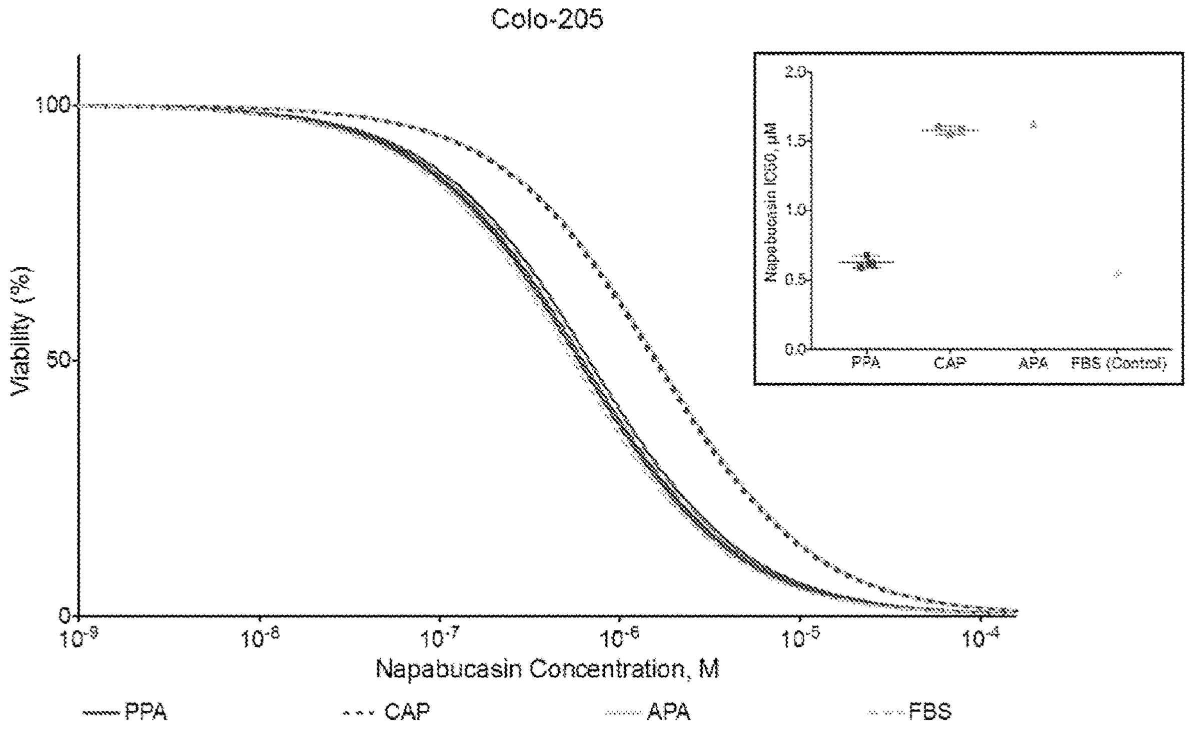

FIG. 12 continued
(C)
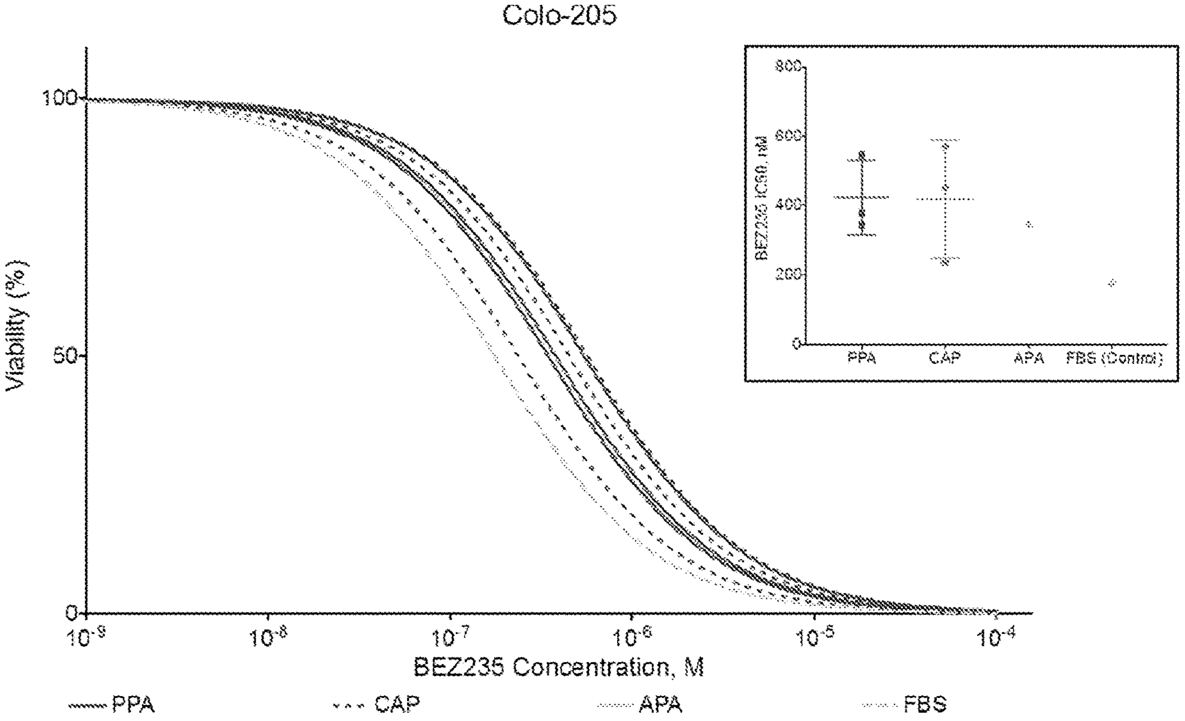
(D)
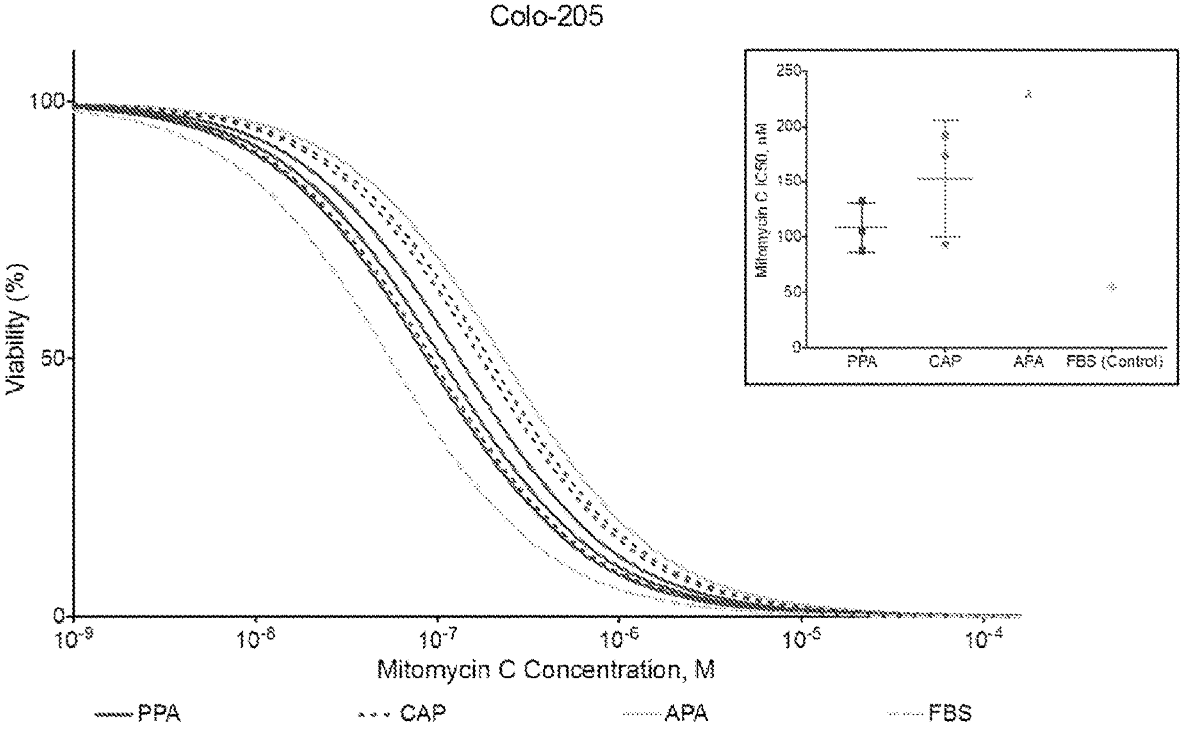

FIG. 13
(A)
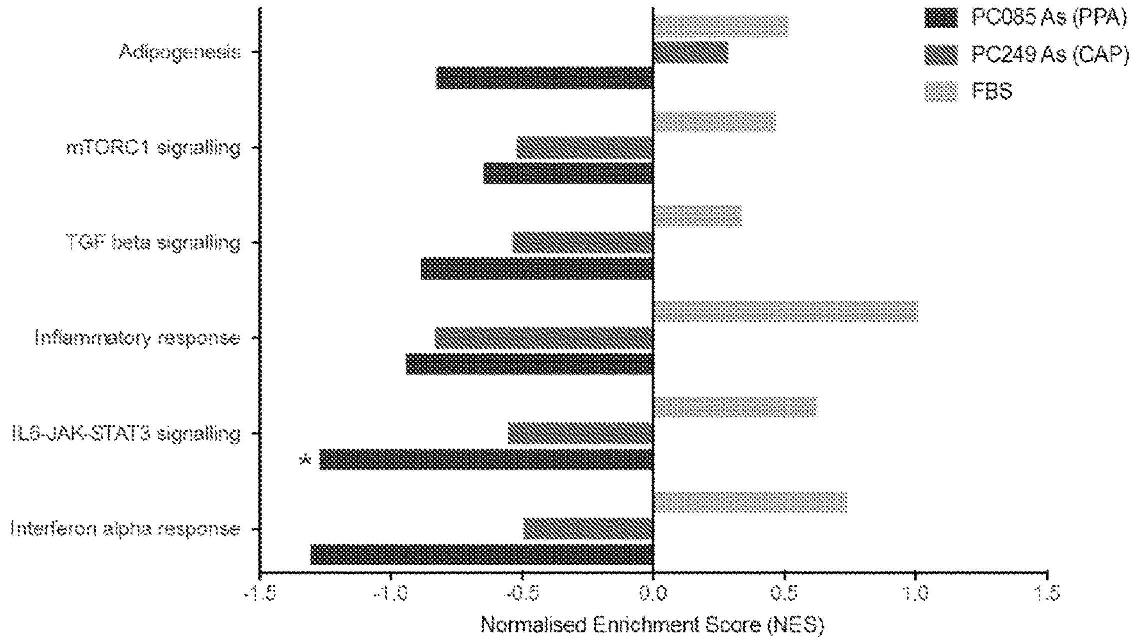
(B)
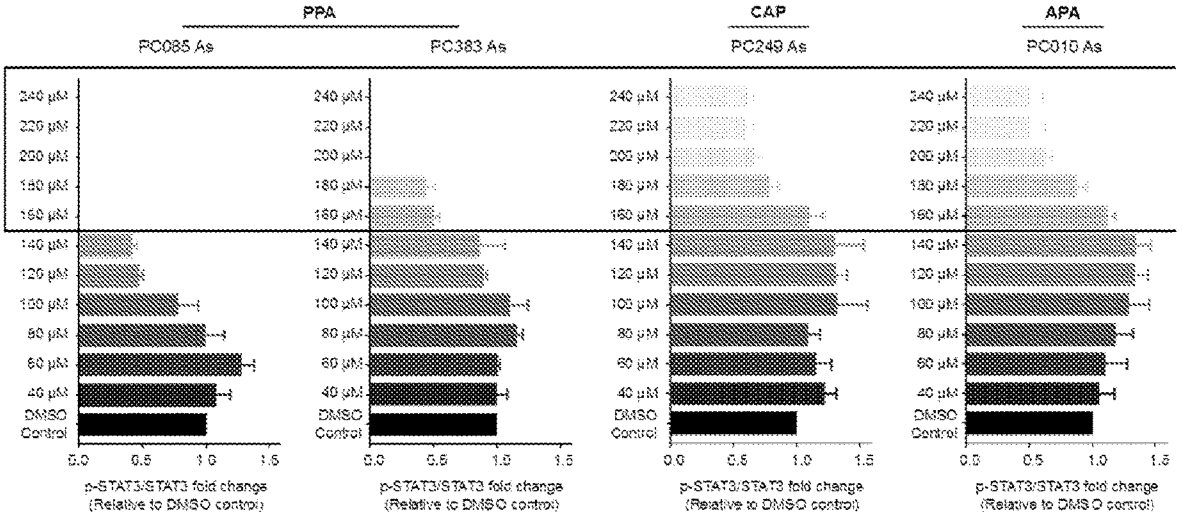

FIG. 14

(A)

Modified peritoneal cancer index (PCI)

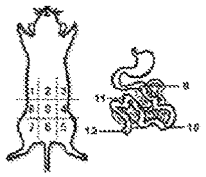

| PCI score | Tumour size |
|---|---|
| 0 | No visible macroscopic tumour |
| 1 | < 1 mm nodule |
| 2 | 1-5 mm nodule |
| 3 | > 5 mm tumour or ≥ 10 nodules in one region |

| Regions | | Organs |
|---|---|---|
| 0 | Central abdomen | Kidneys, pancreas, central peritoneum |
| 1 | Right upper | Right lobe of liver, right diaphragm, right upper peritoneum |
| 2 | Upper central | Median lobe of liver, upper central peritoneum |
| 3 | Left upper | Left lobe of liver, caudate lobe of liver, left diaphragm, left upper peritoneum |
| 4 | Left flank | Left ovary, spleen, left flank peritoneum |
| 5 | Left lower | Left lower peritoneum |
| 6 | Pelvis | Fallopian tubes, uterus, bladder, gonadal fat, pelvic peritoneum |
| 7 | Right lower | Right lower peritoneum |
| 8 | Right flank | Right ovary, right flank peritoneum |
| 9 | Upper GI/proximal jejunum | Stomach, duodenum, proximal jejunum and mesentery |
| 10 | Distal jejunum | Distal jejunum and mesentery |
| 11 | Ileum | Ileum and mesentery |
| 12 | Colon | Colon and rectum |

(B)

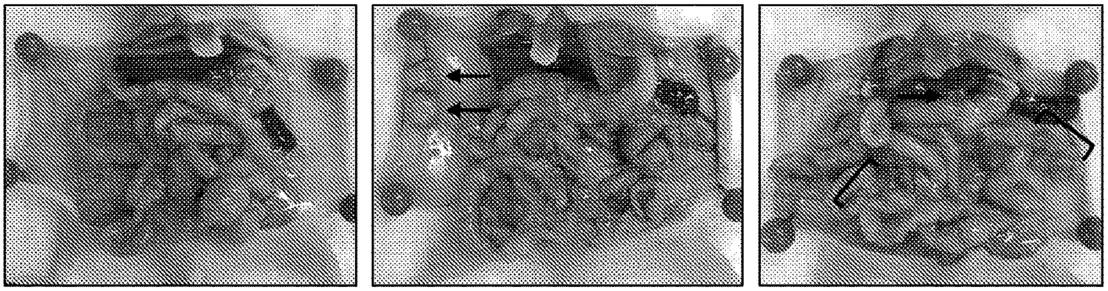

(C)

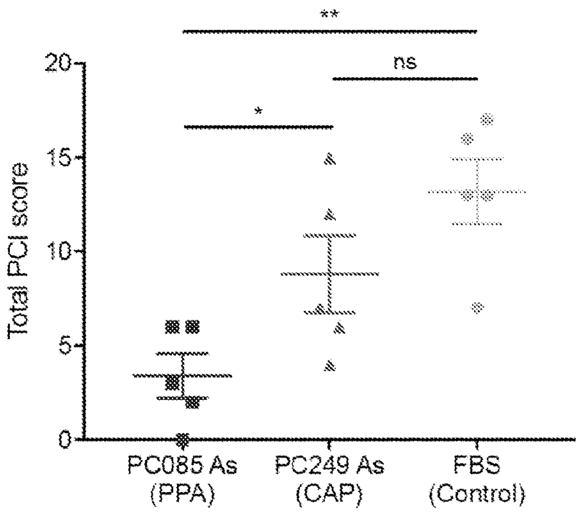

FIG. 15
(A)
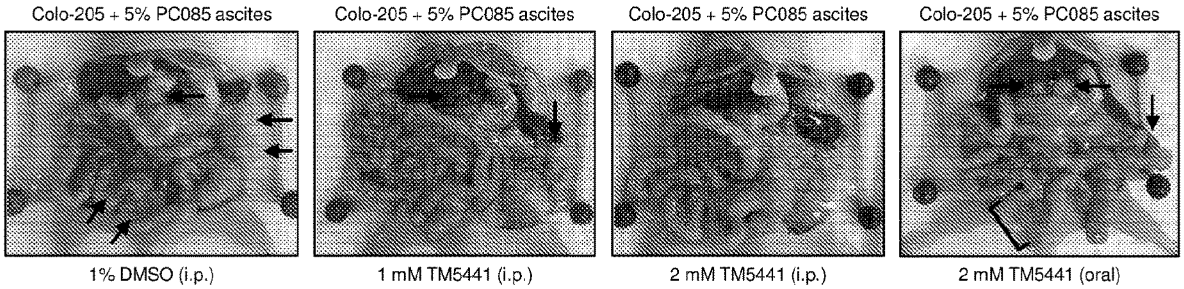
(B)
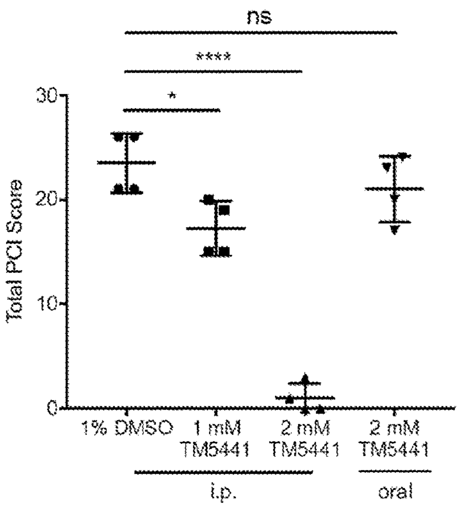

FIG. 16
(A)
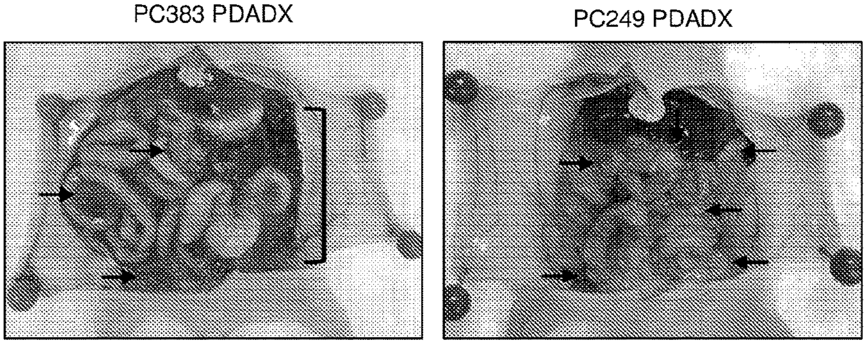
(B)
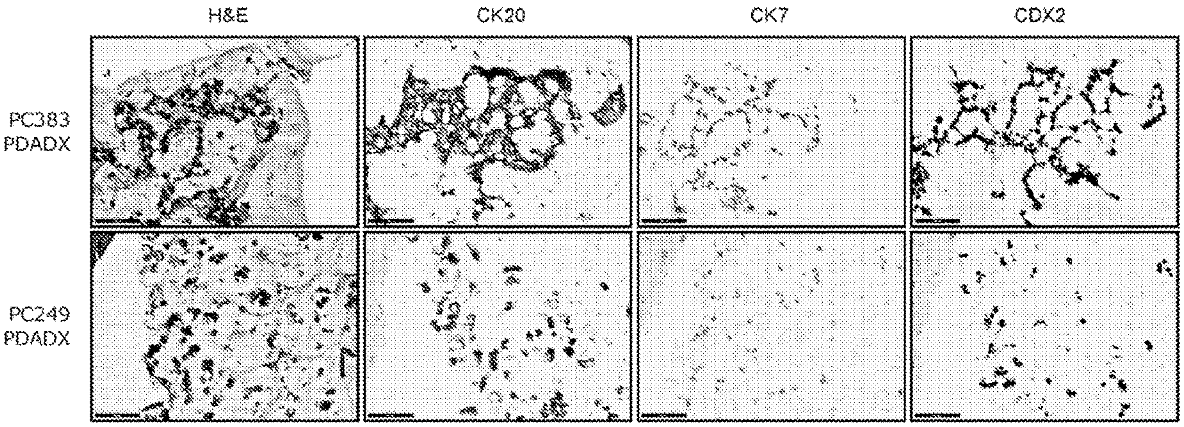

FIG. 17
(A)
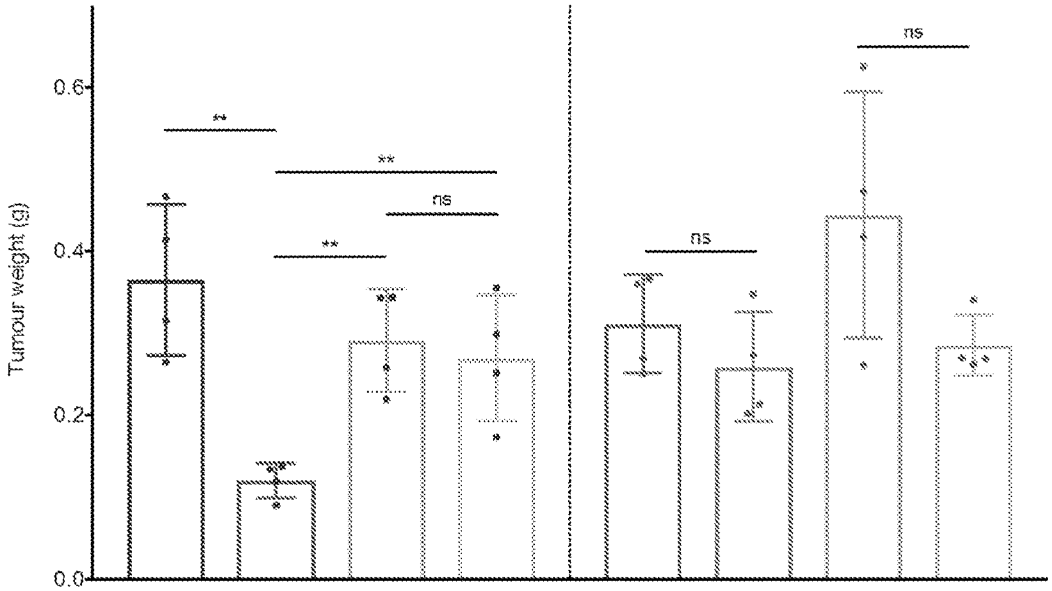
| Treatment | PC383 PDADX | | | | PC249 PDADX | | | |
|---|---|---|---|---|---|---|---|---|
| 5% PC383 As | + | + | - | - | - | - | - | - |
| 5% PC249 As | - | - | - | - | + | + | - | - |
| 10% FBS | - | - | + | + | - | - | + | + |
| 1% DMSO | + | + | + | + | + | + | + | + |
| 2 mM TM5441 | - | + | - | + | - | + | - | + |
(B)
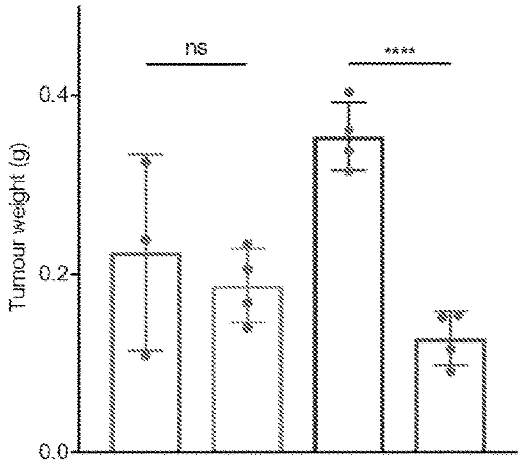
| Treatment | PC249 PDADX | | | |
|---|---|---|---|---|
| 5% PC249 As | + | + | - | - |
| 5% PC383 As | - | - | + | + |
| 1% DMSO | + | + | + | + |
| 2 mM TM5441 | - | + | - | + |

FIG. 19

(A)

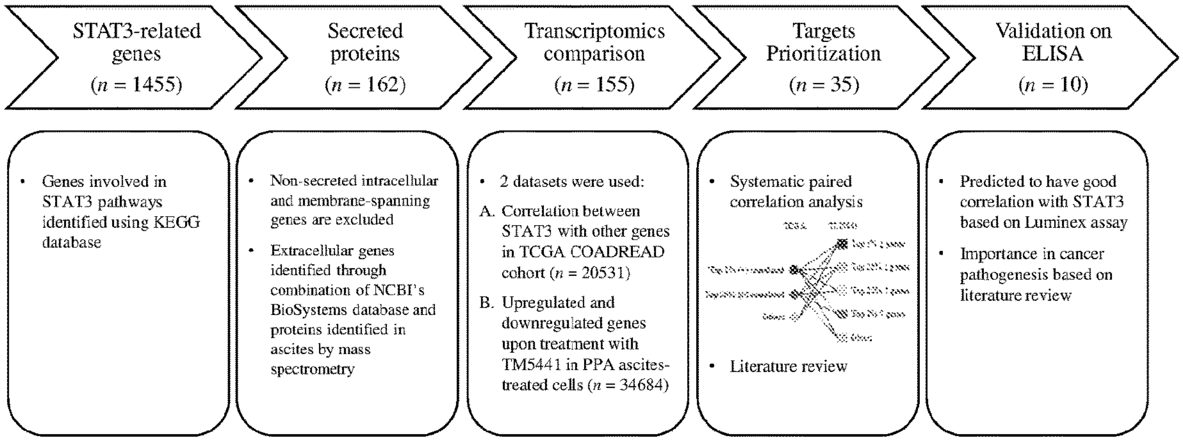

(B)

| Priority list | TCGA COADREAD | TM5441 Microarray | No. of genes | Chosen | Gene names of selected candidates |
|---|---|---|---|---|---|
| 1 | Top 1% (+) correlated with STAT3 | Top 1% downregulated | 0 | 0 | - |
| 2 | Top 1% (+) correlated with STAT3 | Top 1% upregulated | 1 | 1 | LUM |
| 3 | Top 25% (+) correlated with STAT3 | Top 1% downregulated | 2 | 2 | **ANGPT1**, IL1B |
| 4 | Top 25% (+) correlated with STAT3 | Top 1% upregulated | 0 | 0 | - |
| 5 | Top 1% (+) correlated with STAT3 | Top 25% downregulated | 4 | 2 | **POSTN**, TNC |
| 6 | Top 1% (+) correlated with STAT3 | Top 25% upregulated | 8 | 4 | **MMP9**, MMP2, TIMP3, DCN |
| 7 | Top 25% (+) correlated with STAT3 | Top 25% downregulated | 15 | 5 | **VSIG4**, CXCL5, CD36, ANGPT2, SERPINB5 |
| 8 | Top 25% (+) correlated with STAT3 | Top 25% upregulated | 19 | 6 | **IL6**, **CCL2**, LEP, VCAM1, CCL8, ITGAM |
| 9 | Top 1% (+) correlated with STAT3 | Others | 16 | 5 | THBS1, FN1, COL5A1, MXRA5, C3 |
| 10 | Top 25% (+) correlated with STAT3 | Others | 46 | 7 | **CXCL10**, **TGFB1**, **CD44**, TIM3, TNFSF13B, CEACAM1, LAMB1 |
| 11 | Others | Top 1% downregulated | 0 | 0 | - |
| 12 | Others | Top 25% downregulated | 15 | 3 | **IL10**, IL5, IL22 |
| 13 | Others | Top 25% upregulated | 19 | 0 | - |
| 14 | Others | Others | 2 | 0 | - |
| 15 | Top 25% (-) correlated with STAT3 | Others | 7 | 0 | - |
| 16 | Top 25% (-) correlated with STAT3 | Top 25% upregulated | 1 | 0 | - |
| | | **Total** | 155 | 35 | |

FIG. 20 continued (C)

| Biomarkers | IL-6 concentration | IL-10 concentration | CCL-2 concentration | MMP-9 concentration |
|---|---|---|---|---|
| Cut-off values for PPA/CAP | ≥ 997 pg/mL | ≥ 15 pg/mL | ≥ 450 pg/mL | ≥ 3 ng/mL |
| Cut-off values for APA | < 997 pg/mL | < 15 pg/mL | < 450 pg/mL | < 3 ng/mL |

(D)

| No. of biomarker | p-STAT3 surrogate biomarker | APA Accuracy | PPA/CAP Accuracy | Overall Accuracy | Cut-off (PPA/CAP) | Cut-off (APA) |
|---|---|---|---|---|---|---|
| 1 | IL6 | 80% | 95% | 92.86% | | |
| | IL10 | 60% | 88.33% | 84.29% | | |
| | CCL2 | 30% | 95% | 85.71% | | |
| | MMP9 | 70% | 48.33% | 51.43% | | |
| 2 | IL6, IL10 | 100% | 86.67% | 88.57% | 2 (+) biomarkers | 0 or 1 (+) biomarker |
| | IL6, CCL2 | 90% | 91.67% | 91.43% | | |
| | IL10, CCL2 | 70% | 85% | 82.86% | | |
| | IL6, MMP9 | 50% | 98.33% | 91.43% | 1 or 2 (+) biomarkers | 0 (+) biomarker |
| | IL10, MMP9 | 50% | 95% | 88.57% | | |
| | CCL2, MMP9 | 20% | 100% | 88.57% | | |
| 3 | IL6, IL10, CCL2 | 60% | 96.67% | 91.43% | 2 or 3 (+) biomarkers | 0 or 1 (+) biomarker |
| | IL6, IL10, MMP9 | 80% | 93.33% | 91.43% | | |
| | IL6, CCL2, MMP9 | 70% | 96.67% | 92.86% | | |
| | IL10, CCL2, MMP9 | 50% | 93.33% | 87.14% | | |
| 4 | IL6, IL10, CCL2, MMP9 | 90% | 93.33% | 92.86% | 3 or 4 (+) biomarkers | 0, or 1, or 2 (+) biomarker |

(E)

| Biomarkers | PAI-1 concentration | p-STAT3 (Y705) OD450 | IL-6 concentration | IL-10 concentration | CCL-2 concentration | MMP-9 concentration |
|---|---|---|---|---|---|---|
| Cut-off values | 20 ng/mL | 0.2 | 997 pg/mL | 15 pg/mL | 450 pg/mL | 3 ng/mL |
| Range | ± 5% | | | | | |

(A)

(B)

FIG. 21 continued
(C)
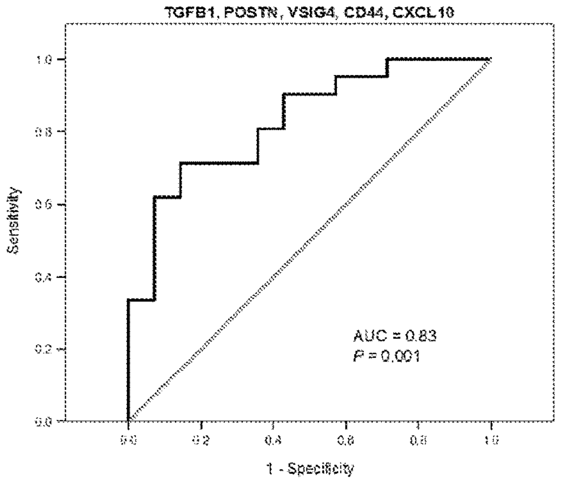
(D)
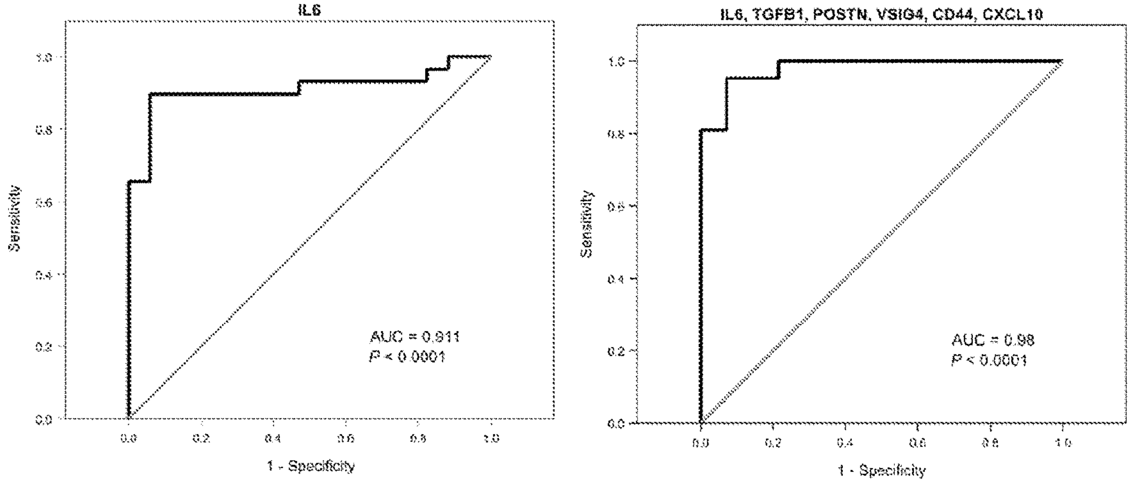
(E)
| No. of biomarker | p-STAT3 surrogate biomarker | AUC | *P*-value |
|---|---|---|---|
| 1 | TGFB1 | 0.720 | 0.018 |
| | POSTN | 0.766 | 0.005 |
| | VSIG4 | 0.719 | 0.020 |
| | CD44 | 0.579 | 0.393 |
| | CXCL10 | 0.552 | 0.577 |
| | IL6 | 0.911 | < 0.0001 |
| 5 | TGFB1, POSTN, VSIG4, CD44, CXCL10 | 0.830 | 0.001 |
| 6 | IL6, TGFB1, POSTN, VSIG4, CD44, CXCL10 | 0.980 | < 0.0001 |

BIOMARKER WITH THERAPEUTIC IMPLICATIONS FOR PERITONEAL CARCINOMATOSIS

CROSS-REFERENCE TO RELATED APPLICATIONS

This is a U.S. National Phase Application of International Application No. PCT/SG2020/050177, filed Mar. 27, 2020, which claims the benefit of priority of Singapore provisional application No. 10201902763U, filed Mar. 27, 2019. The contents of both applications are hereby incorporated by reference in their entireties.

FIELD OF THE INVENTION

The present invention relates generally to the field of molecular biology. In particular, the present invention relates to the use of biomarkers for the detection, diagnosis and subsequent treatment of cancer.

BACKGROUND OF THE INVENTION

Colorectal cancer is the third most common cancer and the fourth most common cause of cancer death globally, accounting for 1.4 million new cases and 600,000 deaths per year. Deaths from colorectal cancer are largely due to metastasis with peritoneal carcinomatosis (PC) occurring in 15% of all patients and accounting for up to 30% of all metastases. Compared to other forms of metastatic colorectal cancer without peritoneal involvement, colorectal peritoneal carcinomatosis has consistently demonstrated to have significantly shorter overall survival despite palliative systemic chemotherapy.

Cytoreductive surgery (CRS) and hyperthermic intraperitoneal chemotherapy (HIPEC) have revolutionised the treatment of peritoneal carcinomatosis. Cytoreductive surgery refers to a series of visceral resections and peritonectomy procedures that remove all macroscopic disease. Remaining viable microscopic disease is then eradicated with the instillation of hyperthermic intraperitoneal chemotherapy. The combined treatment modalities of cytoreductive surgery and hyperthermic intraperitoneal chemotherapy have greatly improved survival in patients with peritoneal carcinomatosis of colorectal origin. The median survival of patients treated with cytoreductive surgery and hyperthermic intraperitoneal chemotherapy was 33 months, compared to 6 to 12 months in patients treated with systemic chemotherapy alone. However, despite this dramatic improvement, much more needs to be done to further improve the outcome of treatment for patients with colorectal peritoneal carcinomatosis by improving the hyperthermic intraperitoneal chemotherapy regimen, as surgery is unlikely to improve patient outcome further.

Hence, there is a need for improved patient stratification in order to improve treatment.

SUMMARY

In one aspect, the present disclosure refers to a method of treating a subject suffering from peritoneal carcinomatosis with a "plasminogen activator inhibitor 1" (PAI-1) inhibitor, the method comprising determining the concentration of PAI-1 and determining the level of phosphorylation of "signal transducer and activator of transcript 3" (STAT3) in a sample obtained from the subject; administering the PAI-1 inhibitor to the subject showing (a) an increase in PAI-1 concentration and an increase in STAT3 phosphorylation, or (b) a decrease in PAI 1 concentration and an increase in STAT3 phosphorylation; wherein the increase and/or decrease of the concentration of PAI-1 and STAT3 phosphorylation is compared to a reference value.

In another aspect, the present disclosure refers to a method of detecting or determining susceptibility of a subject suffering from peritoneal carcinomatosis to a treatment with a "plasminogen activator inhibitor 1" (PAI-1) inhibitor, the method comprising determining the concentration of PAI-1 and determining the level of phosphorylation of "signal transducer and activator of transcript 3" (STAT3) in a sample obtained from a subject; wherein the subject is susceptible to the treatment if the subject shows (a) an increase in PAI 1 concentration and an increase in STAT3 phosphorylation, or (b) a decrease in PAI 1 concentration and an increase in STAT3 phosphorylation; wherein the subject is not considered to be susceptible to treatment if the subject shows (c) a decrease in PAI-1 concentration and a decrease in STAT3 phosphorylation; wherein the increase and/or decrease of the concentration of PAI-1 and the level of STAT3 phosphorylation is compared to a reference value.

In one aspect, the present disclosure refers to a panel of markers for treating a patient suffering from peritoneal carcinomatosis with a "plasminogen activator inhibitor 1" (PAI-1) inhibitor, or for detecting or determining susceptibility of a subject suffering from peritoneal carcinomatosis to a treatment with a "plasminogen activator inhibitor 1" (PAI-1) inhibitor, wherein the panel of markers comprises PAI-1, and one or more surrogate markers of STAT3 phosphorylation, or p-STAT3.

In another aspect, the present disclosure refers to the use of a panel of markers in the method of disclosed herein, wherein the panel comprises PAI-1 and one or more surrogate markers of STAT3 phosphorylation, or PAI-1 and p-STAT3.

BRIEF DESCRIPTION OF THE DRAWINGS

The invention will be better understood with reference to the detailed description when considered in conjunction with the non-limiting examples and the accompanying drawings, in which:

FIG. 4(A) Treatment with 5% cell-free ascites activated STAT3 via phosphorylation at Tyr705. (B) Treatment of 5% cell-free ascites of various histological peritoneal carcinomatosis (PC) subtypes resulted in activation of STAT3, where cell-free ascites of colorectal origin showed the most activation.

FIG. 8(A) Receptor Tyrosine Kinase (RTK) phosphorylation array performed on colorectal peritoneal carcinomatosis (PC) cell lines treated with cell-free ascites revealed no activation of JAKs, suggesting non-canonical mechanism of STAT3 activation. (B) Western blot validation showing JAKs are inactive in cell-free ascites-treated cells.

FIG. 9 shows results of a screen which was conducted on (A) cell-free ascites from colorectal peritoneal carcinomatosis (PC) (n=55) and (B) cell-free ascites from various histological peritoneal carcinomatosis (PC) subtypes (n=156) using ELISA. Levels of PAI-1 in ascites and cancer cells p-STAT3 (Y705) levels upon treatment with cell-free ascites were measured and plotted to determine their association. PAI-1 concentrations are plotted on a $\log_2$ scale. p-STAT3 (Y705) levels are shown as optical density reading at 450 nm (OD450). Correlation analyses were determined by Pearson correlation coefficient test.

FIG. 10 Untransformed values of PAI-1 and p-STAT3 (Y705) levels were used for gating strategy to identify patient subpopulations which might benefit from PAI-1 inhibition. Three distinct groups of patients can be observed—patients who had high PAI-1 levels and high STAT3 activation, termed PAI-1 paracrine addicted or PPA (right upper quadrant), patients with low PAI-1 levels but high STAT3 activation, termed co-activators predominant or CAP (left upper quadrant), and patients with low PAI-1 levels and low STAT3 activation, termed alternative pathways activation or APA (left lower quadrant). (A) PAI-1 and p-STAT3 gating of colorectal peritoneal carcinomatosis (PC) cell-free ascites. (B) PAI-1 and p-STAT3 gating of various histological peritoneal carcinomatosis (PC) subtypes cell-free ascites. (C) PAI-1 and p-STAT3 cut-off values used to stratify patients into the three distinct groups. (D) Cohort of cell-free ascites used in this analysis.

FIG. 12 shows the effect of various pharmacological inhibitions on the three distinct groups of cell-free ascites-treated Colo-205 cells. Representative inhibitor dose-response curves of PAI-1 paracrine addicted (PPA) group (black solid line), co-activators predominant (CAP) group (black dotted line), alternative pathways activation (APA) group (grey solid line), and foetal bovine serum (FBS; control, grey dotted line). Corresponding $IC_{50}$ values are shown in inset, mean±s.d. (A) Tiplaxtinin (PAI-1 inhibitor) dose-response curve, (B) Napabucasin (STAT3 inhibitor) dose-response curve, (C) BEZ235 (dual PI3K/mTOR inhibitor) dose-response curve, and (D) Mitomycin C (conventional chemotherapeutic agent used in hyperthermic intraperitoneal chemotherapy (HIPEC)—DNA crosslinker) dose-response curve. Targeting PAI-1, a dominant paracrine factor in cell-free ascites, was shown to be more effective than targeting downstream signalling pathway activated by cell-free ascites, proliferation pathway, or DNA synthesis.

FIG. 13(A) Signalling pathways affected by PAI-1 inhibition were identified by RNA microarray analysis of cancer cells treated with cell-free ascites representative of PAI-1 paracrine addicted (PPA) (PC085), co-activators predominant (CAP) (PC249) or foetal bovine serum (FBS; control) in the presence of TM5441 or DMSO vehicle. IL6-JAK-STAT3 signalling pathway was significantly downregulated in PAI-1 paracrine addicted (PPA)-treated cells upon PAI-1 inhibition. Normalised enrichment scores less than 0 indicate pathway suppression and scores greater than 0 indicate pathway activation. (B) Treatment of cancer cells with PAI-1 paracrine addicted (PPA) cell-free ascites (PC085 and PC383), co-activators predominant (CAP) cell-free ascites (PC249) and alternative pathways activation (APA) cell-free ascites (PC010) in the presence of various concentrations of TM5441 or DMSO vehicle measured by ELISA confirmed that cells exposed to PAI-1 paracrine addicted (PPA) cell-free ascites relied on PAI-1 to activate STAT3 as they required a lower concentration of TM5441 to suppress STAT3 activation.

FIG. 14(A) Schematic of modified peritoneal cancer index (PCI), used to assess tumour burden in peritoneal carcinomatosis (PC) cell line mouse model. This scoring system is a modification of peritoneal carcinomatosis index (PCI) scoring from Klaver et al. (Klaver Y. L. B., Hendriks T., Lomme R. M. L. M., Rutten H. J. T., Bleichrodt R. P., de Hingh I. H. J. T. (2010) Intraoperative hyperthermic intraperitoneal chemotherapy after cytoreductive surgery for peritoneal carcinomatosis in an experimental model. *British Journal of Surgery*. 97: 1874-80) and Sugarbaker (Sugarbaker P. H. (1998) Intraperitoneal chemotherapy and cytoreductive surgery for the prevention and treatment of peritoneal carcinomatosis and sarcomatosis. *Seminars in Surgical Oncology*. 14: 254-61).

Figure 1:
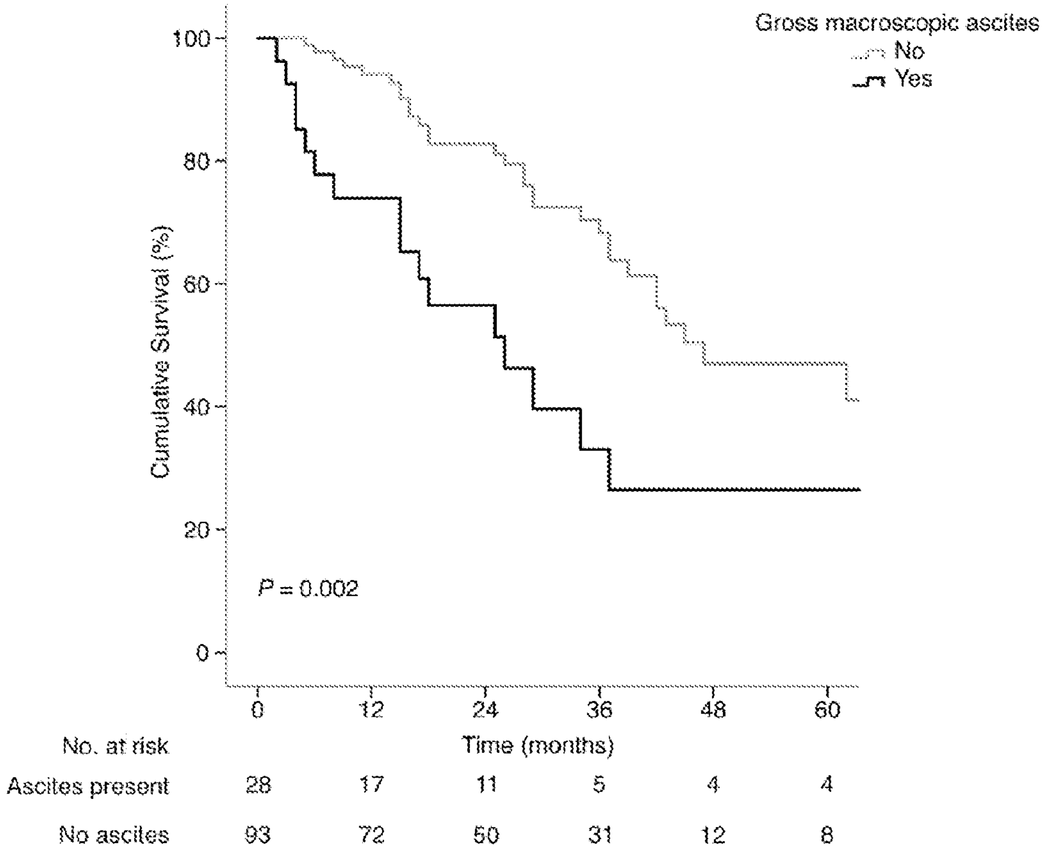
FIG. 1 shows data indicating that the presence of ascites leads to a poorer prognosis in patients regardless of histological subtype. (A) Kaplan-Meier survival curve of all patients with peritoneal carcinomatosis (P=0.002). (B) Kaplan-Meier survival curve of colorectal patients with peritoneal carcinomatosis (P=0.001). (C) Kaplan-Meier survival curve of ovarian patients with peritoneal carcinomatosis (P=0.077).
Figure 1:
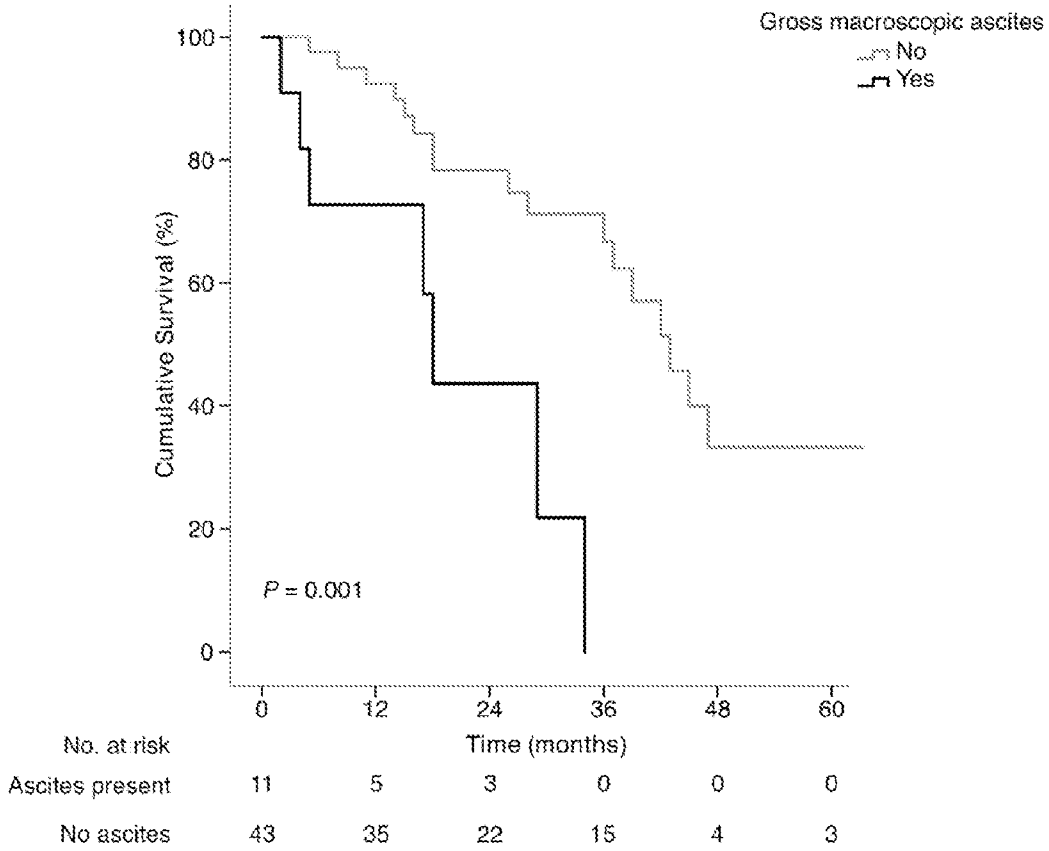
Figure 1:
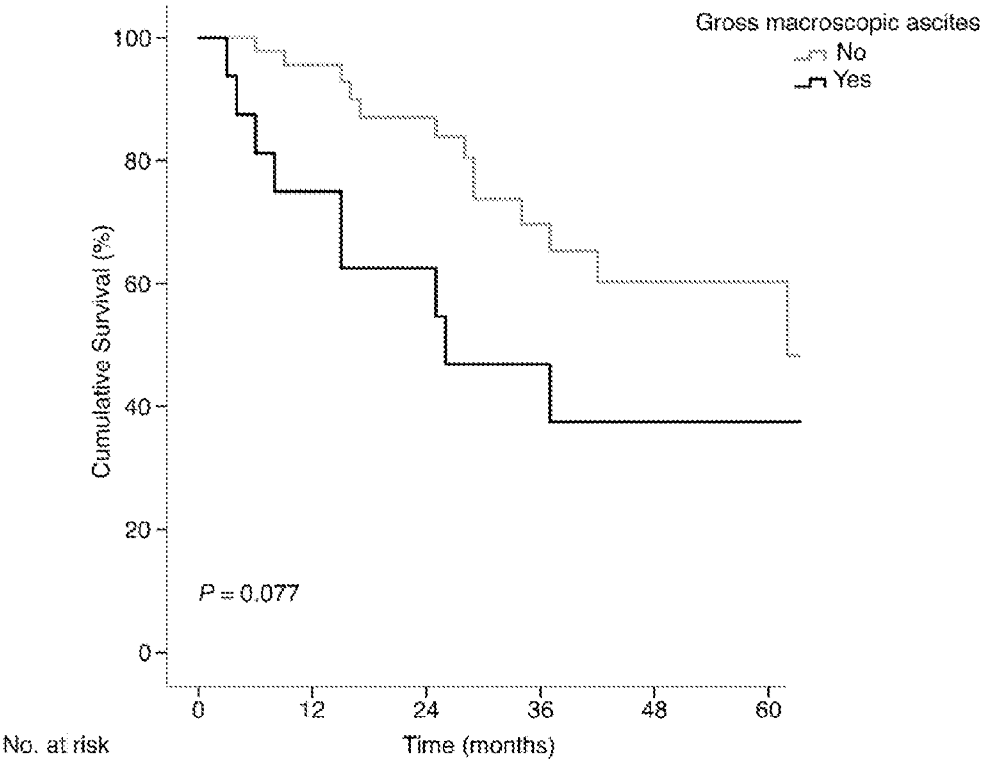

(B) In vivo validation of differential sensitivity to PAI-1 inhibition in peritoneal carcinomatosis (PC) cell line mouse model treated with PAI-1 paracrine addicted (PPA) cell-free ascites (PC085), co-activators predominant (CAP) cell-free ascites (PC249) and foetal bovine serum (FBS; control). Images shown are representative of peritoneal metastases formed in response to PAI-1 inhibition or vehicle. Arrows indicate visible tumours. (C) Tumour burden was assessed by modified peritoneal carcinomatosis index (PCI) score. Mice treated with PAI-1 paracrine addicted (PPA) cell-free ascites had significant reduction in tumour burden in response to TM5441 compared to mice treated with co-activators predominant (CAP) cell-free ascites (PC249) and foetal bovine serum (n=5 mice/group).

FIG. 15 shows formation of peritoneal tumours in peritoneal carcinomatosis (PC) cell line mouse model exposed to PAI-1 paracrine addicted (PPA) cell-free ascites (PC085) effectively inhibited by intraperitoneal (i.p.) instillation of TM5441, but not when taken orally (n=4 mice/group).

FIG. 16 Matched patient's cell-free ascites and its cellular components were used to generate patient-derived ascites-dependent xenograft (PDADX). (A) Representative images of intraperitoneal tumours formed in PC383 patient-derived ascites-dependent xenograft (PDADX) and PC249 patient-derived ascites-dependent xenograft (PDADX) models. Arrows indicate visible tumours. (B) Representative haematoxylin and eosin (H & E) staining and immunohistochemical analyses reveal patient-derived ascites-dependent xenograft (PDADX) tumours with similar histological features as corresponding patients' tumour tissues, and that these patient-derived ascites-dependent xenograft (PDADX) tumours are of colonic origin (CK20+ CK7− CDX2+). Scale bar, 50 μM.

FIG. 17 shows PAI-1 inhibition is highly efficacious in in vivo mouse models that are addicted to PAI-1 paracrine addicted (PPA) cell-free ascites. (A) PAI-1 paracrine addicted (PPA) patient-derived ascites-dependent xenografts (PDADX) (PC383) and co-activators predominant (CAP) patient-derived ascites-dependent xenograft (PDADX) (PC249) were treated with its matched cell-free ascites or foetal bovine serum (FBS) in the presence of DMSO vehicle or 2 mM TM5441 (n=4 mice/group). Tumour burden was quantified by weighing all visible tumours after mice were sacrificed. Only PAI-1 paracrine addicted (PPA) patient-derived ascites-dependent xenograft (PDADX) treated with matched PAI-1 paracrine addicted (PPA) cell-free ascites was susceptible to PAI-1 inhibition and demonstrated significant reduction in tumour burden. (B) Co-activators predominant (CAP) patient-derived ascites-dependent xenograft (PDADX) (PC249) were treated with its matched cell-free ascites or PAI-1 paracrine addicted (PPA) cell-free ascites (PC383) in the presence of DMSO vehicle or 2 mM TM5441 (n=4 mice/group, except in group treated with PC249 cell-free ascites and DMSO (n=3). Co-activators predominant (CAP) patient-derived ascites-dependent xenograft (PDADX) exposed to PAI-1 paracrine addicted (PPA) cell-free ascites became susceptible to PAI-1 inhibition despite not being susceptible in the presence of its matched ascites.

Figure 18:
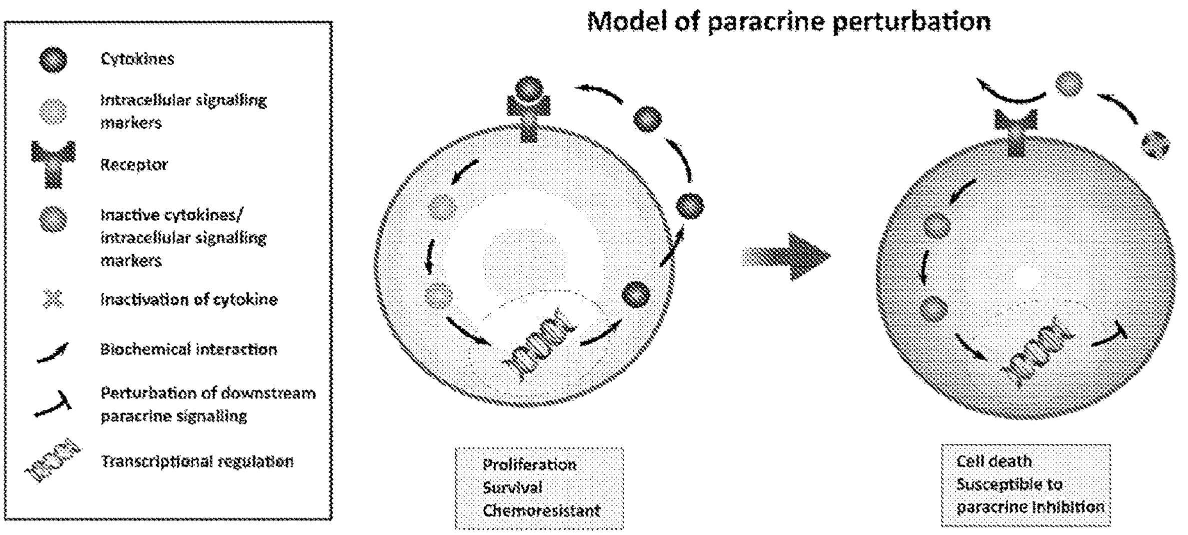

FIG. 18 shows a proposed model of paracrine perturbation that can be harnessed for novel therapeutic strategy in peritoneal carcinomatosis (PC).

FIG. 19(A) Workflow to select p-STAT3 surrogate biomarker candidates. (B) Targets prioritisation based on systematic paired correlation analysis. Genes that were chosen for validation with ELISA are shown in bold. Others represent genes that are not in top 25% positively correlated with STAT3 in TCGA COADREAD database and genes that are not in top 25% downregulated/upregulated in TM5441 microarray database.

Figure 20:
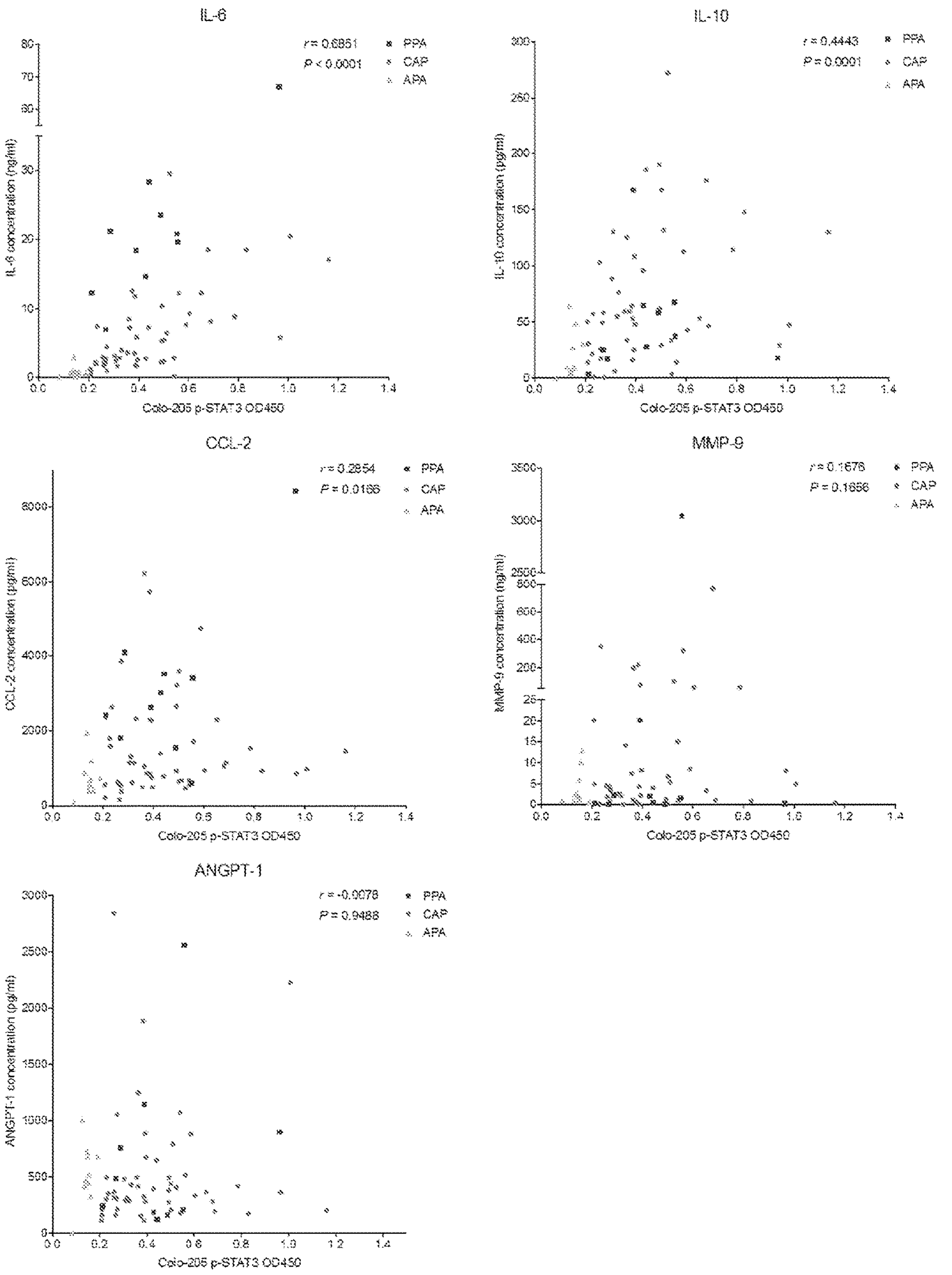
Figure 20:
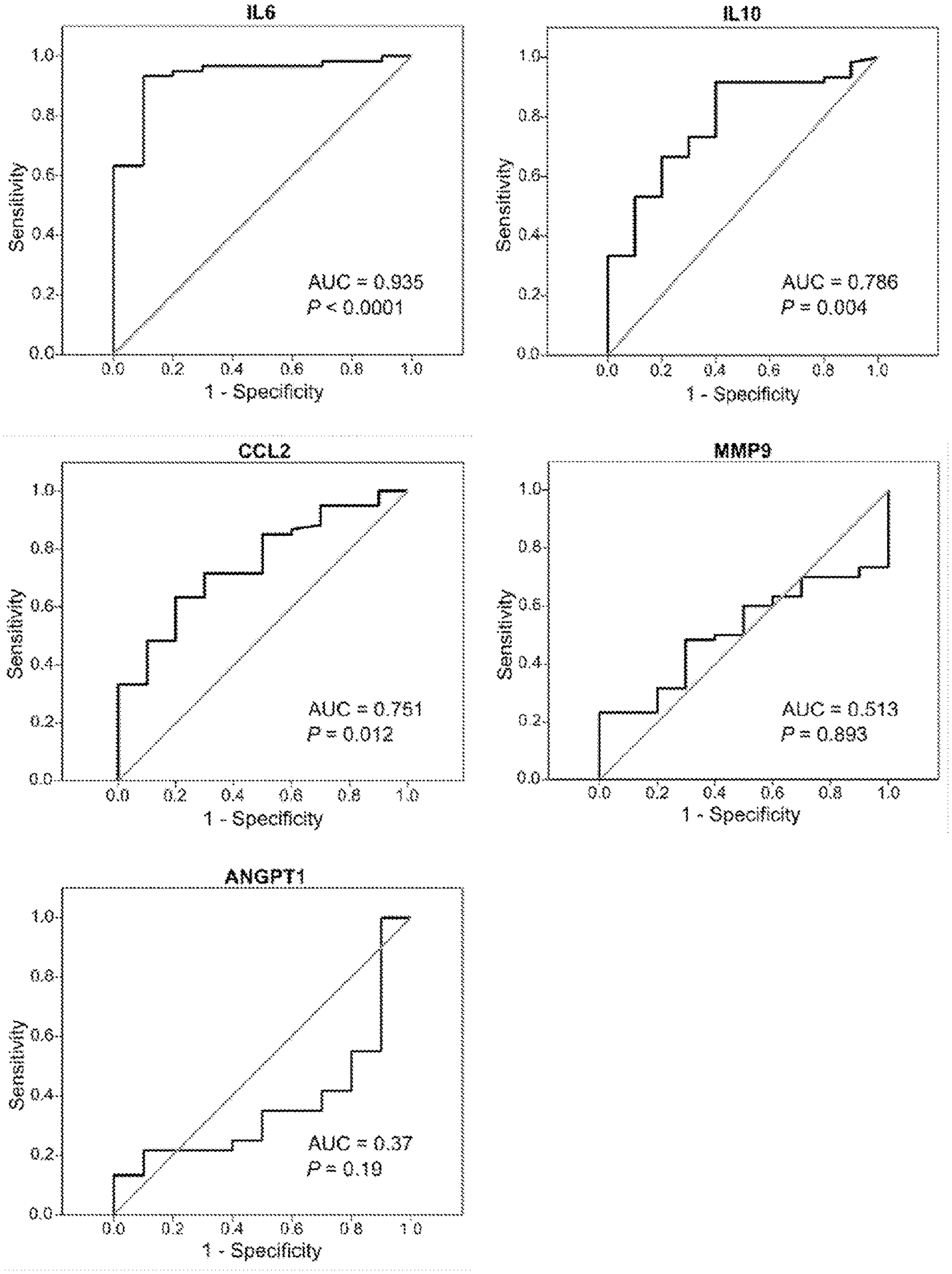

FIG. 20 shows validated surrogate biomarker panel of p-STAT3 (n=70). (A) Correlation between p-STAT3 and selected p-STAT3 surrogate biomarker candidates IL6, IL10, CCL2, MMP9, and ANGPT1. Concentrations of surrogate biomarkers in each patient's cell-free ascites were measured by ELISA and plotted against the degree of STAT3 phosphorylation (n=70 samples/surrogate marker). Correlation analyses were determined by Spearman correlation coefficient test. (B) Receiver operating characteristic (ROC) curve representing ability of individual p-STAT3 surrogate biomarkers to correctly classify PAI-1 paracrine addicted (PPA)/co-activators predominant (CAP) group or alternative pathways activation (APA) group. (C) Cut-off values of p-STAT3 surrogate biomarkers used to classify samples into PAI-1 paracrine addicted (PPA)/co-activators predominant (CAP) group or alternative pathways activation (APA) group. (D) Summary of classification accuracy of individual biomarkers and combinations of composite biomarkers. Biomarker is considered as positive (+) if the concentration of sample is above the cut-off value. (E) Summary of cut-off values that can be used to identify patients who might be susceptible to PAI-1 inhibition.

Figure 21:
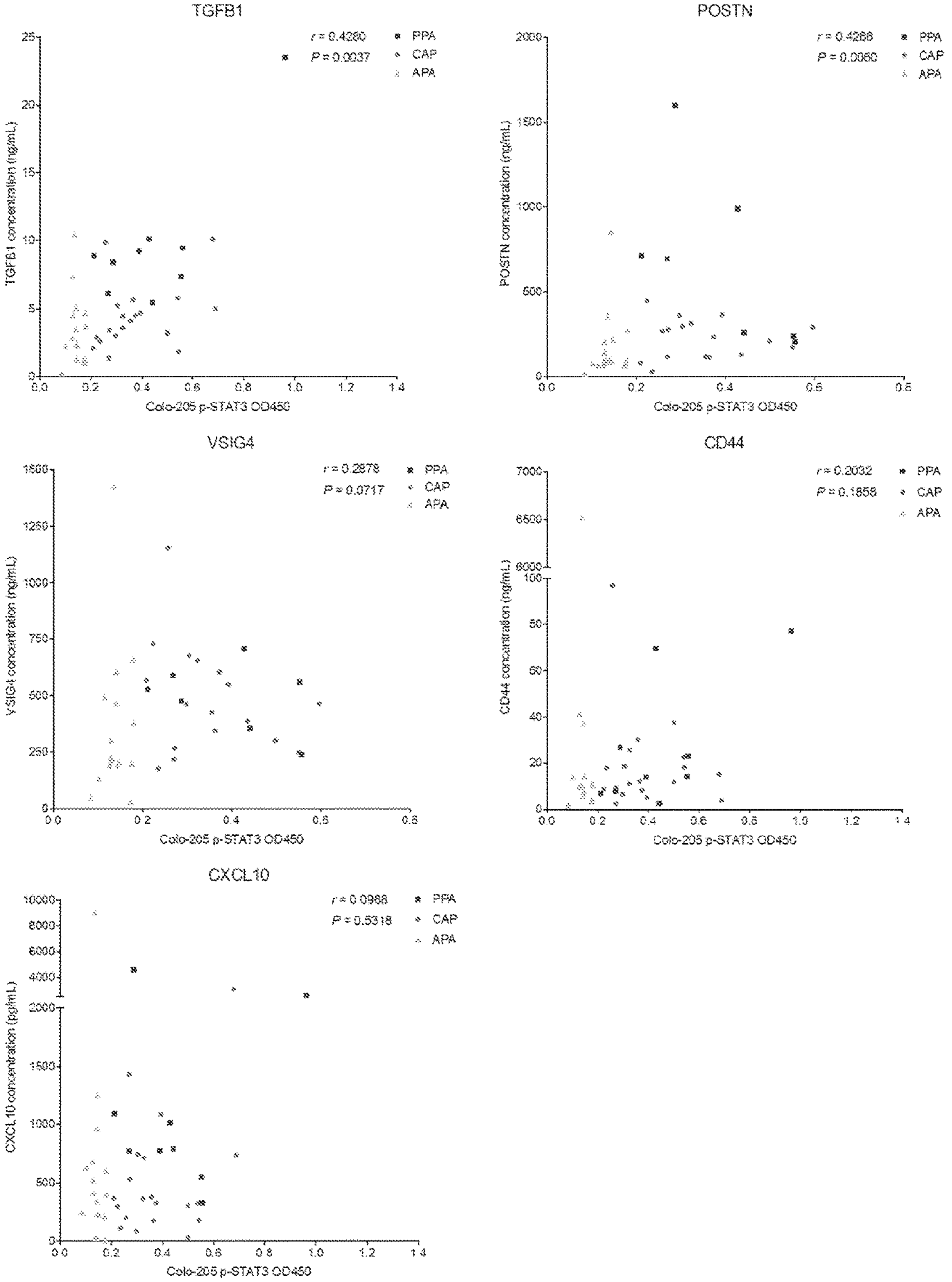
Figure 21:
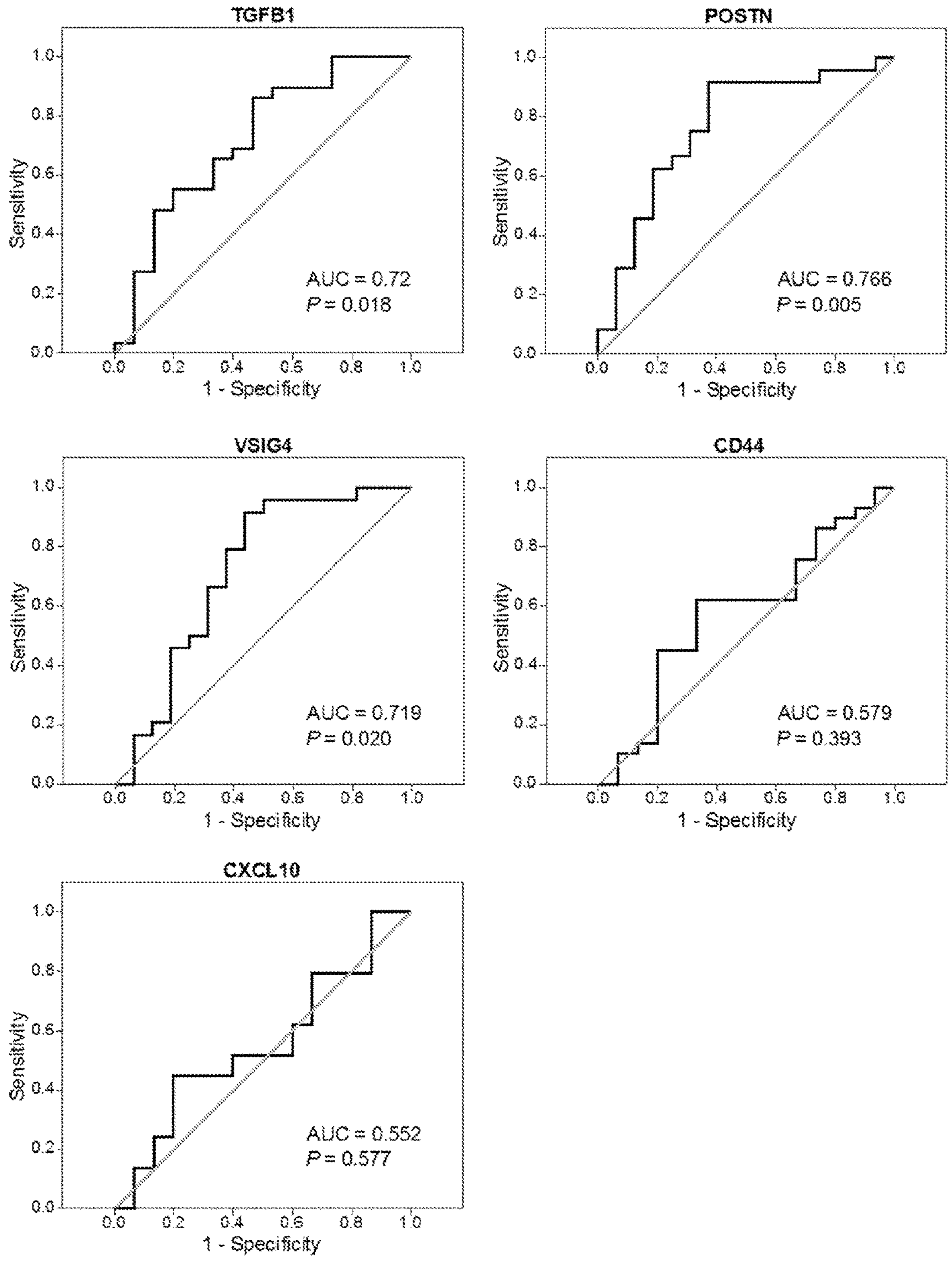

FIG. 21 shows an alternative surrogate biomarker panel of p-STAT3 (n=40), (A) Correlation between p-STAT3 and selected p-STAT3 surrogate biomarker candidates TGFB1, POSTN, VSIG4, CD44, and CXCL10. Concentrations of surrogate biomarkers in each patient's cell-free ascites were measured by ELISA and plotted against the degree of STAT3 phosphorylation (n=40 samples/surrogate marker). Correlation analyses were determined by Spearman correlation coefficient test. (B) Receiver operating characteristic (ROC) curve representing ability of individual p-STAT3 surrogate biomarkers to correctly classify PAI-1 paracrine addicted (PPA)/co-activators predominant (CAP) group or alternative pathways activation (APA) group. (C) Receiver operating characteristic (ROC) curve of composite biomarker panel comprising of TGFB1, POSTN, VSIG4, CD44, and CXCL10. (D) Receiver operating characteristic (ROC) curve of IL6 using matched samples used in TGFB1, POSTN, VSIG4, CD44, and CXCL10 analysis (left) and receiver operating characteristic (ROC) curve of composite biomarker panel comprising of IL6, TGFB1, POSTN, VSIG4, CD44, and CXCL10 (right). (E) Summary of area under the curve (AUC) of individual biomarkers and composite biomarker panels.

DEFINITIONS

As used herein, the terms "level" and "concentration" are used synonymously.

As used herein, the term "biomarker", or "marker", refers to molecular indicators of a specific biological property, a biochemical feature or facet that can be used to determine the presence or absence and/or severity of a particular disease or condition. In other words, "biomarker" is defined as a laboratory measurement that reflects the activity of a disease process. Examples of biomarkers are, but are not limited to, proteins, metabolites, genes, DNA and RNA. Biomarkers, as disclosed herein, refers to isolated biomarkers. Evaluation of such biomarkers and their correlation to a pathological condition or disease can be done by, for example, determining the absence or presence of a marker, differences in expression levels of the same marker in different clinical settings, and/or comparative analysis between diseased and disease-free samples.

As used herein, the term "surrogate marker" refers to the measurement of biomarker levels in bodily fluid that are indicative of an active biological process or signalling pathway, or clinicopathological grade of disease. For example, surrogate markers described herein refer to one or more biomarkers which can be used as a substitute for or as a proxy for the intended target. Thus, as used herein, a surrogate marker can also refer to a biomarker panel that serves as a substitute parameter for, for example, the level of STAT3 activation in cells via the analysis of patient ascites. For example, as shown herein, biomarkers listed herein can be used as surrogate markers for STAT3 phosphorylation.

As used herein, the term "PAI-1" refers to plasminogen activator inhibitor-1 (PAI-1), also known as endothelial plasminogen activator inhibitor or serpin E1. PAI-1 is a protein encoded by the SERPINE1 gene in humans. PAI-1's main function is the inhibition of urokinase-type plasminogen activator (uPA) and tissue-type plasminogen activator (tPA), enzymes responsible for the cleavage of plasminogen to form plasmin. Plasmin mediates the degradation of the extracellular matrix, either by itself or in conjunction with matrix metalloproteinases. In this scenario, PAI-1 inhibits urokinase-type plasminogen activator via active site binding, preventing the formation of plasmin. Additional inhibition is mediated by PAI-1 binding to the urokinase-type plasminogen activator (uPA)/urokinase-type plasminogen activator receptor (uPAR) complex, resulting in the latter's degradation. Thus, PAI-1 can be said to inhibit the serine proteases tissue-type plasminogen activator (tPA) and urokinase-type plasminogen activator (uPA)/urokinase, and hence is an inhibitor of fibrinolysis, the physiological process that degrades blood clots. In addition, PAI-1 inhibits the activity of matrix metalloproteinases, which play a crucial role in invasion of malignant cells through the basal lamina. In humans, PAI-1 is mainly produced by the endothelium (cells lining blood vessels), but is also secreted by other tissue types, such as adipose tissue and stromal tissue.

As used herein, the term "PAI-1 inhibitor" refers to compounds that are capable of inhibiting or blocking the activity of Plasminogen activator inhibitor-1 (PAI-1). Various compounds and drugs are not limited to a single effect and can therefore be considered to be PAI-1 inhibitors, even if they are structurally different. That is to say, the inhibition of PAI-1 is the combining characteristic of these compounds.

As used herein, the term "ascites" refers to an abnormal accumulation of fluid within the abdomen. There are many causes of ascites, including but not limited to, cirrhosis of the liver, cancer within the abdomen, congestive heart failure, and tuberculosis. The term "ascites" can also refer to free fluid in the peritoneal cavity. As used herein, when referring to ascites used in the context of treatment, for example, when exposing cells in cell culture to cell-free ascites, this refers to contacting cells in vitro to cell-free ascites fluid obtained from a subject, in order to elucidate changes in biomarker levels and observe the overall change in the molecular or physical phenotype of cells.

As used herein, the term "cell-free ascites" refers to the supernatant component of ascites derived from, for example, patients. The cell-free ascites as referred to herein was collected from the peritoneal cavity at the beginning of the cytoreductive surgery (CRS) or during routine ascitic tap (paracentesis) and was subjected, for example, to centrifugation at 2000 g for 10 minutes to separate the cellular component from the fluid component. Filter-sterilisation using 0.22 μm filter was performed on the fluid component to render it suitable for downstream experiments. A person skilled in the art would appreciate that other sterilisation methods known in the art can be used in order to obtain cell-free ascites suitable for downstream applications.

As used herein, the term "phosphorylation" refers to a process whereby a protein kinase transfers a phosphate group from an adenosine triphosphate (ATP) or guanosine triphosphate (GTP) to one or more free hydroxyl groups of amino acids. Generally speaking, phosphorylation is one of the on-off switches used in signalling cascades and pathways. Depending on the context of the pathway in question, phosphorylation can be used as an "on" or "off" switch. By way of an example of STAT3 phosphorylation (also termed "p-STAT3" in the present disclosure), in STAT3 signalling, the phosphorylation of critical amino acid residue (such as Tyrosine 705) on STAT3 induces the formation of STAT3 dimers, which then translocate into the nucleus to regulate specific gene expression and trigger downstream signalling cascades in the cell.

As used herein, the term "STAT3" refers to the signal transducer and activator of transcription 3, a transcription factor encoded by the STAT3 gene. In response to growth factors, hormones and cytokines, STAT3 is phosphorylated by upstream receptor kinase, thus undergoing dimerization prior to translocation into the nucleus, where the STAT3 dimer acts as a transcription activator. However, a STAT3 pathway can also be activated via a non-canonical pathway, independent of the upstream receptor kinase (see, for example, Interferon Independent Non-Canonical STAT Activation and Virus Induced Inflammation (Viruses. 2018 April; 10(4): 196)).

As used herein, the term "p-STAT3 activation level" is used interchangeably with the term "STAT3 phosphorylation", "STAT3 activation", or "level of STAT3 phosphorylation".

As used herein, the term "sample" refers to a biological sample, which includes, but is not limited to, any quantity of a substance from a living thing or formerly living thing. Such living things include, but are not limited to, humans, mice, monkeys, rats, rabbits, and other animals. Such substances include, but are not limited to bodily fluids, such as blood, plasma, ascites, serum, urine, cells, organs, tumour samples, biopsy samples, tissues, bone, bone marrow, lymph, lymph nodes, and skin. Such samples can be obtained from subjects known to suffer from the disease, subjects thought to suffer from the disease, and disease-free subjects. A person skilled in the art will appreciate that each type of sample could require different (pre-) processing steps before being able to be used in the claimed methods. By way of various examples, for samples that are in liquid form, centrifugation would need to be performed to separate the cellular and soluble components. For samples in solid form, tissue dissociation would need to be performed using a combination of mechanical dissociation and enzymatic treatment to create single-cell suspensions which can be centrifuged to separate the supernatant and cellular component. Both supernatant/soluble component and cellular component can then be evaluated via our in vitro and in vivo experiments. A person skilled in the art would be aware of the methods required in order to obtain samples suitable for use in the methods disclosed herein.

As used herein, the term "peritoneal carcinomatosis" refers to the intra-abdominal spread of cancer, whereby the origin of the carcinomatosis can be a malignancy arising from an intra-abdominal organ, or from the peritoneum (a thin layer of tissue that lines most of the abdominal organs) itself.

As used herein, the term "cytoreductive surgery (CRS)" refers to the complete removal of macroscopic tumour found in the abdominal cavity, via a series of peritonectomy and visceral resections.

As used herein, the term "hyperthermic intraperitoneal chemotherapy" refers to a therapy that is used in the eradication of microscopic disease left behind following cytoreductive surgery, which involves the addition of a heated solution of chemotherapeutic drug(s) into the abdominal cavity for 60 to 90 minutes.

As used herein, the term "paracrine factors" refers to diffusible and soluble proteins secreted by cells to modulate cellular responses in adjacent cells or the cell of origin via paracrine or autocrine interaction. Examples of such paracrine factors are, but are not limited to, interleukin 6 (IL6), transforming growth factor beta (TGF-β), Wnt proteins, Sonic Hedgehog (SHUT), vascular endothelial growth factor (VEGF) and epidermal growth factor (EGF).

As used herein, the term "oncogenic addiction", refers to a phenomenon whereby cells, when exposed to a certain paracrine factor, are led to the activation of a cellular signalling cascade. For example, STAT3 activation leads to the production and secretion of more of the same paracrine factor, leading to a positive feedback loop (see, for example, FIG. 18). These cells harness the positive feedback biological cycle for growth and activate pathway activation, and is hence addicted to this process. In the same logic, the term "oncogenic addiction to PAI-1" refers to the situation in which PAI-1 activation leads to production of more PAI-1, therefore leading to a positive, PAI-1-based, feedback loop. If the generation of such a positive feedback loop is prevented, the cells, devoid of a critical stimulus which they become accustomed to (that is addicted to), will die.

DETAILED DESCRIPTION

Presence of ascites in colorectal peritoneal carcinomatosis portends a poor prognosis. It is hypothesised that ascites are biologically relevant, and can be exploited for novel therapy. Exploiting tumour biology to identify novel therapeutic strategies in this disease is shown to have tremendous clinical impact. As shown herein, small molecule inhibitors targeting major signalling pathways in colorectal peritoneal carcinomatosis can be used in the clinical setting.

Thus, disclosed herein are methods which enable the targeted treatment of patients with peritoneal carcinomatosis. Also shown herein is that, for example, small molecule inhibitors targeting major signalling pathways can be used in the treatment of colorectal peritoneal carcinomatosis, or that these inhibitors can be used in the following clinical settings: in a neoadjuvant setting, to decrease tumour burden in patients who are not candidates for cytoreductive surgery (CRS) and hyperthermic intraperitoneal chemotherapy (HIPEC, also known as IPHC—Intraperitoneal hyperthermic chemoperfusion) to convert them into candidates for cytoreductive surgery and hyperthermic intraperitoneal chemotherapy; in an adjuvant setting, by adding small molecule inhibitors to a hyperthermic intraperitoneal chemotherapy regimen to improve the efficacy in eradicating residual microscopic disease after cytoreductive surgery; in a palliative setting, to decrease debilitating symptoms from peritoneal disease; and in a prophylactic setting, in patients with colorectal cancer who are at high risk of developing peritoneal carcinomatosis.

Currently, the only form of cure or standard of care for patients having or suffering from peritoneal carcinomatosis is to perform cytoreductive surgery and instill hyperthermic intraperitoneal chemotherapy at the end of the operation. However, current hyperthermic intraperitoneal chemotherapy regimens do not harness knowledge of tumour biology for therapy and merely uses conventional chemotherapy in the form of a cytotoxic drug. Moreover, patients who qualify for cytoreductive surgery and hyperthermic intraperitoneal chemotherapy only constitute 10% of all peritoneal carcinomatosis patients.

In the scope of the present disclosure, biomarkers have been identified that can predict response of treatment with intraperitoneal (IP) instillation of a PAI-1 inhibitor (for example, but not limited to, TM5441). Various groups of patients have been identified who are thought to respond to this therapy using the methods disclosed herein. One such group comprises patients with a high concentration of PAI-1 (≥20 ng/mL) and concurrently high STAT3 activation (≥0.2 OD450), which, without being bound by theory, are thought to be highly susceptible to PAI-1 inhibition. Another group comprises patients with a lower concentration of PAI-1 (<20 ng/mL) compared to the first group, but high STAT3 activation (≥0.2 OD450). Patients in this group are also considered to be susceptible to PAI-1 inhibition. This can be seen, for example, in ascites having high PAI-1 levels and concurrently activate STAT3 signalling in, for example, cancer cells. In the clinical context, intraperitoneal instillation of PAI-1 inhibitor can be used in the neoadjuvant, at the time of hyperthermic intraperitoneal chemotherapy or even in the palliative setting, hence providing a therapeutic option to much more patients than those who qualify for cytoreductive surgery and hyperthermic intraperitoneal chemotherapy. It is also thought that PAI-1 inhibitor can be aerosolized to be used in the palliative setting, for example in pressurized intraperitoneal aerosol chemotherapy (PIPAC).

In addition, the data generated shows that this strategy applies to patients with colorectal peritoneal carcinomatosis, and that it can also be applied to patients with other histological subtypes of peritoneal carcinomatosis.

Thus, in one example, subtypes of the peritoneal carcinomatosis can be but are not limited to, colorectal peritoneal carcinomatosis, small bowel peritoneal carcinomatosis, mesothelioma, endometrial peritoneal carcinomatosis, gastric peritoneal carcinomatosis, ovarian peritoneal carcinomatosis, appendiceal peritoneal carcinomatosis, pancreatic peritoneal carcinomatosis, urothelial peritoneal carcinomatosis and Pseudomyxoma peritonei (PMP). In another example, the peritoneal carcinomatosis is of unknown origin. In one example, the subtype of peritoneal carcinomatosis is colorectal peritoneal carcinomatosis.

As used herein, the term "unknown primary" when used in conjunction with tumours, tumour samples or subtypes, refers to the presence of peritoneal carcinomatosis where the primary tumour is undetermined by clinical, radiological and pathological assessment. Such indetermination can be due to reasons such as, but not limited to, the (small) insufficient size of primary tumour for pathological assessment, or that the primary tumour is encased by extrinsic peritoneal carcinomatosis such that clinical detection is not possible, or the lack of tumour markers with high specificity.

In the context of the experiments disclosed in the present disclosure, the term "other peritoneal carcinomatosis (PC) histologies" refers to histological subtypes of peritoneal carcinomatosis that originate from the following sites, namely, lung, breast, peritoneum, synchronous gastric and ovary, small bowel, urothelial, and palate. These samples are grouped under "other PC histologies" due to the small number of samples collected in each subgroup.

In one example, the peritoneal carcinomatosis is malignant. In another example, the peritoneal carcinomatosis is a primary tumour. In yet another example, the peritoneal carcinomatosis is a metastasis, or secondary tumour.

In another example, there is disclosed a method of predicting, determining or detecting susceptibility of a subject suffering from peritoneal carcinomatosis to a treatment with an anti-cancer drug or an anti-cancer treatment instilled within the peritoneal cavity based on the levels of PAI-1 within the ascitic fluid in the peritoneal cavity. Without being bound by theory, it is thought that STAT3 activation in cancer cells exposed to ascitic fluid allows the identification of a subgroup of patients who would benefit from inhibition of PAI-1.

As used herein, the term "susceptibility" refers to the propensity of something, for example a disease, to be likely affected by something else, for example, a treatment for said disease. This effect can be either positive or negative, depending on what is being referenced. For example, if a disease is sensitive to a particular treatment, then the susceptibility of said disease to a particular treatment is a positive effect. It can then be said that the disease is susceptible (or sensitive) to the treatment. On the other hand, if a disease is not susceptible to a given treatment, the disease is then considered to be unresponsive or resistant to said treatment.

As defined above, the term "predicting susceptibility" refers to the propensity of something, for example a disease, to be likely affected by something else, for example, a treatment for said disease. In other words, to predict susceptibility of a cancer to a particular treatment is to determine whether the cancer would react to a treatment with a certain medicament, or anti-cancer drug, or anti-cancer treatment. It is of note that the term "determining susceptibility" is not synonymous with, for example, "making a prognosis". The former term only looks at the possible reaction of a disease to a specific drug or therapy, while the latter describes the clinical outcome of the patient defined by parameters such as, but not limited to, the length of time of stable disease (once such a status is acquired), the length of time of overall survival and/or disease-free survival. While in some cases, it may be possible to correlate the effect of one term on the other, that is to say that a disease reacting well to a given treatment (that is, the disease is susceptible to the treatment) may increase the likelihood of said patient receiving a positive prognosis in regards to the overall disease progression, this is not to be taken as a rule. As a person skilled in the art would appreciate, a positive prognosis depends on many patient-specific factors in addition to the disease's susceptibility for treatment, for example, overall well-being of the patient prior to treatment, metabolism, diet, aggressiveness of the (primary) disease, secondary diseases and/or infections and the like.

Also disclosed herein is a method of predicting, determining or detecting susceptibility of a subject suffering from peritoneal carcinomatosis to a treatment with an anti-cancer drug or anti-cancer treatment.

Firstly, it was identified from clinical data in peritoneal carcinomatosis patients operated on that the presence of clinically apparent ascites within the peritoneal cavity leads to a poorer prognosis compared to patients who did not have clinically apparent ascites. This prognostic significance is relevant in peritoneal carcinomatosis of colorectal origin, although it is not limited to this histological subtype (FIG. 1). It is noted that the basis of comparison for the term "poorer prognosis" is the following: A group of patients with poorer prognosis are those patients with clinically apparent ascites during surgery as compared to the ones who do not have clinically apparent ascites during surgery. As used herein, the term "clinically apparent ascites" refers to ascites present in a volume of, for example, 50 ml or more during surgery.

Figure 2:
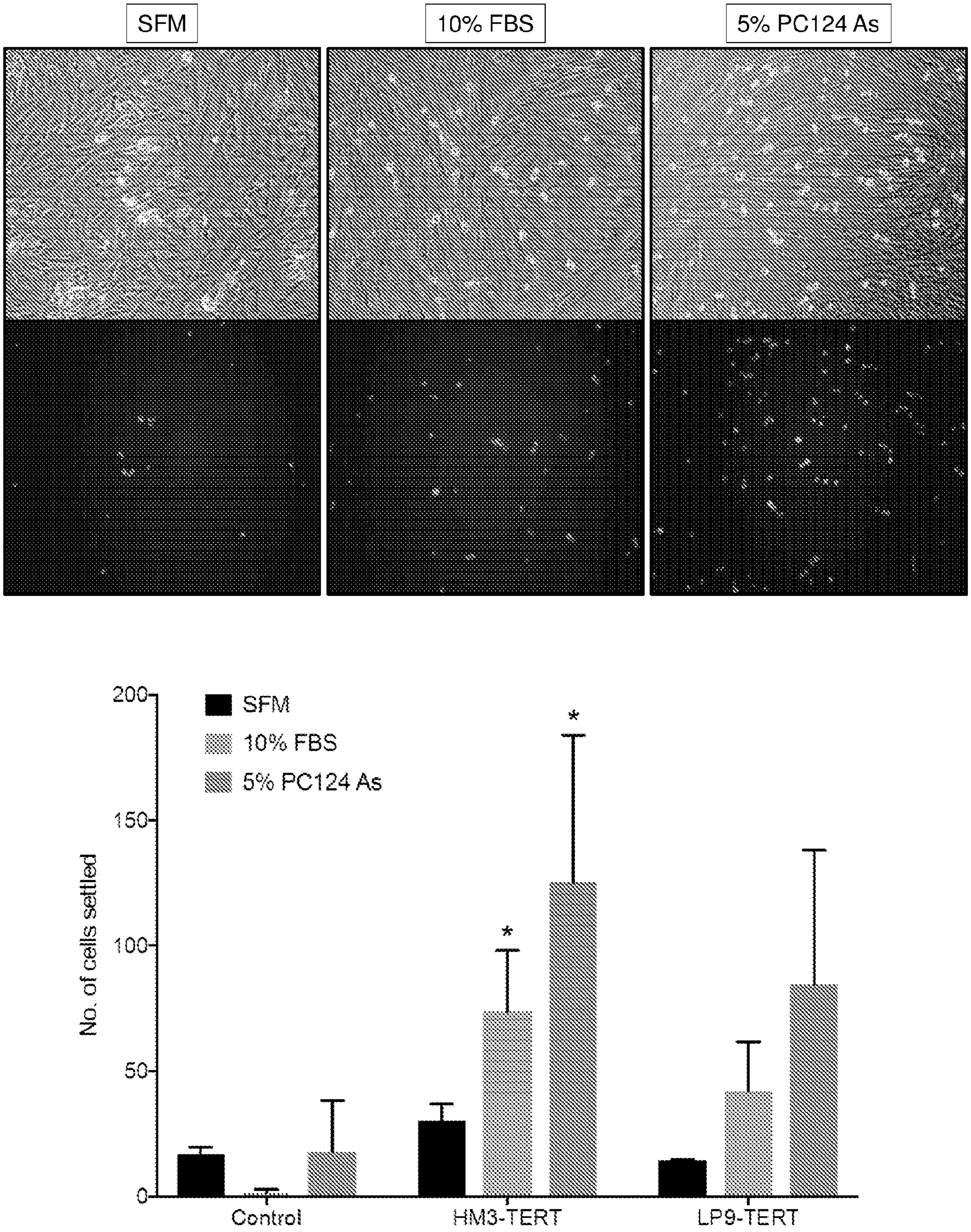
FIG. 2(A) Addition of cell-free ascites increased cancer cells proliferation in a dose-dependent manner 0.1% of cell-free ascitic fluid was sufficient to maintain cell viability without proliferation. (B) Treatment with cell-free ascites significantly increased cancer cells migration. (C) Treatment with cell-free ascites dramatically increased the cell settlement of cancer cells in vitro independently of serum supplemented media (As: Ascites, SFM: Serum-free media, FBS: Foetal bovine serum).

In vitro treatment of established cell line models of peritoneal carcinomatosis (Colo-205, HM3-TERT and LP9-TERT) with cell-free ascites collected from patients showed increased proliferation, migration, and establishment of colonies on stromal cells in co-culture models (FIG. 2), indicating that the cell line models of peritoneal carcinomatosis closely mimic the tumour in its in vivo setting.

Figure 3:
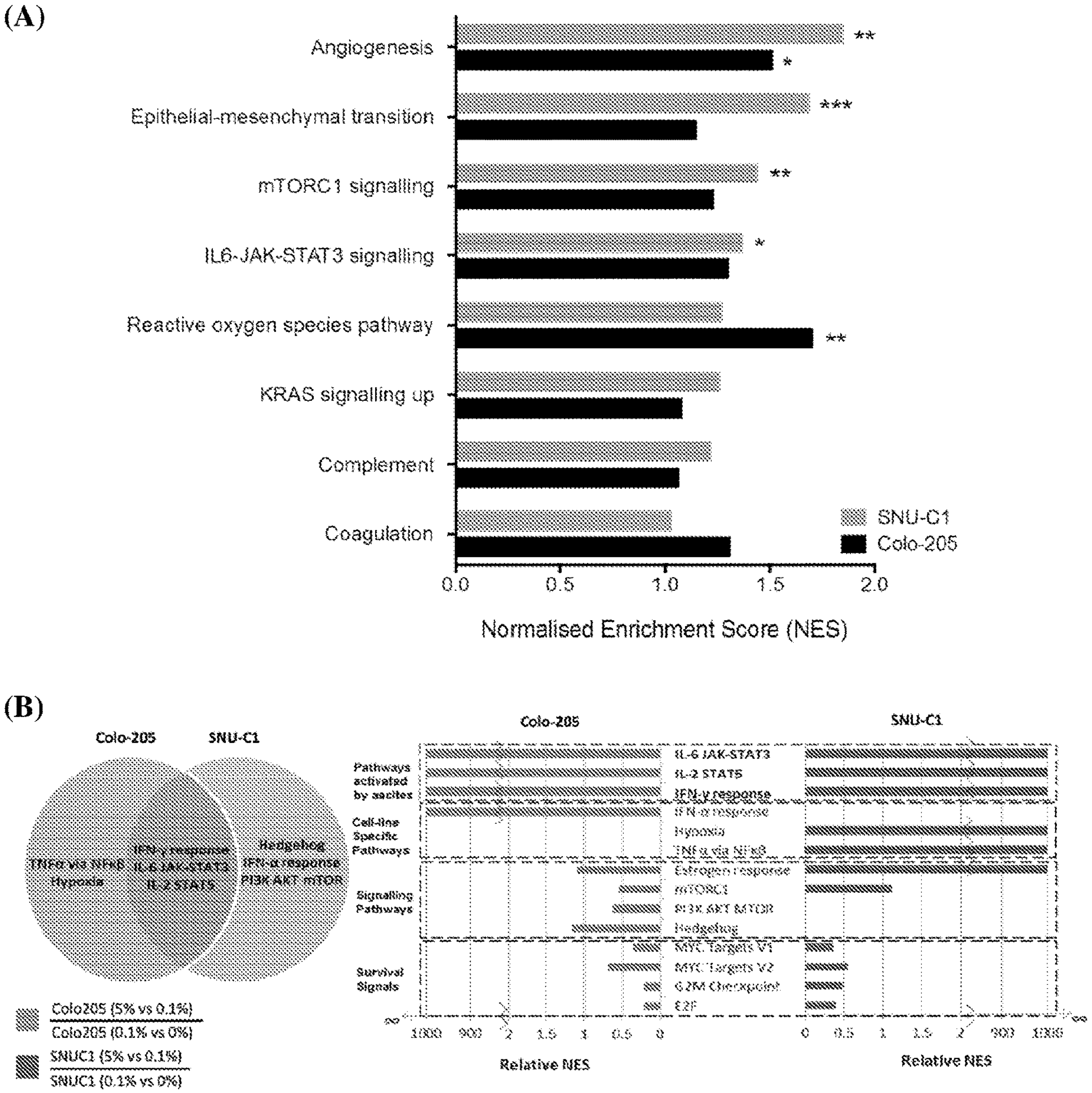
FIG. 3 shows pathways significantly upregulated upon treatment with cell-free ascites. (A) Pathways upregulated in peritoneal carcinomatosis (PC) cell lines treated with 5% versus 0.1% cell-free ascites. (B) Specific pathways upregulated in cell-free ascites treated cells that are not shared in pathways activated by survival signals. These figures show that upon treating cancer cell lines with cell-free ascites, several signalling pathways were found to be upregulated, including the IL6-JAK-STAT3 signalling pathway. This indicates that the activation of STAT3 plays an important role in the disease. The term "treatment", as referred to in the present figure and context, differs from the definition of "treatment" as provided in the definition section below. In the context of FIG. 3, treatment refers to the exposure of cell line models to cell-free ascites collected from patients in an in vitro setting. For example, cancer cell lines are exposed to 5% cell-free ascites in an in vitro setting and the cells are observed for a change in physical phenotype (e.g. proliferation or migration) or molecular phenotype (e.g. gene expression changes).

Gene expression analysis of peritoneal carcinomatosis cell lines treated with cell-free ascites showed that the STAT3 pathway was activated (FIG. 3), indicating that the activation of STAT3 plays an important role in the disease.

Western blot analysis of STAT3 phosphorylation in cells treated with cell-free ascites revealed that STAT3 signalling pathway was activated through phosphorylation at Tyr705 (FIG. 4*a*). Screening of cell-free ascites collected from different histological subtypes showed that STAT3 activation was the most prevalent when cells were treated with cell-free ascites collected from colorectal peritoneal carcinomatosis compared to peritoneal carcinomatosis from other anatomical origins (FIG. 4*b*). Thus, this data shows that cell-free ascites from colorectal peritoneal carcinomatosis induces a higher rate of STAT3 activation compared to cell-free ascites from peritoneal carcinomatosis of other anatomical origins. It is further of note that cell-free ascites collected from peritoneal carcinomatosis of other anatomical origins can also activate STAT3 signalling.

Figure 5:
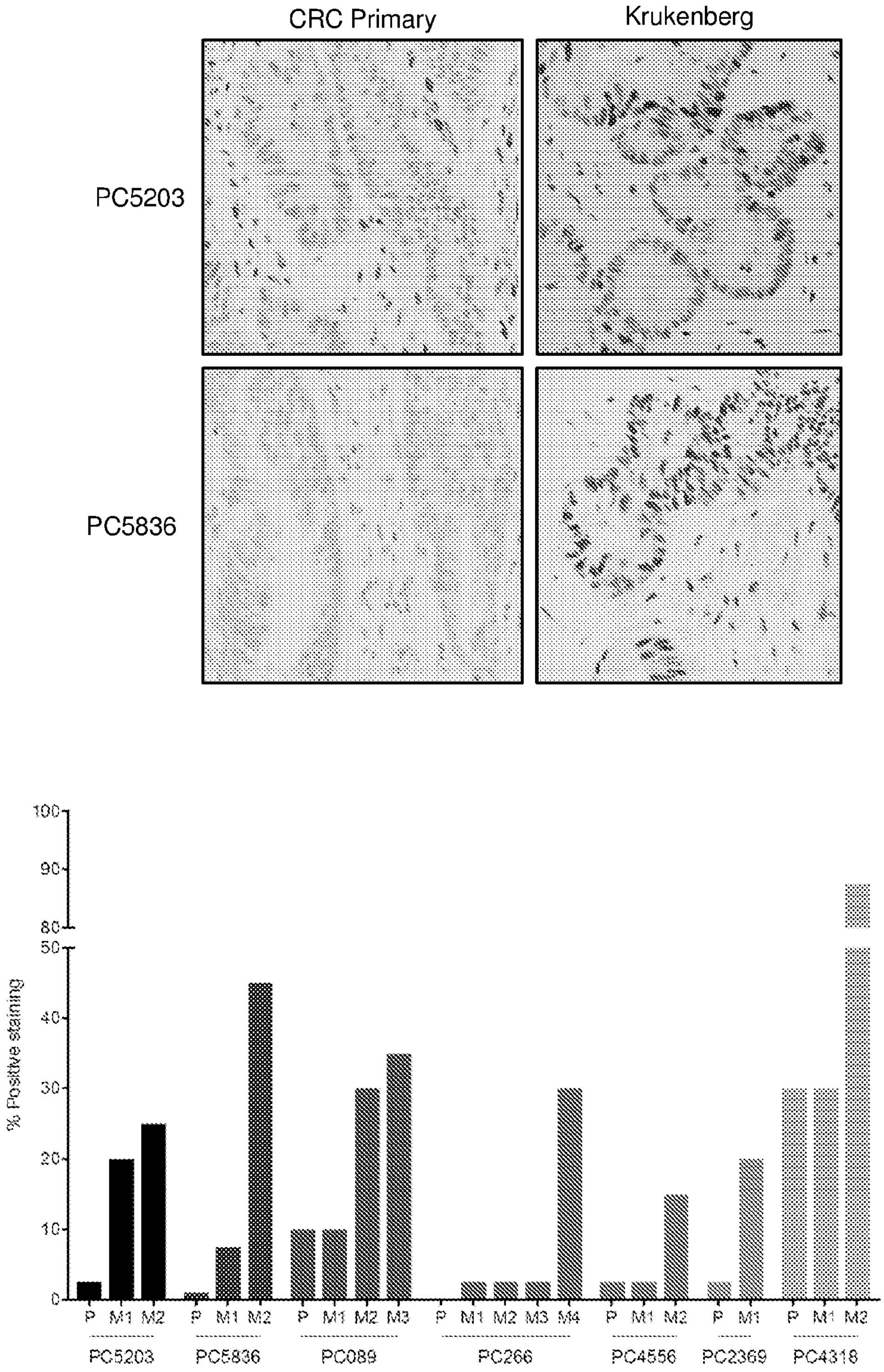
FIG. 5(A) Representative immunohistochemical staining of p-STAT3 in colorectal primary tumour and its matched metastases. (B) STAT3 activation is more prevalent in the metastases compared to the primary tumour (P: Primary tumour, M: Metastases). In the context of the present invention as a whole, this data highlights that STAT3 signalling pathway is more upregulated in metastases than the primary tumour, and by inference, more reliant on STAT3 signalling. This in turn suggests that metastases are more susceptible to STAT3 inhibition than the primary tumour. In other words, targeting STAT3 signalling in metastases can be more efficacious than targeting the primary tumour.

Immunohistochemistry of primary colorectal cancers matched with peritoneal metastases collected from the same patients showed that STAT3 activation was more prevalent in the metastases compared to the primary tumour (FIG. 5). Thus, this data shows that treatment of depriving metastatic cells of STAT3 signalling works well compared to the strategy of depriving primary tumours of STAT3 signalling. This is because STAT3 activation is more prevalent in metastases than primary tumours. As shown in the data presented herein, the subset of patients whose tumours have high STAT3 signalling due to high PAI-1 levels are more susceptible to PAI-1 inhibition compared to tumours whose STAT3 signalling is not activated by PAI-1. This is even less so in the tumours that do not show any activation in STAT3 signalling.

Figure 6:
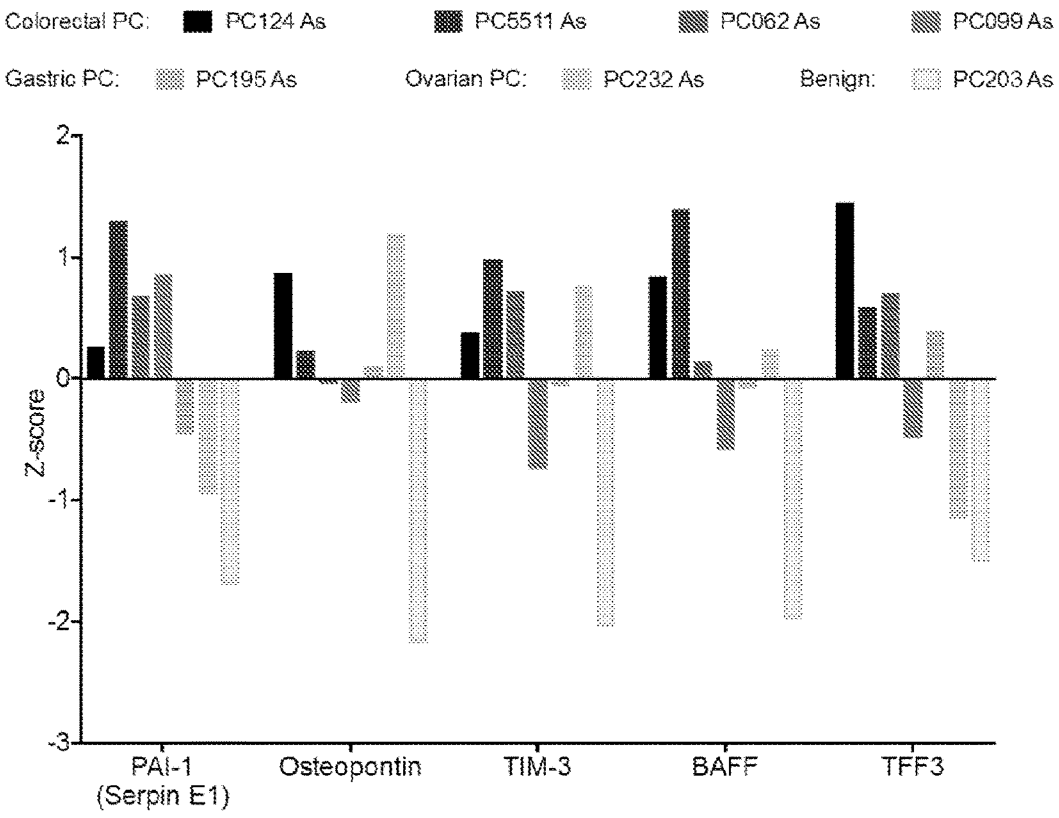
FIG. 6(A) Bar chart illustrating most differentially expressed epithelial-mesenchymal transition (EMT) genes in established cell line models of colorectal peritoneal carcinomatosis treated with cell-free ascites. (B) Proteins involved in the coagulation pathway were most prevalent in cell-free ascites of colorectal cancer origin. (C) Cytokine array performed on peritoneal carcinomatosis cell-free ascites from various histological subtypes identified abundant PAI-1 levels in cell-free ascites from colorectal peritoneal carcinomatosis.

Treatment of established cell line models of colorectal peritoneal carcinomatosis with cell-free ascites also led to the enrichment of the epithelial-mesenchymal transition (EMT) signature (FIG. 6*a*). An unbiased mass spectrometry screen of cell-free ascites along with a cytokine array performed on cell-free ascites of different histological origins identified the importance of coagulation/thrombolytic factors in cell-free ascites from colorectal peritoneal carcinomatosis (FIG. 6*b*). It is also shown that PAI-1 (which is involved in prevention of coagulation) is highly enriched in cell-free ascites from colorectal peritoneal carcinomatosis (FIG. 6*c*). This means that by analysing the proteomics of cell-free ascites, either via mass spectrometry or cytokine array, for example, it was found that the coagulation pathway was enriched in colorectal peritoneal carcinomatosis. From a marker candidate perspective, PAI-1, which is involved in the coagulation cascade, was also shown to be highly abundant. Thus, a phenomenon is being described whereby the presence of an active coagulation pathway is hijacked by cancer cells for oncogenic activation. In other words, and without being bound by theory, it is thought that the presence of activation of the coagulation pathway within the peritoneal cavity leads to oncogenic activation of signalling pathways in cancer cells initiated by coagulation factors or factors involved in prevention of coagulation. It is not intended to describe coagulation in the physical sense of having blood clots in the abdomen.

Figure 7:
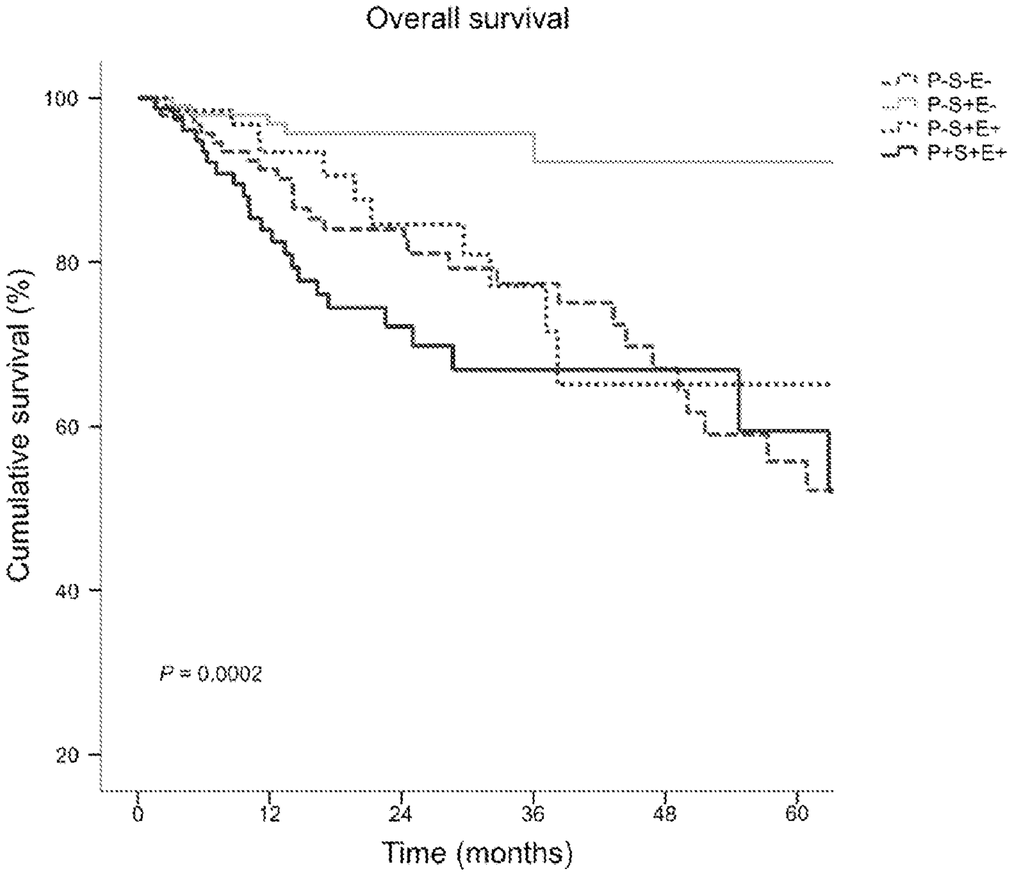
FIG. 7 shows interrogation of PAI-1, STAT3 and EMT expressions and survival analysis in The Cancer Genome Atlas Colorectal Adenocarcinoma (TCGA COADREAD) cohort (n=345). (A) Correlation between PAI-1 and STAT3 expressions. (B) Correlation between PAI-1 expression and EMT signature. Correlations in (A-B) were determined by Pearson correlation coefficient test. Linear regression lines are shown. (C) Kaplan-Meier survival analysis illustrating poorest survival in colorectal cancers with high levels of PAI-1, activated STAT3 signalling, and with enrichment of the epithelial-mesenchymal transition (EMT) signature. (P: PAI-1, S: STAT3 signalling, E: EMT signature)

Interrogation of The Cancer Genome Atlas (TCGA) database by the inventors showed that colorectal cancers with high levels of PAI-1 activated STAT3 signalling (FIG. 7*a*) and displayed enrichment of the epithelial-mesenchymal transition signature (FIG. 7*b*), and had the poorest prognosis (FIG. 7*c*). Taken together, it was shown that PAI-1 within the ascites can lead to STAT3 activation in cancer cells when these cancer cells are exposed to ascites, culminating in an epithelial-mesenchymal transition (EMT) phenotype that is responsible for the clinical manifestation of a biological aggressive tumour, leading to poor prognosis in these patients. Of note, activation of JAKs was not found in cell lines treated with cell-free ascites, suggesting that ascites activates STAT3 signalling in a non-canonical fashion (FIG. 8). This means that in this situation, STAT3 is activated in a non-canonical fashion, instead of the canonical fashion. Hence, without being bound by theory, it is thought that STAT3 can be activated by other activators (for example, PAI-1), instead of the canonical activator of STAT3 such as, for example, IL6.

Thus, in one example, the sample is, but is not limited to, ascites, blood, serum, urine, drain fluid, surgical drain fluid, liquid bodily fluids, supernatant obtained from cells, supernatant obtained from organs, supernatant obtained from tissues, lymph, supernatant obtained from lymph nodes, liquid biopsy samples, and supernatant obtained from biopsy samples.

Supernatant obtained from organs, tissues and the like can refer to liquid obtained from, for example, an organ sample which is macerated, minced, ground or crushed after extraction. Alternatively, for samples that contain little to no fluid, the sample can be placed in a clinical compatible buffer prior to or after mincing. The resulting liquid is termed a supernatant, which can then be used downstream for further analysis.

In another example, the sample is a liquid sample. In yet another example, the methods disclosed herein can be performed on one or more samples. For example, a method disclosed herein can be performed on two samples. In another example, the determining or measuring of the concentration of PAI-1 can be performed on one sample, and the determining or measuring of the level of STAT3 activation (for example, by way of phosphorylation) can be performed on another sample. These samples can be of the same or different origins. In one example, the first sample can be a cell-free sample, and the second sample can be a sample containing cells. In another example, the first sample can be ascites, and the second sample can be a biopsy sample. In one example, the concentration of PAI-1 and STAT3 activation (for example, by way of phosphorylation, or by way of surrogate markers) can be measured in a single sample. In other words, the determination of the concentration of PAI-1 and STAT3 activation can be performed on a single sample.

Having understood that PAI-1 is upstream of STAT3 activation in cancer cells via paracrine signalling, the levels of PAI-1 were systematically elucidated in cell-free ascites collected from patients with peritoneal carcinomatosis. An established cell line model of peritoneal carcinomatosis, Colo-205, was also treated with these cell-free ascites and levels of p-STAT3 elucidated using enzyme-linked immunosorbent assay (ELISA) to establish the magnitude of STAT3 activation. Plotting the levels of PAI-1 in ascites ($log_2$; x-axis) with the degree of STAT3 phosphorylation (leading to STAT3 activation) (y-axis), it was identified that the PAI-1 levels in ascites were positively correlated with the levels of STAT3 activation in cell-free ascites treated cells, both in the context of colorectal peritoneal carcinomatosis (PC) cell-free ascites, as well as cell-free ascites collected from peritoneal carcinomatosis (PC) of other histological subtypes (FIG. 9*a, b*).

The untransformed PAI-1 levels in cell-free ascites were then analysed with the corresponding degree of STAT3 phosphorylation in peritoneal carcinomatosis (PC) cells exposed to these ascites. Setting the phosphorylation of STAT3 (Tyr705) above 0.2 (OD 450) as a definition of activated STAT3 signalling, it was noted that all samples with PAI-1 level above 20 ng/mL showed activated STAT3 signalling. This observation prompted the definition of three (sub-)groups as shown in the following section.

Firstly, ascites with high PAI-1 levels (that is, PAI-1 levels of more than 20 ng/ml) were shown to rely heavily on PAI-1 to activate STAT3 signalling. These samples were termed PAI-1 paracrine addicted (PPA). Treatment of cell lines with cell-free ascites collected from these patients led to high levels of STAT3 phosphorylation (high STAT3 activity). Without being bound by theory, it is thought that STAT3 activation in cancer cells is likely exclusively dependent on PAI-1 levels within cell-free ascites collected from this group of patients, highlighting the phenomenon of oncogenic addiction to upstream activator of this pathway. Secondly, cell-free ascites with low PAI-1 levels (that is to say, PAI-1 levels of less than 20 ng/ml) and with activated STAT3 signalling in cells exposed to these cell-free ascites were termed co-activators predominant (CAP). Despite having low PAI-1 levels, treatment of cell lines with cell-free ascites collected from these patients still led to high levels of STAT3 phosphorylation (high STAT3 activity). Without being bound by theory, it is thought that in this group, STAT3 signalling was likely to be activated by PAI-1 and a combination of other ligands. Finally, cell-free ascites with low PAI-1 levels (that is to say, PAI-1 levels of less than 20 ng/ml) and which failed to activate STAT3 signalling likely had ligands that activated other signalling pathways. These samples were termed alternative pathways activation (APA). Treatment of cell lines with cell-free ascites collected from these patients did not lead to a significant level of STAT3 phosphorylation (low STAT3 activity). FIGS. 10*a* and 10*b* highlight that the classification of the different forms of cell-free ascites was applicable to both cell-free ascites of colorectal peritoneal carcinomatosis origin, as well as those from other histological subtypes.

To confirm this theory, Colo-205 cell line were treated in the presence of cell-free ascites from the 3 different subgroups with TM5441 (PAI-1 inhibitor), with the expectation that cells exposed to PAI-1 paracrine addicted (PPA) cell-free ascites will be highly sensitive towards PAI-1 inhibition. As predicted, differential sensitivity to PAI-1 inhibition according to the PAI-1 and p-STAT3 gating (FIG. 11) was observed. Treatment with another PAI-1 inhibitor (Tiplaxtinin) also showed the same trend of differential response, highlighting that the PAI-1 inhibition is specific, and that the results observed are not due to cytotoxic effects of the inhibitors (FIG. 12*a*). Subsequently, a STAT3 inhibitor (Napabucasin), a dual PI3K/mTOR inhibitor (BEZ235) and a conventional chemotherapeutic agent used in hyperthermic intraperitoneal chemotherapy (HIPEC) for treatment of colorectal peritoneal carcinomatosis (PC) (Mitomycin C) were tested to compare the efficacy in inhibition of oncogenic addiction to PAI-1 versus inhibition of downstream signalling pathway activated by cell-free ascites and cellular proliferation. It was found that direct targeting of cancer cells in the presence of cell-free ascites is ineffective because cell-free ascites promote chemoresistance in these tumour cells (FIG. 12*b-d*).

To further investigate the downstream signalling pathways involved in determining the sensitivity to PAI-1 inhibition, RNA microarray of Colo-205 cells treated with cell-free ascites representative of PAI-1 paracrine addicted (PPA) (PC085), co-activators predominant (CAP) (PC249), or foetal bovine serum (FBS; control) in the presence of TM5441 or DMSO vehicle was performed. Gene set enrichment analysis (GSEA) identified IL6-JAK-STAT3 signalling pathway to be significantly down-regulated in PAI-1 paracrine addicted (PPA) group upon PAI-1 inhibition (FIG. 13*a*). This finding is consistent with the initial hypothesis that the highly sensitive PAI-1 inhibition in PAI-1 paracrine addicted (PPA) group is attributed to PAI-1-STAT3 signalling pathway. Similarly, measurement of p-STAT3 in cells treated with these cell-free ascites and TM5441 demonstrated differential concentration needed to abrogate STAT3 activation (FIG. 13*b*).

As proof of concept that this is not exclusively a biological observation in vitro, Colo-205 cells were co-injected with cell-free ascites or foetal bovine serum (FBS) intraperitoneally in BALB/c nude mice to create a peritoneal carcinomatosis (PC) model. These mice were treated with intraperitoneal (i.p.) injection of TM5441. Consistent with the in vitro results, significant reduction in tumour burden was observed in PAI-1 paracrine addicted (PPA) cell-free ascites-treated mice (FIG. 14). In one example, the optimal drug delivery route was then assessed by comparing i.p. injection and oral administration of TM5441. I.p. instillation of TM5441 greatly outperformed oral administration in reducing tumour burden in peritoneal carcinomatosis (PC) mouse model (FIG. 15). This finding is in line with what has been observed in peritoneal carcinomatosis (PC) patients, where systemic administration of drugs has generally been considered to be ineffective due to the peritoneal-plasma barrier, leading to diminished penetration of cytotoxic agents from plasma into peritoneal tumours and ascites.

Subsequently, two patient-derived ascites-dependent xenografts (PDADXs) were developed, one from PAI-1 paracrine addicted (PPA) group (PC383 patient-derived ascites-dependent xenografts (PDADX)) and one from co-activators predominant (CAP) group (PC249 patient-derived ascites-dependent xenografts (PDADX)), to better recapitulate the PAI-1 addiction theory as an avatar of peritoneal carcinomatosis (PC) patients. Morphological evaluation of the patient-derived ascites-dependent xenograft (PDADX) tumours showed signet ring cell morphology, resembling the histology of the original patients' tumour. Immunohistochemical staining also confirmed that the patient-derived ascites-dependent xenograft (PDADX) tumours are of colonic origin (FIG. 16).

When treated with TM5441, PC383 patient-derived ascites-dependent xenograft (PDADX) mice exposed to matched cell-free ascites from the same patient elicited a significantly superior inhibition of tumour growth compared to vehicle control and to foetal bovine serum (FBS) group. In contrast, PC249 patient-derived ascites-dependent xenograft (PDADX) mice, which had been exposed to its matched patient's cell-free ascites and treated with TM5441, showed no reduction in tumour burden compared to vehicle control, similar to that of foetal bovine serum (FBS) group (FIG. 17*a*). When PC249 patient-derived ascites-dependent xenograft (PDADX) mice were exposed to cell-free ascites from PAI-1 paracrine addicted (PPA) group (PC383 ascites), these tumour cells became susceptible to PAI-1 inhibition, despite not being susceptible to PAI-1 inhibition in the presence of its own matched cell-free ascites (FIG. 17*b*). Taken together, this information describes a previously unknown phenomenon of oncogenic addiction in the context of a closed biological system, where tumours, along with their microenvironment, are segregated from the systemic circulation. Paracrine factors in this context provide the key stimulus for pathway activation; paracrine inhibition provides the critical stop point (FIG. 18).

The patient-derived ascites-dependent xenograft (PDADX) model has two components. The first component is the solid tumour that is formed by allowing the cellular components from ascites to form nodules in the host (usually in mice). The second component is cell-free ascites collected from the same patient from which the solid tumours had been obtained. The cell-free ascites is co-injected with the cellular component that is being propagated in the mice. This is a model considers the intrinsic phenotype of the cells, as well as the paracrine environment of the tumours within the peritoneal cavity.

As proof of concept, that the method disclosed herein is able to subclassify patient ascites into PAI-1 paracrine addicted (PPA), co-activators predominant (CAP) and alternative pathways activation (APA) groups, it was sought to identify surrogate markers of STAT3 activation in cells by analysing the cell-free ascites of patients. Briefly, STAT3-related genes were identified from Kyoto Encyclopedia of Genes and Genomes (KEGG) database by compiling all genes that are involved in known STAT3 pathways. Secreted STAT3-related proteins were selected based on extracellular genes listed in NCBI's Biosystems database and proteins that were identified by mass spectrometry analysis of cell-free ascites. Transcriptomics comparisons were performed using two databases to prioritize putative STAT3 surrogate markers, and to identify genes that are down-regulated and up-regulated in PAI-1 paracrine addicted (PPA) cell-free ascites-treated cells in response to TM5441 (PAI-1 inhibition). Genes were ranked from most down-regulated to most up-regulated, and systematic paired correlation analysis of candidate genes was subsequently performed. The paired analysis for each group was prioritized, as shown in FIG. 19*b*, and representative genes were chosen from each group based on literature review to streamline the selection to 35 genes. Targets were selected for further evaluation with enzyme-linked immunosorbent assay (ELISA) (FIG. 19) based on rank prioritisation, potential good correlation with p-STAT3 from Luminex assay data, and the importance of the candidate genes in cancer pathogenesis from literature review. Validating this in a cohort of 40 to 70 patients, a 4-biomarker panel was identified that can identify levels of STAT3 activation in cells via patient cell-free ascites analysis (FIG. 20 and FIG. 21). This finding also serves as the basis of, for example, a point of care stratification kit for patients who would benefit from PAI-1 therapy.

As described above, the present disclosure highlights exemplary cut-off levels of PAI-1 within the cell-free ascitic fluid in patients with peritoneal carcinomatosis and, when coupled with the levels of STAT3 activation in cancer cells exposed to these cell-free ascitic fluids, identifies a subgroup of patients who would benefit from inhibition of PAI-1.

In one example, the concentration of PAI-1 is between 0 to 450 ng/ml, between 10 to 20 ng/ml, between 15 to 25 ng/ml, or between 19 to 29 ng/ml. In one example, the concentration of PAI-1 is between 0 to 17 ng/ml. In another example, the concentration of PAI-1 is between 0 to 20 ng/ml. In another example, the concentration of PAI-1 in the context of the present invention is either less than 20 ng/ml, or more than or equals to 20 ng/ml.

In another example, the level of STAT activation, as measured by phosphorylation, is between 0 to 1.7, as measured at an optical density of 450 nm (OD450). In one example, the level of STAT3 activation, as measured by phosphorylation, is between 0.01 to 1, between 0.1 to 0.5, between 0.05 to 0.19, between 0.18 to 0.26, between 0.24 to 0.48, between 0.35 to 0.5, about 0.08, between 0.4 to 0.6, between 0.5 to 0.75, between 0.65 to 0.8, between 0.79 to 0.90, between 0.88 to 0.95, between 0.9 to 1, about 0.1, about 0.15, about 0.17, about 0.18, about 0.19, about 0.2, about 0.21, about 0.22, about 0.23, about 0.24, about 0.25, or about 0.3, as measured at an optical density of 450 nm (OD450). In another example, the level of STAT3 activation, as measured by phosphorylation, in the context of the present invention is either less than 0.2 ng/ml (OD450), or more than 0.2 (OD450).

The recitation of the term "0" (zero) is included as a value based on the understanding that "0" is also used when the presence of a marker is, for example, below the detection limit of a kit or a detection method, and is therefore immeasurable. In such cases, the observed value is often denoted as "n.a." or "nil".

In order to include most of the PAI-1 paracrine addicted (PPA)/co-activators predominant (CAP) samples, the surrogate biomarker values of the 60 PAI-1 paracrine addicted (PPA)/co-activators predominant (CAP) samples at the lower 5% percentile were selected as the initial cut-offs (extended data, not shown). For MMP9, the biomarker value with the highest value in the alternative pathways activation (APA) samples, 13 ng/ml was selected to exclude all alternative pathways activation (APA) samples. Based on a panel of 3 or 4 initial cut-offs, 52 PAI-1 paracrine addicted (PPA)/co-activators predominant (CAP) samples and two alternative pathways activation (APA) samples were filtered to be the PAI-1 paracrine addicted (PPA)/co-activators predominant (CAP) samples (extended data, not shown), corresponding to 86.67% and 80.0% accuracy, respectively.

In order to enhance the accuracy, more stringent cut-off values of IL6 and IL10 were chosen in order to exclude the false-positive alternative pathways activation (APA) samples, and less stringent cut-off values of CCL2 and MMP9 were chosen in order to include the false-negative PAI-1 paracrine addicted (PPA)/co-activators predominant (CAP) samples. The values of the final cut-offs are shown in FIG. 20*c*. Based on a panel of 3, or 4, final cut-offs, 56 PAI-1 paracrine addicted (PPA)/co-activators predominant (CAP) samples and one alternative pathways activation (APA) sample were filtered to be the PAI-1 paracrine addicted (PPA)/co-activators predominant (CAP) samples (extended data, not shown), corresponding to 93.33% and 90.0% accuracy, respectively. The overall accuracy of this composite biomarker panel (passing ≥3 biomarker cut-offs) is 92.86% (FIG. 20*b*).

Based on the information provided herein, it has been shown that IL6 alone is the statistically most robust predictor of the degree of STAT3 phosphorylation (p-STAT3), based on Stepwise Method and Best Subset Methods with Akaike Information Criterion or Bayesian Information Criterion. Generally speaking, regression analysis is a statistical approach to assess whether a set of independent variables significantly influences the dependent variable. Stepwise Regression is a method of fitting regression models by automatically adding or removing individual predictors and selecting a single model based on statistical significance. Best Subsets Regression is a method of comparing all possible models, using a specified set of predictors, and displays the best-fitting models that contain one predictor, two predictors, and so on Akaike information criterion is an estimator of out-of-sample prediction error and relative quality of each model, thus providing a means for model selection. Bayesian Information Criterion is a criterion for model selection, among a finite set of models, based on likelihood function, solving the problem of potential over-fitting by adding more parameters.

For example, a cut-off of IL6 at 997 pg/ml can define PAI-1 paracrine addicted (PPA)/co-activators predominant (CAP) samples with 95% accuracy and exclude an alternative pathways activation (APA) samples with 80% accuracy, corresponding to 92.86%. It is further shown that overall prediction accuracy can be increased with an increase in the number of biomarkers used in a composite biomarker panel. For example, a panel of IL6, IL10, CCL2 and MMP9 with a criterion of 3 or 4 positive biomarkers, is capable of identifying a PAI-1 paracrine addicted (PPA)/co-activators predominant (CAP) subject with 93.33% accuracy, and exclude an alternative pathways activation (APA) subject with 90% accuracy, corresponding to 92.86% overall accuracy. Other exemplary panels can be found throughout the present specification. The above means that the minimum number of markers required to obtain a statistically robust outcome is one biomarker (for example, IL6). These biomarkers can be, but are not limited to, the biomarker listed herein. In one example, the panel or group of biomarkers includes IL6. In one example, a single biomarker is used in the method disclosed herein, wherein the biomarker is, but is not limited to, IL6 (Interleukin 6), IL10 (Interleukin 10), CCL2 (chemokine (C—C motif) ligand 2; also referred to as monocyte chemo-attractant protein 1 (MCP1) or small inducible cytokine A2), MMP9 (matrix metallopeptidase 9, also known as 92 kDa type IV collagenase, 92 kDa gelatinase or gelatinase B (GELB)), TGFB1 (transforming growth factor beta 1), POSTN (Periostin, PN, or osteoblast-specific factor OSF-2), VSIG4 (V-set and immunoglobulin domain containing 4), CD44, and CXCL10 (C—X—C motif chemokine 10, also known as Interferon gamma-induced protein 10 (IP-10) or small-inducible cytokine B10). In another example, two biomarkers are used in the method disclosed herein, wherein the two biomarkers are, are, but are not limited to, the following combinations: IL6 and IL10; IL6 and CCL2; IL10 and CCL2; IL6 and MMP9; IL10 and MMP9; and CCL2 and MMP9. In yet another example, three biomarkers are used in the method disclosed herein, wherein the three biomarkers are, but are not limited to, the following combinations: IL6, IL10, and CCL2; IL6, IL10, and MMP9; IL6, CCL2, and MMP9; IL10, CCL2, and MMP9. In another example, four biomarkers are used in the method disclosed herein, wherein the four biomarkers are IL6, IL10, CCL2 and MMP9. In yet another example, five biomarkers are used in the method disclosed herein, wherein the five biomarkers are TGFB1, POSTN, VSIG4, CD44 and CXCL10. In another example, six biomarkers are used in the method disclosed herein, wherein the six biomarkers are IL6, TGFB1, POSTN, VISG4, CD44 and CXCL10. In a further example, the panel disclosed herein comprises the biomarkers, which are but are not limited to, L6; IL10; CCL2; MMP9; IL6 and IL10; IL6 and CCL2; IL10 and CCL2; IL6 and MMP9; IL10 and MMP9; CCL2 and MMP9; IL6, IL10, and CCL2; IL6, IL10, and MMP9; IL6, CCL2, and MMP9; IL10, CCL2 and IL6; and IL10, CCL2, and MMP9.

The cut-off values of, for example, four surrogate biomarkers were determined by the screening of 70 patient cell-free ascites. Taking into consideration the flexibility of patient samples, a range of ±5% cut-off value for each biomarker was included. Thus, in one example, the present invention, when referring to cut-off values, refers to the specific cut-off value with a buffer of ±5% or a buffer of ±2%.

In one example, one subgroup or subset of patients is defined as having a PAI-1 level of between 0 to 20 ng/ml, and a p-STAT3 activation level of less than 0.2 (OD450). In another example, one subgroup or subset of patients is defined as having a PAI-1 level of between 0 to 20 ng/ml, and a p-STAT3 activation level of equal to or more than 0.2 (≥0.2; OD450). In a further example, one subgroup or subset of patients is defined as having a PAI-1 level of equal to or more than 20 ng/ml (≥20 ng/ml), and a p-STAT3 activation level of equal to or more than 0.2 (≥0.2; OD450).

In yet another example, one subgroup or subset of patients is defined as having a PAI-1 level of between 0 to 17 ng/ml, and a p-STAT3 activation level of less than 0.2 (OD450). In another example, one subgroup or subset of patients is defined as having a PAI-1 level of between 0 to 17 ng/ml, and a p-STAT3 activation level of equal to or more than 0.2 (≥0.2; OD450). In a further example, one subgroup or subset of patients is defined as having a PAI-1 level of equal to or more than 17 ng/ml (≥17), and a p-STAT3 activation level of equal to or more than 0.2 (≥0.2; OD450).

The concentrations of five exemplary surrogate markers (in this case, IL6, IL10, CCL2, MMP9 and ANGPT1), identified using the methods disclosed herein, were plotted against the degree of STAT3 phosphorylation. The resulting graph is shown in FIG. 20. Based on Spearman Correlation analysis (R in FIG. 20), IL6, IL10 and CCL2 were selected to be surrogate biomarkers of STAT3 phosphorylation. Although MMP9 shows a weak correlation with phosphorylated STAT3, the concentration of MMP9 in the PAI-1 paracrine addicted (PPA)/co-activators predominant (CAP) samples is significantly higher than that in the alternative pathways activation (APA) samples (unpaired t test, $P<0.05$). The inclusion of MMP9 as a surrogate biomarker helps to exclude the alternative pathways activation (APA) samples from the PAI-1 paracrine addicted (PPA)/co-activators predominant (CAP) samples.

Thus, in one example, one subgroup or subset of patients is defined based on the concentration of PAI-1 and p-STAT3. In the event that p-STAT3 is used to determine which subgroup or subset of patients the subject to be tested belongs to (for example, in combination with PAI-1), the measurement of further surrogate markers in addition to p-STAT3 is optional. In another example, no further measurement of surrogate markers is undertaken, if p-STAT3 is measured directly. In another example, if p-STAT3 is not used to determine which subgroup or subset of patients the subject to be tested belongs to, the surrogate markers listed herein are used in place of direct measurements of STAT3 phosphorylation.

In one example, a concentration of PAI-1 of less than 20 ng/ml indicates that a patient belongs to either the co-activators predominant (CAP) or the alternative pathways activation (APA) subgroup. In another example, a PAI-1 concentration of more than or equals to 20 ng/ml indicates that the patient belongs to the PAI-1 paracrine addicted (PPA) subgroup.

In one example, a concentration of p-STAT3 of less than 0.2 OD450 indicates that a patient belongs to the alternative pathways activation (APA) subgroup. In another example, a concentration of p-STAT3 of at least 0.2 OD450 or more indicates that a patient belongs to either the PAI-1 paracrine addicted (PPA) or the co-activators predominant (CAP) subgroup.

In one example, the subgroup or subset of patients is defined as being of the PAI-1 paracrine addicted (PPA) group, if the patient is shown to have a PAI-1 concentration of at least 20 ng/ml or more, and a p-STAT3 concentration of at least 0.2 OD450 or more.

In one example, the subgroup or subset of patients is defined as being of the co-activators predominant (CAP) group, if the patient is shown to have a PAI-1 concentration of less than 20 ng/ml, and a p-STAT3 concentration of at least 0.2 OD450 or more.

In one example, the subgroup or subset of patients is defined as being of the alternative pathways activation (APA) group, if the patient is shown to have a PAI-1 concentration of less than 20 ng/ml, and a p-STAT3 concentration of less than 0.2 OD450.

In one example, the subgroup or subset of patients is defined as being of the PAI-1 paracrine addicted (PPA) group, if the patient is shown to have a PAI-1 concentration of at least 20 ng/ml or more, and an increased p-STAT3 concentration.

In one example, the subgroup or subset of patients is defined as being of the co-activators predominant (CAP) group, if the patient is shown to have a PAI-1 concentration of less than 20 ng/ml, and an increased p-STAT3 concentration.

In one example, the subgroup or subset of patients is defined as being of the alternative pathways activation (APA) group, if the patient is shown to have a PAI-1 concentration of less than 20 ng/ml, and a decreased p-STAT3 concentration.

In one example, the subgroup or subset of patients is defined as being of the PAI-1 paracrine addicted (PPA) group, if the patient is shown to have an increased PAI-1 concentration, and a p-STAT3 concentration of at least 0.2 OD450 or more.

In one example, the subgroup or subset of patients is defined as being of the co-activators predominant (CAP) group, if the patient is shown to have a decreased PAI-1 concentration, and a p-STAT3 concentration of at least 0.2 OD450 or more.

In one example, the subgroup or subset of patients is defined as being of the alternative pathways activation (APA) group, if the patient is shown to have a decreased PAI-1 concentration, and a p-STAT3 concentration of less than 0.2 OD450.

In one example, the concentration of p-STAT3 is measured using one or more surrogate markers, whereby the surrogate markers are, but are not limited to IL6, CCL2, IL10, MMP9, TGFB1, POSTN, VISG4, CD44, CXCL10, and combinations thereof.

In one example, one subgroup or subset of patients is defined using a panel of markers comprising IL6, CCL2, IL10, MMP9, TGFB1, POSTN, VISG4, CD44, and CXCL10. In another example, one subgroup or subset of patients is defined using a panel of markers comprising IL6, CCL2, IL10, and MMP9. In yet another example, one subgroup or subset of patients is defined using a panel of markers comprising PAI-1 and pSTAT3.

In one example, the cut-off value for IL6 is a concentration of 997 pg/ml. In another example, the cut-off value for IL10 is a concentration of 15 pg/ml. In another example, the cut-off value for CCL2 is a concentration of 450 pg/ml In yet another example, the cut-off value for MMP9 is a concentration of 3 ng/ml. In the above examples, a concentration equal to, or more than, each of the marker-specific cut-off values indicates that the patient belongs to the PAI-1 paracrine addicted (PPA) and co-activators predominant (CAP) subgroup. In other words, the values shown herein can also be termed the cut-off values or "(+)", for the respective marker. Conversely, if a measured concentration is below the above referenced cut-off value for the same marker, it can be indicated as "(−)" for the respective marker.

In one example, one subgroup or subset of patients is defined using a panel of markers comprising IL6, CCL2, IL10, and MMP9, whereby a combination of any 2 markers shown to have a concentration below the cut-off value indicates that the patient belongs to the alternative pathways activation (APA) subgroup.

In one example, one subgroup or subset of patients is defined using a panel of markers comprising IL6, CCL2, IL10, and MMP9, whereby a combination of any 3 markers shown to have a concentration above the cut-off value indicates that the patient belongs to the PAI-1 paracrine addicted (PPA) and co-activators predominant (CAP) subgroup.

In another example, one subgroup or subset of patients is defined using a panel of markers comprising IL6, CCL2, IL10, and MMP9, whereby all 4 markers shown to have a concentration above the cut-off value indicates that the patient belongs to the PAI-1 paracrine addicted (PPA) and co-activators predominant (CAP) subgroup.

In another example, one subgroup or subset of patients is defined using a panel of markers comprising TGFB1, POSTN, VSIG4, CCD44 and CXCL10, whereby all 5 markers shown to have a concentration above the cut-off value indicates that the patient belongs to the PAI-1 paracrine addicted (PPA) and co-activators predominant (CAP) subgroup.

In yet another example, one subgroup or subset of patients is defined using a panel of markers comprising IL6, TGFB1, POSTN, VSIG4, CCD44 and CXCL10, whereby all 6 markers shown to have a concentration above the cut-off value indicates that the patient belongs to the PAI-1 paracrine addicted (PPA) and co-activators predominant (CAP) subgroup.

In another example, the concentration of p-STAT3 is determined first, followed by the determination of the concentration of PAI-1.

In one example, if the patient is shown to belong to the PAI-1 paracrine addicted (PPA) and co-activators predominant (CAP) subgroup based on the concentration measurements for p-STAT3, then a PAI-1 concentration of less than 20 ng/ml indicates that the subject belongs to the co-activators predominant (CAP) subgroup. If the patient is shown to belong to the PAI-1 paracrine addicted (PPA) and co-activators predominant (CAP) subgroup based on the concentration measurements for p-STAT3, then a PAI-1 concentration of at least 20 ng/ml or more indicates that the subject belongs to the PAI-1 paracrine addicted (PPA) subgroup. If the patient is shown to belong to the alternative pathways activation (APA) subgroup based on the concentration measurements for p-STAT3, then a PAI-1 concentration of less than 20 ng/ml indicates that the subject belongs to the alternative pathways activation (APA) subgroup. If the patient is shown to belong to the alternative pathways activation (APA) subgroup based on the concentration measurements for p-STAT3, then a PAI-1 concentration of at least 20 ng/ml or more indicates that the subject belongs to an undetermined subgroup.

In another example, one subgroup or subset of patients is defined as having an IL6 concentration of less than 997 pg/ml, a CCL2 concentration of less than 450 pg/ml, an IL10 concentration of less than 15 pg/ml, and an MMP9 concentration of less than 3 ng/ml. This group refers to the alternative pathways activation (APA) group, as defined herein.

In another example, one subgroup or subset of patients is defined as having an IL6 concentration equal to or more than 997 pg/ml (≥997 pg/ml), a CCL2 concentration equal to or more than 450 pg/ml (≥450 pg/ml), an IL10 concentration equal to or more than 15 pg/ml (≥15 pg/ml), and a MMP9 concentration equal to or more than 3 ng/ml (≥3 ng/ml). This group collectively refers to the PAI-1 paracrine addicted (PPA) and co-activators predominant (CAP) groups, as defined herein.

In one example, the methods disclosed herein can be performed in a treatment setting, which is, but is not limited to, neoadjuvant setting, adjuvant setting, palliative setting and prophylactic setting. In another example, the methods disclosed herein can be performed on the same subject in one or more settings.

As used herein, the term "setting" refers to the timing when the biomarkers are assessed and timing of treatment. For example, the term "neoadjuvant setting" means that ascites fluid has been extracted before the patient has undergone surgery, and that the ascites fluid is extracted via a percutaneous drainage procedure. Upon determining susceptibility of patient, appropriate treatment (depending on which group patients falls into, i.e. PAI-1 paracrine addicted (PPA), co-activators predominant (CAP), alternative pathways activation (APA)) would be provided. In the adjuvant setting, a drain has been inserted prior to surgery to extract ascitic fluid from the intraabdominal cavity. Upon determining the susceptibility of patient, appropriate treatment (depending on which group patient falls into, i.e. PAI-1 paracrine addicted (PPA), co-activators predominant (CAP), alternative pathways activation (APA)) would be provided during hyperthermic intraperitoneal chemotherapy (HIPEC). In the palliative setting, patients do not undergo any surgery and the ascites fluid is extracted for analysis. The patient is treated accordingly (depending on which group patient falls into, i.e. PAI-1 paracrine addicted (PPA), co-activators predominant (CAP), alternative pathways activation (APA)) with a palliative intent.

In another example, the determination or measurement of the level of STAT3 activation (or phosphorylation) can be performed using surrogate markers. In another example, the level of STAT3 phosphorylation is determined by measuring the concentration of one or more surrogate markers. Alternatively, the level of STAT3 phosphorylation can also be determined by directly measuring the concentration of phosphorylated STAT3 directly. It will be appreciated by a person skilled in the art that STAT3 phosphorylation cannot be determined directly in, for example, a liquid sample, as phosphorylation takes place within cells. Therefore, when measuring levels of STAT3 phosphorylation in liquid form, cell lysis of cells that have been exposed to cell-free ascites in vitro, in vivo, and in the clinical setting must have taken place. The levels of STAT3 phosphorylation in the resulting sample determined using, for example, enzyme-linked immunosorbent assay (ELISA), or any other method capable of determining said levels. Cell lysis can be performed using methods known to a person skilled in the art, who would be able to ascertain which method is best suited for the sample in hand.

In another example, the level of STAT3 phosphorylation is determined by measuring the concentration of one or more surrogate markers present in the cell-free ascites. In yet another example, the level of STAT3 phosphorylation (p-STAT3) can also be determined by measuring the p-STAT3 level of cellular components present in ascites or tumour biopsy. In another example, the level of STAT3 phosphorylation can be determined by directly measuring the concentration of phosphorylated STAT3 directly and by measuring the concentration of one or more surrogate markers.

As used herein, the term “surrogate marker” refers to one or more (bio-)markers which can be used in substitute or a proxy of the intended target. The term “biomarker” can and is used interchangeable with the term “surrogate marker” in the present disclosure. For example, as disclosed herein, the level of STAT3 activation can be measured by determining the level of IL6. In one example, the relationship between a surrogate marker and the intended target can be proportional, meaning that an increase or decrease in the level or concentration of the surrogate marker is understood to have the same increase or decrease in the level or concentration of the intended target. This relationship can also be linear. However, it is also possible to have a surrogate marker with an anti-proportional relationship to the intended target.

In one example, the surrogate marker used for the determination of the level STAT3 activation (or phosphorylation) can be, but is not limited to, one or more of the markers as listed in Table 1.

In one example, the level of STAT3 phosphorylation is determined by measuring the concentration of at least 1, 2, 3, 4, 5, 6, 7, 8, 9, 10, or more surrogate markers. In one example, the level of STAT3 phosphorylation is determined by measuring the concentration of at least 3 surrogate markers. In one example, these 3 markers can be, but are not limited, to, IL6, IL10 and CCL2. In one example, the level of STAT3 phosphorylation is determined by measuring the concentration of at least 4 surrogate markers. In one example, these 4 markers can be, but are not limited to, IL6, IL10, CCL2 and MMP9. In one example, the level of STAT3 phosphorylation is determined by measuring the concentration of at least 5 surrogate markers. In one example, these 5 markers can be, but are not limited to, TGFB1, POSTN, VSIG4, CD44 and CXCL10. In one example, the level of STAT3 phosphorylation is determined by measuring the concentration of at least 6 surrogate markers. In one example, the 6 markers can be, but are not limited to, IL6, TGFB1, POSTN, VSIG4, CD44 and CXCL10. In one example, the method disclosed herein is performed using one surrogate marker. In another example, the method disclosed herein is performed using 2 surrogate markers. In another example, the method disclosed herein is performed using 3 surrogate markers. In another example, the method disclosed herein is performed using 4 surrogate markers. In another example, the method disclosed herein is performed using 5 surrogate markers. In another example, the method disclosed herein is performed using 6 surrogate markers. By way of an example, a biomarker panel, for example, will measure the concentration of a defined number biomarkers. In one example, the panel comprises or consists of IL6, IL10, CCL2 and MMP9. In the method disclosed herein, in order for a patient sample to be defined as PAI-1 paracrine addicted (PPA)/co-activators predominant (CAP), the values of the surrogate markers detected in the sample must pass the respective cut-off values defined for each of the surrogate markers. For example, in a panel of 4 markers, at least 3 for the 4 surrogate markers must pass their respective cut-off values. In a panel of 2 markers, for example, depending on the markers chosen, at least one biomarker or both biomarkers must pass their respective cut-off values. In a panel of 3 markers, for example, depending on the markers chosen, at least two biomarkers or all biomarkers must pass their respective cut-off values. In a panel of 4 markers, for example, depending on the markers chosen, at least 3 biomarkers or all biomarkers must pass their respective cut-off values. Exemplary panels can be found in FIG. 20D.

TABLE 1

Non-exhaustive list of putative surrogate markers for the determination of the level of STAT3 activation

| | | | | | | | |
|---|---|---|---|---|---|---|---|
| A1BG | CSF2 | IDE | CEACAM6 | SPARC | PDIA6 | IGKV2D-30 | LACRT |
| A2M | CSF3 | CFI | NBL1 | SPINK1 | NAMPT | IGKV2D-29 | FRMD7 |
| SERPINA3 | CSN2 | IFNA1 | NDP | SPINK2 | CELA3A | IGKV2D-28 | UCN2 |
| ABCA1 | CSN3 | IFNA2 | NID1 | SPINT1 | EBI3 | IGKV2D-26 | ERVH48-1 |
| ABCA3 | VCAN | IFNA4 | NODAL | SPN | USPL1 | IGKV1D-43 | IL33 |
| AOC1 | CST1 | IFNA5 | NPY | SPOCK1 | GDF11 | IGKV1D-33 | SCGB3A1 |
| ACHE | CST2 | IFNA6 | NOV | SPP1 | MSLN | IGKV1D-17 | BPIFB1 |
| ACPP | CST3 | IFNA7 | NPPA | SPTBN2 | LRRC17 | IGKV1D-13 | PKHD1L1 |
| ACTA1 | CST4 | IFNA8 | NPPB | SST | RAMP1 | IGKV1D-12 | CPA5 |
| ACTA2 | CSTA | IFNA10 | NPPC | ST14 | FSTL3 | IGKV1D-8 | MUC16 |
| ACTB | CSTB | IFNA13 | NUCB1 | STC1 | LILRB2 | IGKV6-21 | TGS1 |
| ACTC1 | CTBS | IFNA14 | NUCB2 | STX4 | RTN3 | IGKV4-1 | CMTM7 |

TABLE 1-continued

Non-exhaustive list of putative surrogate markers for the determination of the level of STAT3 activation

| | | | | | | | |
|---|---|---|---|---|---|---|---|
| ACTG1 | CTF1 | IFNA16 | OAS3 | XCL2 | CRISP3 | IGKV3-20 | IL17F |
| ACTG2 | CTGF | IFNA17 | OMD | TAC1 | AKR1A1 | IGKV3-15 | SAAL1 |
| ACTN4 | CTRB1 | IFNA21 | OGN | TAC3 | CCL26 | IGKV2-40 | CMTM1 |
| ACTN1 | CTRL | IFNAR2 | OMG | SERPINA7 | SEMA3A | IGKV2-30 | UCN3 |
| ADA | CTSB | IFNB1 | TNFRSF11B | ELOA | CPQ | IGKV2-28 | CGB1 |
| ADAM10 | CTSD | IFNG | ORM1 | TCN1 | WFDC2 | IGKV2-24 | CGB2 |
| ADCYAP1 | CTSG | IFNW1 | ORM2 | TCN2 | SPON2 | IGKV1-39 | ELFN2 |
| ADM | CTSH | IGF1 | OSM | TDGF1 | SPON1 | IGKV1-27 | C1QTNF1 |
| AEBP1 | CTSK | IGF2 | OXT | TF | OLFM1 | IGKV1-17 | C1QTNF2 |
| CRISP1 | CTSL | IGF2R | PCSK6 | TFF1 | LRRN2 | IGKV1-12 | C1QTNF3 |
| AFM | CTSV | IGFALS | PRDX1 | TFF2 | FAM3C | IGKV1-9 | C1QTNF4 |
| AFP | CTSO | IGFBP1 | SERPINE1 | TFF3 | MERTK | IGKV1-6 | C1QTNF5 |
| AGA | CTSS | IGFBP2 | SERPINB2 | TFPI | PIBF1 | MRPL18 | C1QTNF6 |
| AGRP | CTSW | IGFBP3 | PAM | TFRC | CAP1 | VPREB3 | VASN |
| AGT | CTSZ | IGFBP4 | REG3A | TGFA | CRTAP | HILPDA | CTHRC1 |
| AHSG | DAG1 | IGFBP5 | PAPPA | TGFB1 | ENOX2 | NENF | CMTM5 |
| ALAD | DBH | IGFBP6 | SERPINA5 | TGFB2 | SEMA4D | IL19 | ACSM1 |
| ALB | DCN | IGFBP7 | PCOLCE | TGFB3 | SEMA3C | LMCD1 | IL22RA2 |
| ALDH3A1 | ACE | CYR61 | PCSK1 | LEFTY2 | FBLN5 | KLK14 | MRGPRD |
| ALDOA | DDB1 | IGHA1 | PCSK5 | TGFBI | CIB2 | KLK12 | APOA5 |
| AKR1B1 | DEFA1 | IGHA2 | PCSK2 | TGFBR3 | PRDX4 | PLA2G3 | LRG1 |
| ALOX5 | DEFA3 | IGHD | PDE4C | THBD | AGR2 | IL20 | OLFM3 |
| ALPL | DEFA4 | IGHE | PDGFA | THBS1 | OLFM4 | IL22 | CPXM2 |
| AMBP | DEFA5 | IGHG1 | PDGFB | THBS2 | CXCL13 | DHH | LRRK2 |
| AMH | DEFA6 | IGHG2 | ENPP1 | THBS4 | NPC2 | SOST | LRIG3 |
| AMY1A | DEFB1 | IGHG3 | ENPP2 | THPO | GNLY | CELA2B | GPHB5 |
| AMY1B | DEFB4A | IGHG4 | PECAM1 | TIMP1 | POSTN | GAL | NRN1L |
| AMY1C | DLG3 | IGHM | SERPINF1 | TIMP2 | LEFTY1 | UTP11 | CMTM3 |
| AMY2A | DMBT1 | JCHAIN | PF4 | TIMP3 | SCGB1D2 | ANGPTL4 | ZG16B |
| ANG | DPEP1 | IGKC | PF4V1 | TIMP4 | SCGB1D1 | IRAK4 | SEZ6 |
| ANGPT1 | DPT | IGLC1 | CFP | TLE2 | TNFSF13B | SERPINA10 | TMIGD2 |
| ANGPT2 | DPYSL3 | IGLC2 | PFN1 | TMSB4X | STAG3 | EGFL7 | LRRC38 |
| ANPEP | EPYC | IGLC3 | PGC | CLEC3B | MASP2 | CKLF | PODN |
| ANXA1 | HBEGF | IGLC6 | PGF | TNF | MTHFD2 | CPA4 | NAXE |
| ANXA2 | ECM2 | IGLL1 | PGK1 | TNFAIP2 | CCL27 | C1RL | CPO |
| ANXA5 | ECM1 | IHH | SERPINA1 | TNFAIP6 | FGL2 | GOLM1 | LYZL4 |
| ANXA13 | EDN1 | IK | SERPINA4 | TNFRSF1A | EDDM3A | BPIFA1 | OTOP1 |
| APOF | EDN2 | IL1A | SERPINB5 | TNXB | CFHR3 | PLA1A | CD109 |
| APCS | EDN3 | IL1B | SERPINB6 | TPI1 | SMR3B | ANGPT4 | PXDNL |
| APOA1 | EEF1A1 | IL1RAP | SERPINE2 | TPO | UTS2 | WNT16 | CBLN4 |
| APOA2 | EGF | IL1RN | SERPINB8 | TPSAB1 | SMPDL3A | PRKAG2 | SOGA1 |
| APOA4 | EGFR | IL2 | SERPINB9 | TPT1 | POP1 | PCYOX1 | RBBP8NL |
| APOB | CELA1 | IL3 | SERPINB10 | CRISP2 | LMAN2 | IL23A | OVOS2 |
| APOC1 | ELANE | IL4 | SERPINI1 | TSHB | IL24 | ESF1 | A2ML1 |
| APOC2 | SERPINB1 | IL4R | SERPINB13 | TST | KLK11 | LSR | SERPINA12 |
| APOC3 | ENG | IL5 | SERPINI2 | TTR | KERA | OAZ3 | LRFN5 |
| APOC4 | ENO1 | IL5RA | PIGR | TNFSF4 | ADAMTS13 | GPRC5B | HAPLN3 |
| APOD | ENO2 | IL6 | PIP | UBA52 | ADAMTS5 | GHRL | TTBK2 |
| APOE | ENO3 | IL7 | PLA2G1B | UBB | PRSS23 | ERAP1 | CMTM4 |
| APOH | STOM | CXCL8 | PLA2G2A | UBC | EMILIN1 | ADA2 | CMTM2 |
| APP | STX2 | IL9 | PLAT | SCGB1A1 | FSTL1 | IL17D | IL34 |
| KLK3 | EPO | IL9R | PLAU | COL14A1 | ADAMTS7 | PRKAG3 | TMC8 |
| FASLG | ERBB3 | IL10 | PLG | VCAM1 | KLK8 | FAM3B | CCBE1 |
| AREG | EREG | IL11 | SERPINF2 | VEGFA | PRR4 | TLR9 | CBLN2 |
| ARG1 | F2 | IL12A | PLTP | VEGFB | SCRG1 | H2BFS | HFE2 |
| ASAH1 | F3 | IL12B | PNLIPRP2 | VEGFC | NID2 | CYTL1 | PM20D1 |
| ASIP | F5 | IL13 | PODXL | VGF | VASH1 | WNT4 | ERFE |
| SERPINC1 | F7 | IL13RA2 | POMC | EZR | CLSTN1 | SIAE | GDF7 |
| ATP4A | F8 | IL15 | PON1 | VLDLR | CEP164 | ADAMTSL4 | CPNE9 |
| AVP | F9 | IL15RA | PON3 | VPREB1 | ARSG | LRRN3 | CCDC80 |
| AXL | F11 | IL16 | PPBP | VTN | DKK1 | EPDR1 | CMTM8 |
| AZGP1 | F12 | TNFRSF9 | PPIA | WNT1 | CNOT1 | FAM20A | SPINK13 |
| AZU1 | F13A1 | IL17A | PPP1R1A | WNT2 | SIPA1L3 | BIVM | PRSS3P2 |
| B2M | FABP3 | IL18 | PPT1 | WNT3 | SSPO | SEMA4C | LINGO2 |
| BCHE | FAP | INHA | PPY | WNT5A | FRMD4B | CMTM6 | EEF1A1P5 |
| CFB | FBLN1 | INHBA | PRELP | WNT6 | PMPCA | LIME1 | CFAP58 |
| BGLAP | FBLN2 | INHBB | SRGN | WNT7A | SULF1 | ODAM | LGI4 |
| BGN | FBN1 | INHBC | PRH1 | WNT7B | DNAJC9 | INTS11 | TMPRSS6 |
| BMP1 | EFEMP1 | CXCL10 | PRH2 | WNT8A | KIAA0556 | ENOX1 | FREM3 |
| BMP2 | FKTN | INS | PROC | WNT8B | MTCL1 | WDR60 | BMPER |
| BMP3 | FCN2 | INSL4 | PROS1 | WNT10B | MCF2L | LGI2 | QSOX2 |
| BMP4 | GPC4 | ISLR | PRSS1 | WNT11 | DMXL2 | THNSL2 | SUPT20HL2 |
| BMP5 | FGA | ITGA2B | PRSS2 | WNT2B | ZCCHC11 | RNLS | ADAMTS15 |
| BMP6 | FGB | ITGAM | PRSS3 | WNT9A | MAN2B2 | NDUFAF7 | KRT78 |
| BMP7 | FGF1 | ITIH1 | MASP1 | WNT9B | ADNP | ZNF446 | ZFC3H1 |
| BMP8B | FGF2 | ITIH2 | RELN | XDH | CELA3B | KDM4D | DAND5 |
| BMPR2 | FGF5 | ITIH4 | KLK7 | YWHAZ | ANGPTL2 | SLF2 | GKN2 |

TABLE 1-continued

Non-exhaustive list of putative surrogate markers for the determination of the level of STAT3 activation

| | | | | | | | |
|---|---|---|---|---|---|---|---|
| BPI | FGF6 | ANOS1 | PRSS8 | ZNF177 | CLCF1 | IL26 | LIPH |
| BTC | FGF9 | KARS | KLK6 | ZP3 | DNPEP | SELENOS | C9orf72 |
| BTD | FGF10 | KCNK3 | HTRA1 | PXDN | PYY2 | DEFB103B | C3orf58 |
| BTN1A1 | FGF12 | KISS1 | PRTN3 | SCG2 | LY96 | APOBR | LRRC55 |
| C1QBP | GPC5 | KIT | PSAP | MANF | PLA2G15 | APOM | UCMA |
| SERPING1 | FGG | KLKB1 | PYY | PLA2G7 | FLRT3 | SULF2 | GPC2 |
| C1QA | FGL1 | KNG1 | PSMC5 | ADAM12 | FLRT2 | MYDGF | SCUBE3 |
| C1QB | VEGFD | KRT1 | PTGDS | FGF23 | FLRT1 | PDGFC | SEMA3D |
| C1QC | FLT1 | KRT2 | PTGIS | MFAP5 | FJX1 | CPXM1 | IL27 |
| C1R | FLT3LG | KRT9 | PTH | MIA | ATXN10 | GKN1 | ZBTB38 |
| C1S | FMOD | KRT10 | PTHLH | GDF5 | KLK5 | IL36G | UBN2 |
| C2 | FN1 | KRT31 | PTN | EPX | PRDX5 | CCL28 | BPIFC |
| C3 | FRZB | KRT33A | QSOX1 | COLQ | CHRDL2 | MUC13 | EPGN |
| C4A | FSHB | KRT33B | PTPRG | HIST1H2BG | ABI3BP | RETN | PCSK9 |
| C4B | FUCA2 | KRT34 | PTPRR | HIST1H2BF | PAMR1 | IFNK | NPNT |
| C4BPA | GAST | KRT35 | PTX3 | HIST1H2BE | SOSTDC1 | GRIPAP1 | SERPINA11 |
| C4BPB | KDSR | KRT81 | PVR | HIST1H2BI | EGFL6 | FAM20C | KLHL34 |
| C5 | GAS6 | KRT83 | PZP | HIST1H2BC | TSKU | ADAMTS9 | MDS2 |
| C8A | GBA | KRT85 | RARRES2 | HIST2H2BE | MOXD1 | TWSG1 | PR5533 |
| C8B | GC | KRT86 | RBP3 | PLA2G6 | KLK13 | CPA6 | MDGA1 |
| C8G | GCG | LALBA | RBP4 | SPARCL1 | FGF21 | EPPIN | IFNL2 |
| C9 | BLOC1S1 | LAMA2 | RDX | LTBP4 | GNL3 | SLURP1 | IFNL3 |
| CA2 | KAT2A | LAMA5 | REN | ATRN | TIMM8B | RALGAPA2 | IFNL1 |
| CA6 | GCNT1 | LAMB1 | RNASE3 | CILP | IL36RN | DSCAML1 | PRTG |
| DDR1 | GDF1 | LAMB2 | RNPEP | PPFIBP2 | GREM1 | LRFN2 | BRICD5 |
| CALCA | GDF2 | LAMC1 | RPL39 | CPZ | FETUB | MTUS1 | METRNL |
| CALR | MSTN | LAMC2 | RPS27A | APOL1 | FGF22 | LRFN1 | LAMA1 |
| CAMP | GDF9 | LAMP2 | RS1 | FCN3 | LYPD3 | LRRN1 | HMSD |
| CAT | GDF10 | LBP | S100A4 | YARS | DKKL1 | COL20A1 | SSC5D |
| SERPINA6 | GGT1 | LCAT | S100A8 | TNFSF11 | DKK3 | ZSWIM5 | CXCL17 |
| CBR3 | B4GALT1 | LCN1 | S100A9 | STC2 | DKK2 | LRRC4C | VSTM1 |
| CCK | GH1 | LCN2 | S100A11 | NPFF | CPAMD8 | NCOA5 | FAM19A3 |
| KRIT1 | GHR | LCP1 | S100A13 | CDK13 | CHIA | SCUBE2 | C3orf33 |
| CD5L | GHRH | LDLR | S100B | RNASET2 | IL36B | HAMP | LCN1P1 |
| CD9 | GIF | LECT2 | SAA1 | CHRD | IL37 | WFDC1 | SERPINA9 |
| CD14 | GIP | LEP | SAA2 | SERPINB7 | IL36A | CXCL16 | GPIHBP1 |
| MS4A1 | GPC3 | LGALS1 | SAA4 | CTSF | IL17C | OPRPN | IFNE |
| TNFSF8 | GLB1 | LGALS3 | SERPINB3 | TNFSF14 | IL17B | IL21 | C1QL4 |
| CD36 | GLE1 | LGALS3BP | SERPINB4 | TNFSF13 | TINAG | ACE2 | KLHL17 |
| ENTPD6 | GNB2 | LGALS4 | CLEC11A | TNFSF12 | SRPX2 | CELA2A | VWA2 |
| CD40 | GNL1 | LGALS8 | SCT | TNFSF10 | SMPDL3B | GFRA4 | OTOG |
| CD40LG | GNRH1 | LGALS9 | CCL1 | TNFSF9 | BMP10 | TINAGL1 | GLDN |
| CD59 | SFN | LHB | CCL2 | ADAM15 | RBMX | IRF2BPL | OSTN |
| CD63 | GP5 | LIF | CCL3 | ADAM9 | ANGPTL3 | SIL1 | ACTBL2 |
| CD70 | GPC1 | LIFR | CCL3L1 | TNFRSF6B | PCSK1N | GREM2 | CLEC18A |
| ADGRE5 | GPI | LIPC | CCL4 | DLK1 | IGKV1-5 | IL25 | C6orf58 |
| CDH13 | GPLD1 | LOX | CCL5 | CREG1 | IGHV6-1 | VWA1 | BMP8A |
| CEL | GPT | LOXL1 | CCL7 | FGF18 | IGHV5-51 | ZNF649 | IGFL1 |
| CETP | GPX3 | LOXL2 | CCL8 | FGF17 | IGHV4-61 | CHID1 | MROH7 |
| CFL1 | GPX5 | LPA | CCL11 | FGF16 | IGHV4-28 | LRFN4 | VWC2 |
| CFL2 | GRN | LPL | CCL13 | NRP1 | IGHV4-4 | METRN | KCP |
| CTSC | CXCL1 | LPO | CCL14 | GGH | IGHV3-74 | APOO | IL31 |
| CEACAM8 | CXCL2 | LTA | CCL15 | WISP3 | IGHV3-73 | FKRP | SOGA3 |
| CHEK1 | CXCL3 | LTB | CCL16 | WISP2 | IGHV3-72 | CRELD2 | C10orf99 |
| CHGA | GRP | LTBP1 | CCL17 | WISP1 | IGHV3-66 | GLB1L | CCL4L1 |
| CHI3L1 | PDIA3 | LTBP2 | CCL18 | PROM1 | IGHV3-64 | LRFN3 | C3P1 |
| CHI3L2 | GSN | LTF | CCL19 | PROZ | IGHV3-49 | TCTN1 | CEACAM16 |
| CHIT1 | GSTP1 | LUM | CCL20 | APLN | IGHV3-43 | FAM184A | C1QTNF12 |
| CKB | GUSB | LYZ | CCL21 | ENDOU | IGHV3-30 | GSDMD | SERPINA2 |
| CLCA1 | HABP2 | TACSTD2 | CCL22 | HIST1H2BJ | IGHV3-23 | MMRN2 | TRIM75P |
| CLU | HBA1 | MAN2A1 | CCL23 | SELENBP1 | IGHV3-21 | PLBD1 | GDF6 |
| CLIC1 | HBA2 | MAN2B1 | CCL24 | TNFSF18 | IGHV3-15 | PDZD7 | PATE2 |
| CNP | HBB | MATN2 | CCL25 | ARTN | IGHV3-13 | SVEP1 | PATE4 |
| CNTF | HBD | MBL2 | CXCL6 | ANGPTL1 | IGHV3-7 | PLEKHH3 | LOC400576 |
| CNTFR | HBE1 | MCAM | CXCL11 | MTMR4 | IGHV2-26 | ADAMTS20 | PRSS57 |
| COL1A1 | HBG2 | MDH1 | CXCL5 | INA | IGHV1-58 | SCUBE1 | VWC2L |
| COL1A2 | SERPIND1 | MECP2 | XCL1 | BMP15 | IGHV1-45 | PDGFD | OVOS |
| COL2A1 | HDGF | MEP1A | CX3CL1 | LGI1 | IGHV1-24 | WNT10A | SPINK14 |
| COL3A1 | HDLBP | MEP1B | SDCBP | IL32 | IGHV1-18 | ULBP2 | CCL3L3 |
| COL4A1 | HEXB | MFAP4 | CXCL12 | NOG | IGHV1-3 | BPIFB2 | DEFB103A |
| COL4A2 | CFH | MFGE8 | SDF2 | CRLF1 | TRDC | SPX | LOC439951 |
| COL5A1 | HFE | MELTF | SECTM1 | AIMP1 | TRBC2 | COL18A1 | CTRB2 |
| COL5A2 | CFHR1 | MFNG | SELE | MMP20 | TRBC1 | APOL4 | CDNF |
| COL6A1 | HGF | SCGB2A1 | SELP | CER1 | IGLV10-54 | WNT5B | IGFL4 |
| COL6A2 | HGFAC | KITLG | SEMA3F | SLIT2 | IGLV9-49 | AMN | POTEE |
| COL6A3 | HMGB1 | MIF | SEMG1 | ITGBL1 | IGLV8-61 | JAM3 | SPINK9 |
| COL7A1 | HMGB2 | CXCL9 | SEMG2 | KL | IGLV7-46 | INHBE | CBLN3 |

TABLE 1-continued

Non-exhaustive list of putative surrogate markers for the determination of the level of STAT3 activation

| | | | | | | | |
|---|---|---|---|---|---|---|---|
| COL8A1 | HMOX1 | MMP2 | SELENOP | ADIPOQ | IGLV5-52 | FGFBP2 | PYY3 |
| COL11A1 | HP | MMP3 | SFRP1 | LIPG | IGLV5-45 | EIF2A | LINGO3 |
| COL12A1 | HPGD | MMP7 | SFRP2 | ITM2B | IGLV5-39 | TMPRSS13 | SPINK8 |
| COL15A1 | HPR | MMP8 | SFRP4 | LY86 | IGLV5-37 | EMILIN2 | LYPD8 |
| COMP | HPX | MMP9 | SFRP5 | NAPSA | IGLV4-69 | LOXL4 | SERPINE3 |
| COPA | HRG | MMP10 | SFTPB | CABP1 | IGLV4-60 | C2orf40 | POTEI |
| CORT | HSPA1A | MMP12 | SFTPC | ADAMTS4 | IGLV4-3 | RAB11FIP4 | LGALS7B |
| CP | HSPA1B | MMP13 | SFTPD | ADAMTS3 | IGLV3-25 | COL25A1 | SFTPA1 |
| CPA1 | HSPA1L | MMP14 | SH3BGRL | ADAMTS2 | IGLV3-22 | IL1F10 | POTEJ |
| CPA2 | HSPA2 | MMP19 | SHH | GDF15 | IGLV3-21 | SPINK7 | MSMP |
| CPA3 | HSPA6 | MOV10 | SLC2A1 | CXCL14 | IGLV3-16 | RETNLB | MUC5B |
| CPB1 | HSPA7 | MPO | SLC4A1 | GDF3 | IGLV3-12 | LOXL3 | DEFA1B |
| CPB2 | HSPA8 | MSMB | SLIT1 | PRDX6 | IGLV3-10 | AIFM2 | POTEF |
| CPD | HSPB1 | MSN | SLIT3 | PDIA4 | IGLV2-18 | LINGO1 | SFTPA2 |
| CPE | HSPD1 | MSR1 | SLPI | CARTPT | IGLV1-47 | HIST1H2BK | PSAPL1 |
| CPM | HSPG2 | MST1 | SMARCA4 | CLCA3P | IGLV1-36 | KRT87P | LRRC70 |
| CPN1 | TNC | MT3 | SMPD1 | SEMA3E | IGLC7 | SSH2 | GKN3P |
| CPN2 | HYAL1 | NUDT1 | SNCA | FAM20B | IGKV6D-21 | TSLP | MOXD2P |
| CRH | IAPP | MUC1 | SOD1 | TNFSF15 | IGKV3D-20 | UMODL1 | IGLL5 |
| CRHBP | IBSP | MUC4 | SOD3 | FGFBP1 | IGKV3D-15 | SERPINB12 | APELA |
| CRP | ICAM1 | MUC5AC | SORD | IL18BP | IGKV3D-11 | SERPINB11 | MICA |
| CSF1 | ICAM4 | MYOC | SORL1 | GPC6 | IGKV3D-7 | WNT3A | ZNF559-ZNF177 |
| CEACAM5 | TUBB2A | IGLV3-19 | KRT5 | HUS1B | KRT80 | IFNL4 | LOC101060157 |
| KRT6B | IGLV1-40 | LDHA | TUBA4A | KRT6C | YWHAG | PROCR | TRAP1 |
| KRT76 | HIST1H1A | CFHR2 | REG1B | IGHV1OR21-1 | PPIAL4A | KRT24 | CSF1R |
| KRT12 | PGAM4 | VSIG4 | HSP90AB3P | PC | POTEKP | LOC642131 | C6 |
| F13B | REG1A | TUBA1A | TUBB4A | PLXDC2 | HSPH1 | KRT17 | IGLV3-27 |
| LDHB | SLC4A4 | KRT7 | KRT16 | KRT6A | TUBA3E | TUBB6 | KRT36 |
| SUCLG1 | TUBB | VIM | GTPBP8 | TNXA | ITLN2 | CEACAM1 | CENPQ |
| KRT71 | TKT | ANTXR1 | SRSF9 | GFAP | LYVE1 | LAMA3 | PPIAL4G |
| GAPDHS | NLRC5 | PGAM1 | ATP5A1 | EPHB4 | ITLN1 | KRT84 | LEKR1 |
| KRT74 | ICAM2 | TUBA1C | HIST1H1B | BCAM | BRSK1 | USO1 | HNRNPA1 |
| MAN1A1 | KRT38 | ABCB9 | KRT25 | FGFR1 | FCGBP | C2ORF72 | HBG1 |
| HIST1H1D | CDH5 | KRT37 | DSG2 | PLS1 | ITIH3 | TAGLN | HNRNPA1L2 |
| HSP90AB1 | VCL | YWHAB | GDI1 | KRT79 | KRT27 | EXOC3L4 | IGLV7-43 |
| G6PD | SLC4A5 | OSBPL11 | EPCAM | ESD | KRT13 | CD163 | KRT3 |
| KRT19 | CRTAC1 | PGLYRP2 | CD44 | ETFB | IGLV1-44 | USH1C | IFT74 |
| ARHGDIA | VWF | TUBB4B | GAPDH | KIAA0232 | DOCK10 | GPX6 | HBZ |
| PRG4 | IGHV4-59 | KRT15 | ANXA2P2 | TUBB2B | NUP214 | CA1 | KRT73 |
| HSPA9 | TGM4 | TUBA8 | GDI2 | IDH1 | YWHAH | CST7 | MXRA5 |
| TUBA1B | IGLV2-11 | LMNA | S100A6 | PRDX2 | CRIP1 | RXRB | PI16 |
| PLS3 | STX17 | YWHAQ | TUBB8 | CD248 | MCM5 | EEF1A2 | SYNE2 |
| C7 | MYO19 | KRT4 | GSTO1 | HIST1H1T | KRT77 | KRT8 | CFHR5 |
| CPS1 | MMP11 | KRT75 | DCD | HIST1H1C | ADH5 | KRT14 | ALDOC |
| KPNA2 | KRT82 | KRT28 | KRT32 | SHBG | FCGR3A | CNDP1 | RARRES1 |
| TUBA3C | YWHAE | IGK@ | HNRNPA2B1 | FYCO1 | KRT18 | FNDC3A | THBS3 |
| PGK2 | NEFH | UBA1 | HIST1H1E | METTL18 | FCGR3B | PGAM2 | ALDOB |
| IGLV6-57 | KRT72 | CAD | TLN1 | HSPA5 | CFD | NEB | PLGLA |
| CD24 | CD26 | CD147 | FGF7 | FGF19 | TNFRSF8 | RLN2 | BDNF |
| RAGE | TIM3 | HSP90AA1 | GP1BA | | | | |

FIG. 19*a* provides an overview of the p-STAT3 surrogate markers selection workflow. Briefly, and as previously mentioned, STAT3-related genes were identified from Kyoto Encyclopedia of Genes and Genomes (KEGG) database by compiling all genes that are involved in known STAT3 pathways. Secreted STAT3-related proteins were selected based on extracellular genes listed in NCBI's Biosystems database and proteins identified in mass spectrometry analysis of cell-free ascites. Transcriptomics comparison was performed using two databases to prioritize putative STAT3 surrogate markers. Database 1 was used to determine genes that are positively correlated with STAT3 in The Cancer Genome Database (TCGA) colorectal cancer (COAD-READ) data set. Genes were ranked from the most positively correlated to least correlated with STAT3. Database 2 was derived from microarray analysis of PAI-1 paracrine addicted (PPA) cell-free ascites-treated cells exposed to TM5441 to determine genes that are downregulated and upregulated in PAI-1 paracrine addicted (PPA) cell-free ascites-treated cells in response to TM5441 (PAI-1 inhibition). Upregulated genes were also of interest as these were thought to represent genes that are involved in rescue mechanisms in response to PAI-1 inhibition. Similarly, genes were ranked from most downregulated to most upregulated. Systematic paired correlation analysis of candidate genes was subsequently performed by focusing on top 1% and 25% of genes positively correlated with STAT3 in database 1, and top 1% and 25% of most downregulated and upregulated genes in database 2. The paired analysis for each group were prioritised as shown in FIG. 19*b*, and representative genes were chosen from each group based on literature review to reduce the list of potential targets to 35 genes. Ten targets were selected based on rank prioritisation, potential good correlation with p-STAT3 from Luminex assay data, and the importance of the candidate genes in cancer pathogenesis from literature review for further evaluation with enzyme-linked immunosorbent assay (ELISA). The concentrations of each surrogate marker in cell-free ascites were correlated with p-STAT3 levels in cell-free ascites-treated cells using Spearman correlation analysis.

Thus, the surrogate markers disclosed herein can be selected based on their correlation to STAT3. The surrogate markers disclosed herein can also be selected based on their up- or down-regulation compared to the same markers in cell-free ascites-treated samples or in negative controls. Once ranked, for example by prevalence, priority, or any other criteria, these markers can be, but are not limited to, the top 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of all the markers listed based on the above criteria. For example, markers can be selected for being in the top 1% of markers which positively correlate with STAT3. In another example, markers can be selected for being in the top 1% of markers which negatively correlate with STAT3 phosphorylation. As used herein, a positive correlation refers to a proportional relationship between a surrogate marker and its target. A negative correlation therefore refers to an anti-proportional (or inverse) relationship between a surrogate marker and its target. For example, a positive correlation means that an increase in target concentration results in an increase in surrogate marker concentration. A positive correlation can also mean that a decrease in target concentration results in a decrease in surrogate marker concentration. Conversely, a negative correlation means that an increase in target concentration results in a decrease in surrogate marker concentration. Markers can also be selected for being in the top 1% or 25% of markers which are up-regulated or down-regulated compared to a control or any other benchmark.

In another example, surrogate markers are selected based on their up- and/or down-regulation. Such an up- or down-regulation can be determined based on the level of such markers in, for example, samples which have been treated with a PAI-1 inhibitor.

A person skilled in the art will readily appreciate that markers can be chosen for reasons and criteria other than listed herein, for example, markers that do not show any apparent correlation to STAT3 but were shown to have a significant effect on for example, a multivariate analysis. It is also appreciated that multiple criteria can be applied to the initial marker pool in order to narrow down and obtain a final list of, for example, surrogate markers.

Out of the 10 targets selected, five exemplary candidate surrogate markers (IL6, IL10, CCL2, MMP9, and ANGPT1) were validated on 70 patient samples and successfully identified an exemplary composite biomarker panel. As an example, such a composite biomarker panel can consist of four targets (IL6, CCL2, IL10, and MMP9) as surrogate biomarkers of STAT3. This exemplary panel has an overall accuracy of 92.86%.

In addition, five candidate surrogate markers (TGFB1, POSTN, VSIG4, CD44, and CXCL10) were validated in 40 patient samples, which resulted in the results as shown in FIG. 21. This exemplary composite biomarker panel resulted in an area under the curve (AUC) value of 0.83 (P=0.001). Combining IL6 with this composite biomarker panel, an area under the curve (AUC) of 0.98 (P<0.0001) was obtained.

Thus, in one example, the surrogate markers can be, but are not limited to, one or more of the following: LUM, ANGPT1, IL1B, POSTN, TNC, MMP9, MMP2, TIMP3, DCN, VSIG4, CXCL5, CD36, ANGPT2, SERPINB5, IL6, CCL2, LEP, VCAM1, CCL8, ITGAM, THBS1, FN1, COL5A1, MXRA5, C3, CXCL10, TGFB1, CD44, TIM3, TNFSF13B, CEACAM1, LAMB1, IL10, IL5, IL22. In yet another example, the surrogate markers can be, but are not limited to, one or more of the following: IL6, IL10, CCL2, MMP9, ANGPT1, TGFB1, POSTN, VSIG4, CD44, and CXCL10. In a further example, the surrogate markers can be, but are not limited to, one, or more, or all, of the following: IL6, IL10, CCL2, MMP9 and ANGPT1. In another example, the surrogate markers can be, but are not limited to, one, or more, or all, of the following: IL6, IL10, CCL2, and MMP9. In another example, one of the surrogate markers is IL6. In yet another example, the combination, or group, or panel of surrogate markers used comprises IL6.

Thus, in one example, the surrogate markers are, but are not limited f IL6, IL10, CCL2, MMP9, ANGPT1, TGFB1, POSTN, VSIG4, CD44, and CXCL10. In another example, the surrogate markers are, but are not limited to, IL6, IL10, CCL2, MMP9 and ANGPT1. In yet another example, the surrogate markers are, but are not limited to, IL6, IL10, CCL2, and MMP9. In a further example, the surrogate markers comprise IL6, IL10, CCL2, MMP9 and ANGPT1. In another example, the surrogate markers comprise at least IL6, IL10, CCL2, and MMP9. In a further example, the surrogate markers are, but are not limited to, IL6, TGFB1, POSTN, VSIG4, CD44, and CXCL10. In yet another example, the surrogate markers are, but are not limited to, TGFB1, POSTN, VSIG4, CD44, and CXCL10.

The conclusion drawn from this group of patients is that the cell-free ascites (collected from a subgroup of patients) activates other signalling pathways thereby sustaining cancer cells. It was further noted that there appeared to be an absence of any cell-free ascites with high PAI-1 levels that is associated with low levels of STAT3 phosphorylation, when established cell line models are exposed to these cell-free ascites. This further shows that PAI-1 activates STAT3. In the unlikely event that this statement is not true, one would observe ascitic samples with high PAI-1 levels that do not activate STAT3 signalling when cells are exposed to these cell-free ascites. However, the method disclosed herein is supported and underlined by the fact that ascitic samples with high PAI-1 levels do activate STAT3 signalling when cells are exposed to these cell-free ascites. Taken together, a subset or subgroup of patients was identified, who had cell-free ascites with high PAI-1 levels that had been shown to drive STAT3 activation of cancer cells. Without being bound by theory, it was thought that if paracrine STAT3 activation of cancer cells is dependent on PAI-1 levels within these ascites, this would lead to a phenomenon of oncogenic addiction to a single upstream ligand. That is to say that patients whose cell-free ascites have high PAI-1 and activated STAT3 signalling when cells are considered to be highly susceptible to ligand inhibition of PAI-1 in ascites. This ligand inhibition of PAI-1 can be performed by, for example, intraperitoneal instillation of a PAI-1 inhibitor.

Figure 11:
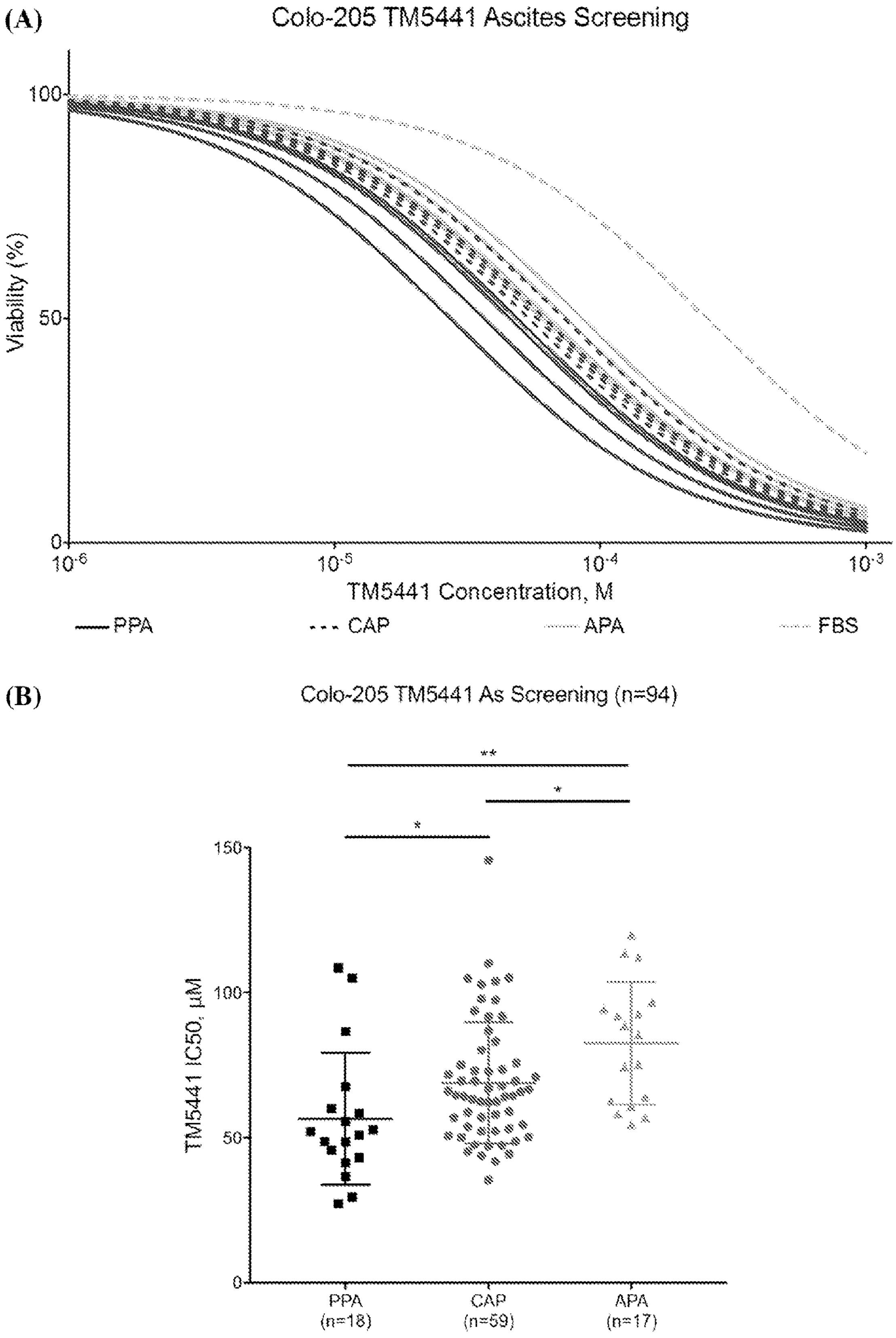
FIG. 11 shows the effect of TM5441 (PAI-1 inhibitor) on the three distinct groups of cell-free ascites-treated Colo-205 cells. (A) Representative inhibitor dose-response curves of PAI-1 paracrine addicted (PPA) group (black solid line), co-activators predominant (CAP) group (black dotted line), alternative pathways activation (APA) group (grey solid line), and foetal bovine serum (FBS; control, grey dotted line) demonstrated a left shift in dose-response curve, indicating responsiveness to PAI-1 inhibition. (B) Differential sensitivity of cell-free ascites to TM5441 corresponding to the three distinct group, with PAI-1 paracrine addicted (PPA) (n=18) being the most sensitive to PAI-1 inhibition, followed by co-activators predominant (CAP) (n=59) and alternative pathways activation (APA) (n=17). (C) Cohort of cell-free ascites used in this analysis.

Next, Colo-205 (an established cell line model of colorectal peritoneal carcinomatosis) was systematically exposed to cell-free ascites collected from patients before subjecting these cells to treatment with TM5441 (PAI-1 inhibitor). As shown in FIG. 11, paracrine activation of Colo-205 led to a differential sensitivity to TM5441. Ascites collected from patients, of which it was thought that the STAT3 activation in cancer cells is dependent on PAI-1 levels within cell-free ascites, were most susceptible to inhibition with TM5441, confirming the finding that cancer cells exposed to these cell-free ascites were oncogenically addicted to PAI-1. In other words, the data shown here indicates that when cells are exposed to cell-free ascites belonging to, for example, the PAI-1 paracrine addicted (PPA) group, these cells are dependent on the ascites to activate STAT3 signalling within them. When PAI-1 is blocked (ligand inhibition) within the cell-free ascites, STAT3 signalling within the cells is inhibited and the cells die. Cells exposed to co-activators predominant (CAP) group cell-free ascites, for example, are less reliant on PAI-1 for STAT3 activation, however a response is still possible. Concurrently, cells exposed to alternative pathways activation (APA) group cell-free ascites are not reliant on PAI-1 and do not activate STAT3, and are therefore not susceptible to PAI-1 inhibition.

Thus, in one example, there is disclosed a method of detecting or detecting susceptibility of a subject suffering from peritoneal carcinomatosis to treatment with a PAI-1 inhibitor, the method comprising determining the concentration of plasminogen activator inhibitor 1 (PAI-1) and determining the level of phosphorylation of "signal transducer and activator of transcript 3" (STAT3) in a sample obtained from a subject; wherein the subject is susceptible to treatment if the subject shows (a) an increase in PAI-1 concentration and an increase in STAT3 phosphorylation, or (b) a decrease in PAI-1 concentration and an increase in STAT3 phosphorylation; wherein the increase and/or decrease is compared to the concentration of PAI-1 and the level of STAT3 phosphorylation measured in a sample obtained from a reference group.

Validation in in vivo mouse models using cell-free ascites that activates paracrine STAT3 signalling via PAI-1 demonstrated sensitivity to intra-peritoneal instillation of TM5441 (FIG. 14, FIG. 15 and FIG. 17). Some examples of PAI-1 inhibitors have been shown to bind to the s4A in PAI-1. The precursors of the PAI-1 inhibitor were identified by in silico virtual screening based on the 3D conformation of s4A position (Izuhara et al., Arterioscler Thromb Vasc Biol. 2008; 28:672-677). The docking models of these precursors to s4A position of PAI-1 have been previously reported (Izuhara et al., Journal of Cerebral Blood Flow & Metabolism (2010) 30, 904-912). In one example, the PAI-1 inhibitor binds to the s4A position in PAI-1. In another example, the PAI-1 inhibitor is an anti-cancer treatment or anti-cancer drug. In another example, administration of the PAI-1 inhibitor, as disclosed herein, leads to inhibition of PAI-1 activity compared to patients suffering from the same disease.

In yet another example, the anti-cancer treatment or anti-cancer drug is, but is not limited to, a small molecule, a chemotherapeutic agent, a peptide, an antibody, combinations thereof, and combination therapy. In another example, the anti-cancer drug is, but is not limited to, TM5441 (5-Chloro-2-[[2-[2-[[3-(3-furanyl)phenyl]amino]-2-oxoethoxy]acetyl]amino]benzoic acid sodium salt; CAS 1190221-43-2), TM5007 (N, N-bis [3,3'-carboxy-4,4'-(2,2'-thienyl)-2,2'-thienyl]hexanedicarboxamide; CAS 342595-05-5), TM5275 (5-Chloro-2-[[2-[2-[4-(diphenylmethyl)-1-piperazinyl]-2-oxoethoxy]acetyl]amino]-benzoic acid sodium salt; CAS 1103926-82-4), Tiplaxtinin (2-(1-Benzyl-5-(4-(trifluoromethoxy)phenyl)-1H-indol-3-yl)oxoacetic acid; CAS 393105-53-8), ZK4044, and derivatives thereof. Example structures of the various anti-cancer drugs are shown below:

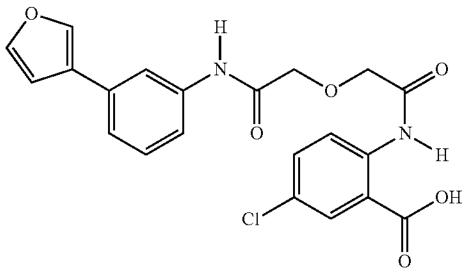

TM5441

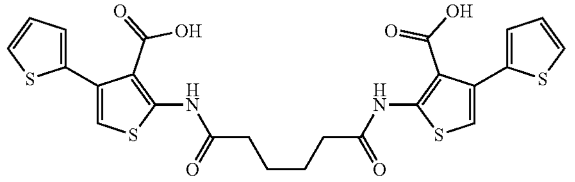

TM5007

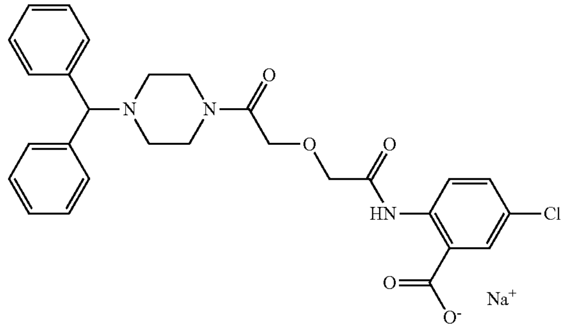

TM5275

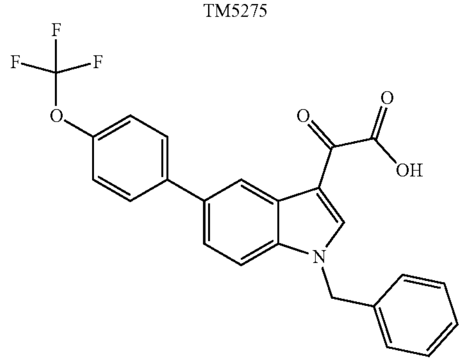

Tiplaxtinin

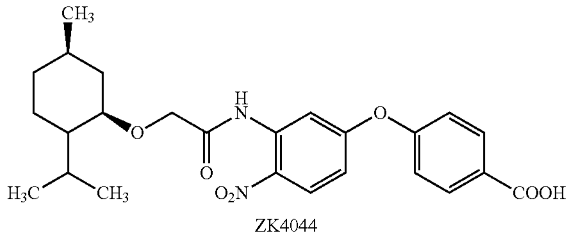

ZK4044

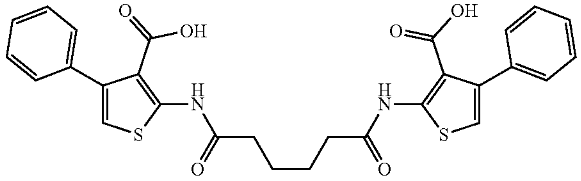

TM5001

In another example, the PAI-1 inhibitor is administered intraperitoneally.

In another example, there is disclosed a panel of markers for treating a patient suffering from peritoneal carcinomatosis with a "plasminogen activator inhibitor 1" (PAI-1) inhibitor, or for detecting or determining susceptibility of a subject suffering from peritoneal carcinomatosis to a treatment with a "plasminogen activator inhibitor 1" (PAI-1) inhibitor, wherein the panel of markers comprises PAI-1, and one or more surrogate markers of STAT3 phosphorylation or p-STAT3. In on example, the use of a panel of markers in the method as referred to herein is disclosed, wherein the panel comprises PAI-1 and one or more surrogate markers of STAT3 phosphorylation, or PAI-1 and p-STAT3. In one example, the panel comprises PAI-1 and one or more or all of IL6, IL10, CCL2, and MMP9. In another example, the panel comprises PAI-1, and one or more or all of IL6, IL10, CCL2, MMP9 and ANGPT1. In yet another example, the panel comprises PAI-1, and one or more or all of TGFB1, POSTN, VSIG4, CD44, and CXCL10. In a further example, the panel comprises PAI-1, and one or more or all of IL6, TGFB1, POSTN, VSIG4, CD44, and CXCL10.

In another example, there is disclosed use of a PAI-1 inhibitor in the manufacture of a medicament for treating peritoneal carcinomatosis, wherein the medicament is to be administered to a subject determined to belong to a patient group determined to be susceptible to PAI-1 inhibitor treatment. In another example, the susceptibility of a subject is determined by measuring the concentration of PAI-1 and STAT3 phosphorylation (p-STAT3), as disclosed herein, and comparing the measured values to cut-off values as disclosed herein.

In the context of this invention the term "administering" and variations of that term including "administer" and "administration", includes contacting, applying, delivering or providing a compound or composition of the invention to an organism, or any relevant surface by any appropriate means.

In As used herein, the term "treatment" refers to any and all uses which remedy a disease state or symptoms, prevent the establishment of disease, or otherwise prevent, hinder, retard, or reverse the progression of disease or other undesirable symptoms.

In the context of this specification, the terms "therapeutically effective amount" and "diagnostically effective amount", include within their meaning a sufficient but non-toxic amount of a compound or composition of the invention to provide the desired therapeutic or diagnostic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

In vitro validation with Tiplaxtinin (PAI-1 inhibitor) highlights that inhibition of PAI-1 Michaelis complex is the potential mechanism of how cells are oncogenically addicted to PAI-1. Treatment with Napabucasin (STAT3 inhibitor) highlights that STAT3 inhibition alone is not useful as the Michaelis complex likely activates other signalling cascade in addition to STAT3 signalling. Treatment with dual PI3K/mTOR inhibitor or Mitomycin C (induces DNA damage) highlights the absence of utility of these drugs when cancer cells are exposed to paracrine activation driven by ascites (FIG. 12). Thus, in one example, the concentration of PAI-1 is determined by measuring the concentration of PAI-1 to urokinase-type plasminogen activator (uPA)/tissue-type plasminogen activator (tPA) complex. In another example, the concentration of PAI-1 is determined by measuring the concentration of PAI-1 in cell-free ascites. In another example, the concentration of PAI-1 is determined by measuring PAI-1 in its active and/or latent forms and/or complexes with, including but not limited to, urokinase-type plasminogen activator (uPA), tissue-type plasminogen activator (tPA), vitronectin and combinations thereof. In another example, the concentration of PAI-1 is determined by measuring the concentration of PAI-1 directly, or in one or more complexes. That is to say that PAI-1 need not be in a complex with, for example urokinase-type plasminogen activator (uPA)/tissue-type plasminogen activator (tPA) or other proteins to result in downstream effects. In yet another example, the level of STAT3 phosphorylation is determined by measuring the p-STAT3 level in established cell line models of colorectal peritoneal carcinomatosis. In one example, the cell line models of colorectal peritoneal carcinomatosis are treated with cell-free ascites. In a further example, the level of STAT3 phosphorylation is determined by measuring the p-STAT3 level in established cell line models of colorectal peritoneal carcinomatosis treated with cell-free ascites.

In another example, there is disclosed a method of treating a subject suffering from peritoneal carcinomatosis with a PAI-1 inhibitor, the method comprising determining the concentration of plasminogen activator inhibitor 1 (PAI-1) and determining the level of phosphorylation of "signal transducer and activator of transcript 3" (STAT3) in a sample obtained from the subject; administering the PAI-1 inhibitor to the subject showing (a) an increase in PAI-1 concentration and an increase in STAT3 phosphorylation, or (b) a decrease in PAI-1 concentration and an increase in STAT3 phosphorylation; wherein the increase and/or decrease is compared to the levels of PAI-1 and STAT3 phosphorylation measured in a sample obtained from a reference group.

In one example, the PAI-1 inhibitor is an anti-cancer drug.

In the methods disclosed herein, the reference group refers to a group of subjects suffering from peritoneal carcinomatosis. In another example the reference group is a group of patients who are not suffering from peritoneal carcinomatosis, but who present with benign tumours.

Comparison of values obtained in the experiments disclosed herein result in the definition of reference values as disclosed herein (also referred to as cut-off values), which have been determined for each of the markers to be measured. The comparison between the measured values and the cut-off values can be done in a relative, qualitative manner (for example, that the concentration of one marker is more or less than the concentration of other marker) or in a quantitative manner (for example, value X is compared to value Y). Due to the nature of measurements, reference values or cut-off values can also include a buffer around the specific values. For example, a cut-off value with a 2% buffer means that if the cut-off value is 10, the buffer would result in a range of 9.8 to 10.2 being allowable for measurements. Depending on the context of the cut-off value, a buffer can also be applied in only one direction. For example, if the cut-off value is at least 10, then a buffer of 2% would result in a value of 9.8 also being acceptable. If the cut-off value is no more than 10, then a buffer of 2% would result in a value of 10.2 also being acceptable. In another example, the buffer can be 3%, 4% or 5% of the cut-off value in question. In another example, the buffer is 5% of the cut-off value in question. In another example, the buffer is 2% of the cut-off value in question.

Also envisioned in the scope of the present application is a system for detecting the markers, surrogate or otherwise, disclosed herein. For example, such a detection system is to be capable of diagnosing or detecting or predicting the likelihood of a patient or subject having peritoneal carcinomatosis. Accordingly, the biomarkers as described herein can be incorporated in diagnostic tools, detection systems, methods of diagnosis, methods of predicting or methods of determining the likelihood of a patient having peritoneal carcinomatosis. Exemplary detection system can comprise, for example, a receiving section to receive a sample from a patient suspected to suffer from peritoneal carcinomatosis, wherein the sample is suspected to comprise one or more biomarkers of the present disclosure, and a detection section comprising a substance or substances capable of detecting one or more biomarkers of the present disclosure. The samples used in this system can be, but are not limited to, the sample types disclosed here.

To assist in detecting the biomarkers of the present disclosure, the detection system can comprise a substance capable of binding or specifically binding to any of the biomarkers disclosed herein. For example, such substances can be biospecific capture reagents such as antibodies (or antigen-binding fragments thereof), interacting fusion proteins, aptamers or affibodies (which are non-immunoglobulin-derived affinity proteins based on a three-helical bundle protein domain) that recognize the biomarker and/or variants thereof. In use, the substance can, for example, be bound to a solid phase, wherein the biomarkers can be detected methods known in the art, for example, mass spectrometry, or by eluting the biomarkers from the biospecific capture reagents and detecting the eluted biomarkers using methods known in the art, for example, a traditional matrix-assisted laser desorption/ionization (MALDI) or by surface-enhanced laser desorption/ionization (SELDI). For example, the detection system comprised on a biochip, test strip, or microtiter plate.

A companion biomarker that dictates therapy based on the concept of oncogenic addiction in peritoneal carcinomatosis patients has been identified. The biomarker that has been identified that activates STAT3 and other signalling pathways is part of the coagulation cascade. In other words, activation of the coagulation cascade after surgery can stimulate growth of cancer cells. It is further thought that hyper-activation of coagulation or the fibrinolytic cascade is oncogenic and inhibition of these two processes has shown potential therapeutic relevance. In addition, gene expression profiling of 2 colorectal peritoneal carcinomatosis cell lines treated with cell-free ascites revealed activation of STAT3 signalling. Furthermore, validation experiments on cell-free ascites (n=13) demonstrated STAT3 to be most relevant in colorectal peritoneal carcinomatosis. Clinically, colorectal cancer patients in the TCGA database (n=345) with STAT3 and epithelial-mesenchymal transition (EMT) activation had poorer prognosis. Interestingly, receptor tyrosine kinase arrays showed no phosphorylation of JAK kinase, suggesting non-canonical activation of STAT3 signalling. Cytokine array and mass spectrometry identified potential STAT3 activating ligands independent of JAK kinase including POSTN, CD24, and CD44. Treatment of cell lines exposed to cell-free ascites demonstrated sensitivity to inhibitors of upstream non-canonical STAT3 activator in in vitro and in vivo settings.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used in this application, the singular form "a," "an," and "the" include plural references unless the context clearly dictates otherwise. For example, the term "a genetic marker" includes a plurality of genetic markers, including mixtures and combinations thereof.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Materials and Methods

Patient Recruitment, Biospecimen Collection and Processing

Patients who were undergoing treatment for peritoneal carcinomatosis at the National Cancer Centre Singapore were identified and recruited. Informed consent was obtained from all patients in accordance to study protocol approved by the SingHealth Centralized Institutional Review Board (CIRB Ref: 2015/2479/F). All experiments were performed in accordance with the relevant guidelines and regulations. Tumour specimens harvested post-operatively were systematically divided into multiple pieces. One portion was snap-frozen in liquid nitrogen immediately and stored in −80 °C freezer while another was fixed in formalin to construct formalin-fixed paraffin embedded (FFPE) block. Remaining tissues were processed in the laboratory to establish primary cell lines and patient derived xenografts. Ascites collected from the peritoneal cavity at the beginning of the cytoreductive surgery (CRS) or during routine ascites tap (paracentesis) was subjected to centrifugation at 2000 g for 10 minutes to separate the cellular and fluid component. Filter-sterilization using 0.22 μm filter was performed on the fluid component to render it suitable for downstream experiments. The cellular component of ascites was used for downstream assays and the generation of patient-derived ascites-dependent xenograft (PDADX) models.

Cell Lines

Human metastatic colon cancer cell line Colo-205 and SNU-C1 were purchased from American Type Culture Collection and cultured in RPMI medium with 10% foetal bovine serum (FBS), 1% penicillin-streptomycin and 1% antimycotic. Human normal peritoneal mesothelial cell lines LP9/TERT and HM3/TERT were purchased from Brigham and Women's Hospital Cell Culture Core and cultured in M199/M106 with 15% iron-supplemented new-born calf serum, 0.4 μg/mL hydrocortisone, 10 ng/mL epidermal growth factor, 1% penicillin-streptomycin and 1% antimycotic. All cells were grown in serum-free medium for overnight prior to experiments.

Primary Clinical Endpoint

The primary clinical endpoint was overall survival (OS). OS is defined as the time from surgery to death, regardless of cause. Kaplan-Meier curves were plotted to compare 5-year overall survival (OS) by the presence or absence of ascites. Presence of ascites is defined by accumulation of more than 50 mL fluid in the abdominal cavity. Log-rank test was used to determine statistical significance for curve comparison.

Proliferation Assay

A total of 5000 cells/wells were seeded in 96-well plates and were grown in serum-free RPMI medium supplemented with varying concentration of cell-free ascites. Cell proliferation was assessed using CellTitreGlo assay (Promega, Madison, US) at day 0 and day 5. These experiments were performed in triplicates and repeated 3 times.

Cell Migration Assay

Colo-205 or SNU-C1 cells were serum starved for 24 hours and subsequently treated with 3 different cell-culture media: serum-free RPMI, RPMI supplemented with 10% foetal bovine serum (FBS), or serum-free media supplemented with 5% cell-free ascites for 24 hours. Pre-treated cells were then seeded into 6-well transwell migration assay at a density of 600,000 cells/well. The inner chamber of the transwell plate was filled with serum-free media and the outer chamber was filled with 10% foetal bovine serum (FBS) media. Cells were allowed to migrate for 24 hours. These experiments were performed in triplicates and repeated 3 times.

Cell Settlement Assay

A total of 70,000 cells/well of LP9/TERT or HM3/TERT were seeded in 12-well plates and were grown to confluency in complete media to form the feeder layer. Subsequently, the mesothelial feeder layer was serum starved prior to co-culture with cancer cells. 35,000 cells/well of Colo-205 or SNU-C1 were seeded into each well in 3 different medium: serum-free RPMI, RPMI supplemented with 10% foetal bovine serum (FBS), or serum-free RPMI supplemented with 5% cell-free ascites, and incubated for 24 hours. Non-attached cancer cells were removed by gentle washing with complete media for 5 times. The average number of cells settled in three fields per well was counted. The final number of cells settled was determined by the mean of triplicate assays.

Gene Expression Profiling

To assess signalling pathways upregulated upon treatment with cell-free ascites, Colo-205 and SNU-C1 cells were treated with 5% and 0.1% cell-free ascites for 24 hours. To assess signalling pathways affected by PAI-1 inhibition, Colo-205 cells were treated with cell-free ascites representative of PAI-1 paracrine addicted (PPA) group, co-activators predominant (CAP) group or foetal bovine serum (FBS; control) in the presence of DMSO vehicle or 27.25 μM TM5441 for 24 hours. Total RNA was isolated using Qiagen Mini Kit (Qiagen, CA, USA), following the manufacturer's instructions. Gene expression profiling was performed using Affymetrix GeneChip Genome U133 Plus 2.0 microarray platform (Affymetrix, Santa Clara, CA) in accordance to manufacturer's protocols. Microarray data was uploaded into the free programming software R (R Foundation for Statistical Computing, Vienna, Austria) for processing and normalization. Gene Set Enrichment Analysis (GSEA) was used to assess enrichment of genes showing up- and down-regulation using GSEA graphical user interface (GUI) software (broadinstitute.org/gsea/).

Protein Immunoblotting

Colo-205 or SNU-C1 cells were starved in serum-free media overnight before treating with 5% of patients' cell-free ascites for 24 hours. On the next day, cells were harvested and lysed in M-PER (Mammalian Protein Extraction Reagent, Thermo Scientific Inc.) supplemented with Pierce Protease and Phosphatase Inhibitor (Thermo Scientific Inc.) for 1 hour on ice. The lysates were centrifuged at 14,000 g for 20 minutes at 4 °C to obtain clear supernatants. Protein concentrations were determined using the Bradford protein assay reagent (Bio-Rad). Specific amount of proteins were calculated (5 μg for STAT3 and actin; 25 μg for phospho-STAT3 (Tyr705) and phospho-STAT3 (Ser727); 10 μg for JAK1, JAK2, phospho-JAK1 (Tyr1022/Tyr1023) and phospho-JAK2 (Tyr1007/Tyr1008)) and aliquoted into 0.2 mL thin wall PCR tubes. Lysates were denatured at 97 °C for 5 minutes and resolved in 10% polyacrylamide gels in Tris/glycine/SDS running buffer (24.76 mM Tris, 191.83 mM glycine and 0.1% SDS) and the transferred to 0.45 μm nitrocellulose membrane (Bio-Rad) in Tris/glycine/methanol transfer buffer (24.76 M Tris, 191.83 mM glycine and 20% methanol). The membranes were blocked with 5% non-fat milk in 1×PBS containing 0.1% TWEEN™ 20 (polysorbate 20) (PBST) for 1 hour at room temperature before blotting with primary antibodies for 1.5 hours. Dilutions of the primary antibodies were: 1:2,000 STAT3 (Cell Signaling Technology; #4904); 1:1,000 phospho-STAT3

(Tyr705) (Cell Signaling Technology; #9145); 1:1,000 phospho-STAT3 (Ser727) (Cell Signaling Technology; #94994); 1:1,000 JAK1 (Santa Cruz Biotechnology; sc-277); 1:1,000 phospho-JAK1 (Tyr1022/Tyr1023) (Santa Cruz Biotechnology; sc-16773); 1:1,000 JAK2 (Santa Cruz Biotechnology; sc-294); 1:1,000 phospho-JAK2 (Tyr1007/Tyr1008) (Santa Cruz Biotechnology; sc-16566) and 1:100,000 β-actin (Sigma Aldrich; A1978). After 4 washes (5 min per wash) in PBST, the blots were incubated with anti-rabbit or anti-mouse horseradish perioxidase (HRP)-linked secondary antibody (GE Healthcare Life Sciences; NA934 or NA931) for 30 minutes at room temperature. After another 4 washes in PBST, Peirce SuperSignal West Dura Extended Duration Substrate (Thermo Scientific Inc.) was added to the blots and incubated for 5 minutes at room temperature. Excess liquid was dripped off and the blots were wrapped in polyethylene for exposure to UltraCruz® Autoradiography Film (Santa Cruz Biotechnology, CA). Images were scanned using GS-800 ™ calibrated densitometer (Bio-Rad).

Immunohistochemistry (IHC)

Formalin-fixed paraffin-embedded (FFPE) specimens from peritoneal carcinomatosis (PC) cases with matched primary tumour and metastases were identified and interrogated using chromogen-based immunohistochemical (IHC) staining. All immunohistochemical (IHC) staining was carried out using the Bond Max Autostainer (Leica Microsystems, Ltd, Milton Kynes, UK) in accordance to the manufacturer's recommendations. Formalin-fixed paraffin-embedded (FFPE) blocks were sectioned into 4 µm thick sections and mounted on slides. Rabbit monoclonal anti phospho-STAT3 (Tyr705) (#9145L, Cell Signalling Technology, Massachusetts, US, 1:50, pH9, 30 minutes) was optimized and used. Slides were evaluated by two independent scorers, who had no prior knowledge of the clinical data, and staining results were determined based on the percentage of positive staining within the tumour epithelial component in each slide. Formalin-fixed paraffin-embedded (FFPE) samples were also collected from patient-derived ascites-dependent xenograft (PDADX) tumours and probed with antibodies against CK7, CK20 and CDX2 to confirm histology and origin of patient-derived ascites-dependent xenograft (PDADX) tumours formed. Rabbit monoclonal anti-CK7 (#31-1167-00, RevMab Biosciences, California, US, 1:200, pH9, 20 minutes), rabbit polyclonal anti-CK20 (HPA024309, Sigma Aldrich, Missouri, US, 1:200, pH9, 20 minutes) and rabbit monoclonal anti-CDX2 (#12306, Cell Signaling Technology, Massachusetts, US, 1:100, pH 9, 20 minutes) were optimized and used in the immunohistochemical (IHC) staining.

Mass Spectrometry

Mass spectrometry was performed on proteins isolated from the soluble and exosomal components of cell-free ascites from patients with benign serous cystadenofibroma (n=1) and malignant cell-free ascites from patients with colorectal peritoneal carcinomatosis (n=3). Briefly, liquid chromatography coupled with tandem mass spectrometry (LC-MS/MS) analysis of digested peptides was carried out using a Thermo Scientific Inc. Orbitrap Elite and QExactive mass spectrometers (Bremen, Germany) coupled with a Dionex UltiMate 3000 UHPLC system from Thermo Scientific Inc.

Cytokine Profiling

Proteome Profiler Human Cytokine array (ARY022B, R & D Systems, Minneapolis, US) consisting of 105 cytokines were used to profile plasma (n=1), benign cell-free ascites from patients with benign serous cystadenofibroma (n=1) and malignant cell-free ascites from patients with colorectal peritoneal carcinomatosis (n=4), gastric peritoneal carcinomatosis (n=1), and ovarian peritoneal carcinomatosis (n=1). Concentration of proteins in all fluids was quantified with Bradford protein assay (Biorad, Hercules, US) and equal amount of proteins were incubated with the membrane array following the manufacturer's instructions.

Epithelial-Mesenchymal Transition (EMT) Gene Profiling

Epithelial-Mesenchymal transition (EMT) gene profiling was performed using RT2 Profiler PCR Arrays (Qiagen, CA, USA) comprising 84 EMT-related genes. RNA was extracted from Colo-205 and SNU-C1 cells grown in complete media and 5% cell-free ascites for 24 hours using RNeasy extraction kit (Qiagen). cDNA was synthesized using RT2 First Strand kit (Qiagen) and reverse-transcription polymerase chain reaction was performed using RT2 SYBR Green Mastermixes (Qiagen). The results were analysed using Qiagen's Gene Globe Data Analysis Centre tool.

Phospho-Receptor Tyrosine Kinases (RTKs) Profiling

Profiling of phosphorylation of receptor tyrosine kinases (RTKs) was performed using human RTK phosphorylation antibody array (RayBiotech, GA, USA) which allows simultaneous detection of relative phosphorylation levels of 71 different human RTKs in cell lysate. Proteins were extracted from cell lysates of Colo-205 and SNU-C1 that were treated with 5% cell-free ascites or 10% foetal bovine serum (FBS) for 24 hours. Total protein concentration was determined with Bradford protein assay (Biorad, Hercules, US) and 40 pg of protein was used for phospho-RTKs profiling following the manufacturer's instructions.

The Cancer Genome Database (TCGA) Survival Analysis

Kaplan-Meier overall survival (OS) curve analysis was used to determine prognostic significance of PAI-1, STAT3 and epithelial-mesenchymal transition (EMT) regulation in The Cancer Genome Database (TCGA) colorectal adenocarcinoma (COADREAD) data set (n=345). Patients were stratified high (P+, 3.071) or low (P−, <3.071) PAI-1 expression, high (S+, ≥0.074) or low (S−, <0.074) STAT3 expression, and high (E+, ≥0.096) or low (E−, <0.096) epithelial-mesenchymal transition (EMT) expression based on cut-offs determined by recursive partitioning. Four subtypes (P−S−E+, P+S−E−, P+S−E+, P+S+E−) were excluded from analysis due to small sample size (n<20). Log-rank test was used to test for statistical significance.

Enzyme-Linked Immunosorbent Assay (ELISA)

Concentrations of PAI-1 (DSE100), IL6 (D6050), IL10 (D1000B), CCL2 (DCP00), MMP9 (DMP900), ANGPT1 (DANG10), TGFB1 (DB100B), and CXCL10 (DIP100) in cell-free ascites were quantified using human Quantikine ELISA kits from R & D Systems. Concentrations of POSTN (DY3548B) and CD44 (DY7045-05) in cell-free ascites were quantified using human DuoSet ELISA kits from R & D Systems. VSIG4 (ELH-VSIG4-1) concentration in cell-free ascites was quantified using ELISA from RayBiotech. All samples were performed with 2 technical replicates according to the manufacturers' instructions. Total STAT3 and phospho-STAT3 (Tyr705) were detected with ELISA (7305C and 7300C, Cell Signalling Technology, Massachusetts, US). Proteins were isolated from cell lysates of Colo-205 and SNU-C1 that were treated with 5% cell-free ascites for 24 hours. In all experiments, 25 µg of protein was used for total STAT3 and p-STAT3(Y705) ELISA following the manufacturer's instructions.

In Vitro Drug Treatment

A total of 5,000 cells/wells were seeded in 96-well plates and were grown for 24 hours in serum-free RPMI medium supplemented with 5% cell-free ascites or complete media, and then treated with various concentrations of TM5441

(PAI-1 inhibitor), Tiplaxtinin (PAI-1 inhibitor), Napabucasin (STAT3 inhibitor), BEZ235 (dual PI3K/mTOR inhibitor) and Mitomycin C (chemotherapeutic agent used in hyperthermic intraperitoneal chemotherapy (HIPEC)) for 72 hours. Cell proliferation was assessed using CellTitreGlo assay (Promega, Madison, US). These experiments were performed in triplicates and were repeated at least 3 times.

Patient-Derived Ascites-Dependent Xenografts (PDADXs) Generation

All mice experiments were performed according to protocols approved by SingHealth Institutional Animal Care and Use Committee (IACUC Ref: 2017/SHS/1295). Ascites collected from patients with peritoneal carcinomatosis were centrifuged at 2000 g for 10 minutes to concentrate the cellular components and to separate the fluid component. 1 mL of cell pellet was resuspended with 1 mL of ascitic fluid and 400 μL of the mixture was implanted intraperitoneally into 6-week-old BALB/c nude mice (n=5 mice) to generate patient-derived ascites-dependent xenograft (PDADX) passage 0 (P0). For subsequent passages, patient-derived ascites-dependent xenograft (PDADX) tumours were diced into small pieces using scalpel blades and passed through an 18-G syringe needle. Diced tumours were resuspended with matched patient's ascites at 1:1 ratio and implanted intraperitoneally into 6-week-old BALB/c nude mice (n=10 mice).

In Vivo PC Cell Line Mouse Model Drug Treatment

To determine the efficacy of PAI-1 inhibition in different susceptibility ascites groups in vivo, $5\times10^6$ of Colo-205 cells were co-injected with cell-free ascites representative of PAI-1 paracrine addicted (PPA) group, co-activators predominant (CAP) group or foetal bovine serum (FBS) into abdominal cavity of 6- to 8-week-old BALB/c nude mice (female, n=5 mice/group) and treated with 1.75 mM TM5441 administered intraperitoneally. Ascites and drug treatment were performed by injecting 400 μL of 5% cell-free ascites or 10% foetal bovine serum (FBS) with TM5441 intraperitoneally every 3 days for a duration of 21 days. After 3 weeks, the mice were sacrificed and tumour burden was quantified based on a modified peritoneal carcinomatosis index (PCI) score and presented as total peritoneal carcinomatosis index (PCI) score. Total peritoneal carcinomatosis index (PCI) score was calculated based on the sum of score for each region and ranges from 0 to 39.

To determine the optimal drug concentration and drug delivery method, a total of 16 female BALB/c nude mice with the age of 6-8 weeks old were selected for the experiment. Each mouse was injected with $5\times10^6$ of Colo-205 cells intraperitoneally. The mice were divided into 4 groups and given the following treatments: (i) 5% cell-free ascites with 1% DMSO, (ii) 5% cell-free ascites with 1 mM TM5441, (iii and iv) 5% cell-free ascites with 2 mM TM5441. Treatment was performed by injecting 400 μL of 5% cell-free ascites with DMSO vehicle/drug intraperitoneally (i-iii) and orally (iv) every 3 days, up to 21 days. After 3 weeks, the mice were sacrificed and tumour burden was quantified based on a modified peritoneal carcinomatosis index (PCI) score and presented as total peritoneal carcinomatosis index (PCI) score. Total peritoneal carcinomatosis index (PCI) score was calculated based on the sum of score for each region and ranges from 0 to 39.

Patient-Derived Ascites-Dependent Xenografts (PDADXs) Drug Treatment

Matched patient's cell-free ascites and its cellular components were used to generate patient-derived ascites-dependent xenografts (PDADXs) to better recapitulate peritoneal carcinomatosis patients. PAI-1 paracrine addicted (PPA) patient-derived ascites-dependent xenograft (PDADX) tumours (100 mg) were implanted into 16 female BALB/c nude mice intraperitoneally and co-activators predominant (CAP) patient-derived ascites-dependent xenograft (PDADX) tumours (100 mg) were implanted into 16 female BALB/c nude mice intraperitoneally. PAI-1 paracrine addicted (PPA) patient-derived ascites-dependent xenograft (PDADX) and co-activators predominant (CAP) patient-derived ascites-dependent xenograft (PDADX) were then divided into 4 groups and given the following treatments: (i) 5% PAI-1 paracrine addicted (PPA) or co-activators predominant (CAP) cell-free ascites with 1% DMSO, (ii) 5% PAI-1 paracrine addicted (PPA) or co-activators predominant (CAP) cell-free ascites with 2 mM TM5441, (iii) 10% foetal bovine serum (FBS) with 1% DMSO and (iv) 10% foetal bovine serum (FBS) with 2 mM TM5441. Treatment was performed via intraperitoneal administration every 3 days for 21 days. Tumour burden was quantified by weighing all visible tumours after mice were sacrificed.

To determine if susceptibility to PAI-1 inhibition is reliant on cell-free ascites and not tumours, co-activators predominant (CAP) patient-derived ascites-dependent xenograft (PDADX) whose patient's cell-free ascites are not responsive to PAI-1 inhibition was treated with PAI-1 paracrine addicted (PPA) cell-free ascites. Briefly, co-activators predominant (CAP) patient-derived ascites-dependent xenograft (PDADX) tumours (100 mg) were implanted into 16 female BALB/c nude mice intraperitoneally. The mice were divided into 4 groups and given the following treatment: (i) 5% co-activators predominant (CAP) cell-free ascites with 1% DMSO, (ii) 5% co-activators predominant (CAP) cell-free ascites with 2 mM TM5441, (iii) 5% PAI-1 paracrine addicted (PPA) cell-free ascites with 1% DMSO, and (iv) 5% PAI-1 paracrine addicted (PPA) cell-free ascites with 2 mM TM5441. Treatment was performed via intraperitoneal administration every 3 days for 21 days. Tumour burden was quantified by weighing all visible tumours after mice were sacrificed.

p-STAT3 Surrogate Marker Selection

STAT3-related genes were identified from Kyoto Encyclopedia of Genes and Genomes (KEGG) database by compiling all genes that are involved in known STAT3 pathways. Secreted STAT3-related proteins were selected based on extracellular genes listed in NCBI's Biosystems database and proteins identified in mass spectrometry analysis of cell-free ascites. Transcriptomics comparison was performed using 2 databases to prioritize putative STAT3 surrogate markers. First database was used to determine genes that are positively correlated with STAT3 in TCGA COADREAD data set. Genes were ranked from most positively correlated to least correlated with STAT3. Second database was derived from microarray analysis of PAI-1 paracrine addicted (PPA) cell-free ascites-treated cells exposed to TM5441 to determine genes that are downregulated and upregulated in PPA cell-free ascites-treated cells in response to PAI-1 inhibition. Upregulated genes were also of interest as these might represent genes that are involved in rescue mechanisms in response to PAI-1 inhibition. Similarly, genes were ranked from most downregulated to most upregulated. Systematic paired correlation analysis of candidate genes was subsequently performed by focusing on top 1% and top 25% of genes positively correlated with STAT3 in database 1, and top 1% and top 25% of most downregulated and upregulated genes in database 2. The paired analysis for each group was prioritised and representative genes were chosen from each group based on literature review to streamline to 35 genes. 10 targets were selected based on rank prioritisation, potential good correlation with p-STAT3 from Luminex assay data, and the importance of the candidate genes in cancer pathogenesis from literature review for further evaluation with ELISA. The concentrations of each surrogate marker in cell-free ascites were correlated with ascites-treated cells p-STAT3 levels using Spearman correlation analysis.

What is claimed is:

1. A method of treating a subject suffering from peritoneal carcinomatosis determined to be susceptible to treatment with a plasminogen activator inhibitor 1 (PAI-1) inhibitor, the method comprising measuring the concentration of PAI-1 and determining the level of phosphorylation of signal transducer and activator of transcript 3 (STAT3) in a sample obtained from the subject;

comparing the concentration of PAI-1 and the level of STAT3 phosphorylation in the sample to a reference value;

determining the subject to be susceptible to treatment with the PAI-1 inhibitor when the sample obtained from the subject shows an increase in PAI-1 concentration and an increase in STAT3 phosphorylation compared to the reference value; and administering an effective amount of the PAI-1 inhibitor via intraperitoneal administration to the subject determined to be susceptible to treatment with the PAI-1 inhibitor, thereby treating the subject suffering from peritoneal carcinomatosis.

2. The method of claim 1, wherein the concentration of PAI-1 is determined by measuring the concentration of PAI-1 directly, and/or in one or more complexes.

3. The method of claim 1, wherein the level of STAT3 phosphorylation is determined by measuring the concentration of one or more surrogate markers, and/or by measuring the concentration of STAT3 phosphorylation directly.

4. The method of claim 3, wherein the surrogate markers are selected from the group consisting of interleukin (IL6), interleukin (IL10), chemokine (C—C motif) ligand 2 (CCL2), matrix metallopeptidase 9 (MMP9), angiopoietin 1 (ANGPT1), transforming growth factor beta 1 (TGFB1), periostin, PN, or osteoblast-specific factor OSF-2 (POSTN), (V-set and immunoglobulin domain containing 4 (VSIG4), cluster of differentiation 44 (CD44), and C—X—C motif chemokine 10 (CXCL10).

5. The method of claim 3, wherein the surrogate markers are selected from the group consisting of interleukin (IL6), interleukin (IL10), chemokine (C—C motif) ligand 2 (CCL2), matrix metallopeptidase 9 (MMP9), and angiopoietin 1 (ANGPT1).

6. The method of claim 3, wherein the surrogate markers are selected from the group consisting of interleukin (IL6), interleukin (IL10), chemokine (C—C motif) ligand 2 (CCL2), and matrix metallopeptidase 9 (MMP9).

7. The method of claim 3, wherein the surrogate markers are selected from the group consisting of interleukin (IL6), transforming growth factor beta 1 (TGFB1), periostin, PN, or osteoblast-specific factor OSF-2 (POSTN), (V-set and immunoglobulin domain containing 4 (VSIG4), cluster of differentiation 44 (CD44), and C—X—C motif chemokine 10 (CXCL10).

8. The method of claim 3, wherein the surrogate markers are selected from the group consisting of TGFB1, POSTN, VSIG4, CD44, and CXCL10.

9. The method of claim 1, wherein the PAI-1 inhibitor is an anti-cancer drug or an anti-cancer treatment.

10. The method of claim 9, wherein the anti-cancer drug or the anti-cancer therapy is selected from the group consisting of a small molecule, a chemotherapeutic agent, a peptide, an antibody, combinations thereof, and combination therapy.

11. The method of claim 9, wherein the anticancer drug is selected from the group consisting of TM5441 (5-Chloro-2 [[2-[2 [[3-(3-furanyl)phenyl]amino]-2-oxoethoxy]acetyl] amino]benzoic acid; CAS 1190221-43-2), TM5007 (N, N-bis [3,3'-carboxy-4,4'-(2,2'-thienyl)-2,2'-thienyl] hexanedicarboxamide; CAS 342595 May 5), TM5275 (5-Chloro-2-[[2-[2-[4-(diphenylmethyl)-1-piperazinyl]-2-oxoethoxy]acetyl]amino]-benzoic acid sodium salt; CAS 1103926-82-4), tiplaxtinin (2-(1-Benzyl-5-(4-(trifluoromethoxy)phenyl)-1H-indol-3-yl)oxoacetic acid; CAS 393105-53-8), ZK4044, and derivatives thereof.

12. The method of claim 1, wherein the PAI-1 inhibitor is administered intra-peritoneally.

13. The method of claim 1, wherein the peritoneal carcinomatosis is selected from the group consisting of colorectal peritoneal carcinomatosis, small bowel peritoneal carcinomatosis, mesothelioma, endometrial peritoneal carcinomatosis, gastric peritoneal carcinomatosis, ovarian peritoneal carcinomatosis, appendiceal peritoneal carcinomatosis, pancreatic peritoneal carcinomatosis, urothelial carcinomatosis and Pseudomyxoma peritonei (PMP).

14. The method of claim 1, wherein the sample is selected from the group consisting of ascites, blood, serum, urine, drain fluid, surgical drain fluid, supernatant obtained from cells, supernatant obtained from organs, supernatant obtained from tissues, lymph, supernatant obtained from lymph nodes, liquid biopsy samples and supernatant obtained from biopsy samples.

15. The method of claim 1, wherein the method is performed in a treatment setting selected from the groups consisting of neoadjuvant setting, adjuvant setting, palliative setting and prophylactic setting.

16. The method of claim 1, wherein the reference value is from subjects suffering from peritoneal Carcinomatosis.

17. The method of claim 1, wherein administration of the PAI-1 inhibitor leads to inhibition of PAI-1 activity compared to patients suffering from the same disease.

18. A panel of markers for treating a patient suffering from peritoneal Carcinomatosis with a "plasminogen activator inhibitor 1" (PAI-1) inhibitor, wherein the panel of markers comprises PAI-1, and one or more surrogate markers of STAT3 phosphorylation or p-STAT3.

19. The panel of claim 18, wherein the panel comprises PAI-1, and one or more or all of IL6, 1110, CCL2, and MMP9; or wherein the panel comprises PAI-1, and one or more or all of IL6, IL10, CCL2, MMP9 and ANGPT1, or wherein the panel comprises PAI-1, and one or more or all of TGFB1, POSTN, VSIG4, CD44, and CXCL10; or wherein the panel comprises PAI-1, and one or more or all of TFGB1, POSTN, VSIG4, CD44, and CXCL10; or wherein the panel comprises PAI-1, and one or more or all of IL6, TFGB1, POSTN, VSIG4, CD44, and CXCL10.

* * * * *